United States Patent
Chen et al.

(10) Patent No.: US 6,916,809 B2
(45) Date of Patent: Jul. 12, 2005

(54) HETEROCYCLIC ACRIDONE INHIBITORS OF IMPDH ENZYME

(75) Inventors: Ping Chen, Belle Mead, NJ (US); T.G. Murali Dhar, Newtown, PA (US); Edwin J. Iwanowicz, West Windsor, NJ (US); Scott H. Watterson, Pennington, NJ (US); Henry Gu, Bordentown, NJ (US); Yufen Zhao, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 27 days.

(21) Appl. No.: 10/325,009

(22) Filed: Dec. 20, 2002

(65) Prior Publication Data
US 2003/0181497 A1 Sep. 25, 2003

Related U.S. Application Data
(60) Provisional application No. 60/343,234, filed on Dec. 21, 2001.

(51) Int. Cl.[7] .................... C07D 471/14; C07D 471/04; A61K 31/4375; A61P 19/02; A61P 17/06
(52) U.S. Cl. ..................... 514/230.5; 514/255.05; 514/256; 514/293; 544/105; 544/333; 544/405; 544/60; 544/126; 544/361; 544/250; 546/81; 540/575
(58) Field of Search ................ 544/105, 333, 544/405, 60, 126, 361; 546/81; 514/230.5, 255.05, 256, 293; 540/575

(56) References Cited

U.S. PATENT DOCUMENTS

| | | |
|---|---|---|
| 3,835,139 A | 9/1974 | Pfister et al. |
| 4,250,182 A | 2/1981 | Gorvin |
| 4,374,984 A | 2/1983 | Eichler et al. |
| 4,686,234 A | 8/1987 | Nelson et al. |
| 4,725,622 A | 2/1988 | Nelson et al. |
| 4,727,069 A | 2/1988 | Nelson et al. |
| 4,753,935 A | 6/1988 | Nelson et al. |
| 4,786,637 A | 11/1988 | Allison et al. |
| 4,808,592 A | 2/1989 | Nelson et al. |
| 4,861,776 A | 8/1989 | Nelson et al. |
| 4,868,153 A | 9/1989 | Allison et al. |
| 4,948,793 A | 8/1990 | Allison et al. |
| 4,952,579 A | 8/1990 | Nelson et al. |
| 4,959,387 A | 9/1990 | Nelson et al. |
| 4,992,467 A | 2/1991 | Allison et al. |
| 5,247,083 A | 9/1993 | Knox et al. |
| 5,380,879 A | 1/1995 | Sjogren |
| 5,444,072 A | 8/1995 | Patterson et al. |
| 5,665,583 A | 9/1997 | Collart et al. |
| 5,807,876 A | 9/1998 | Armistead et al. |
| 2004/0053955 A1 | 3/2004 | Iwanowicz et al. |

FOREIGN PATENT DOCUMENTS

| | | |
|---|---|---|
| CA | 1009576 | 5/1977 |
| CA | 1009660 | 5/1977 |
| DE | 2243997 | 3/1973 |
| EP | 0 054 812 | 6/1982 |
| GB | 1382259 | 1/1975 |
| JP | 63-305173 | 12/1988 |
| JP | 11-130767 | 5/1999 |
| WO | WO 94/01105 | 1/1994 |
| WO | WO 94/12184 | 6/1994 |
| WO | WO 97/40028 | 10/1997 |
| WO | WO 98/15546 | 4/1998 |
| WO | WO 98/40381 | 9/1998 |
| WO | WO 00/23415 | 4/2000 |
| WO | WO 00/23416 | 4/2000 |
| WO | WO 03/059269 | 7/2003 |

OTHER PUBLICATIONS

Chen et al. (J. Med. Chem. 1994, 37, 593–597).*
Stewart, G. et al., Aust. J. Chem., vol. 37, pp. 1939–1950 (1984).
Chemical Abstracts, vol. 123, No. 3 (1995), abstract No. 32927 g.
SciFinder Acridones Listing of Abstracts.
Canelos, P.A. et al., Abstract 486: "Rolipram, a Type 4 Phosphodiesterase (PDE) Inhibitor, Promotes Induction of Neoantigen Tolerance in Murine T Cells" (593), J. Allergy Clin. Immunol. vol. 107, No. 2, p. S147.

(Continued)

Primary Examiner—Mark L Berch
Assistant Examiner—Kahsay Habte
(74) Attorney, Agent, or Firm—Terence J. Bogie; Stephen B. Davis

(57) ABSTRACT

Compounds having the formula (I),

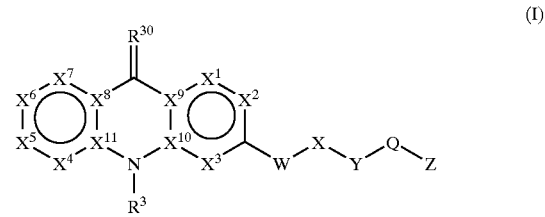

wherein $R^3$ is selected from H, OH and $NH_2$; $R^{30}$ is selected from =O and =S; W is —C(=O)—, —S(=O)—, or —S(O)$_2$—; or W may be —CH$_2$— if X is —C(=O)—; X is selected from —CH$_2$—, —N($R^4$)—, and —O—, except that when W is —CH$_2$—, X is —C(=O)—; Y is a bond or —C($R^{40}$)($R^{45}$)—; Q is a linker; Z is optionally substituted alkyl, alkenyl, alkynyl, cycloalkyl, aryl, heteroaryl, or heterocyclyl; and $X^1$, $X^2$, $X^3$, $X^4$, $X^5$, $X^6$, $X^7$, $X^8$, $X^9$, $X^{10}$ and $X^{11}$ are selected such a tricyclic heteroaryl ring system is formed as further defined in the specification.

9 Claims, No Drawings

OTHER PUBLICATIONS

Carr, S.F. et al., "Characterization of Human Type I and Type II IMP Dehydrogenases", The Journal of Biological Chemistry, vol. 268, No. 36, pp. 27286–27290 (1993).

Collart, F.R. et al., "Cloning and Sequence Analysis of the Human and Chinese Hamster Inosine–5'–monophosphate Dehydrogenase cDNAs", The Journal of Biological Chemistry, vol. 263, No. 3, pp. 15769–15772 (1988).

Jackson, R.C. et al., "IMP dehydrogenase, an enzyme linked with proliferation and malignancy", Nature, vol. 256, pp. 331–333 (1975).

Konno, Y. et al., "Expression of Human IMP Dehydrogenase Types I and II in *Escherichia coli* and Distribution in Human Normal Lymphocytes and Leukemic Cell Lines", The Journal of Biological Chemistry, vol. 266, No. 1, pp. 506–509 (1991).

Natsumeda, Y. et al., "Two Distinct cDNAs for Human IMP Dehydrogenase", The Journal of Biological Chemistry, vol. 265, No. 9, pp. 5292–5295 (1990).

* cited by examiner

HETEROCYCLIC ACRIDONE INHIBITORS OF IMPDH ENZYME

RELATED APPLICATIONS

This application claims the benefit of U.S. Provisional Application No. 60/343,234, filed Dec. 21, 2001, incorporated herein by reference.

FIELD OF THE INVENTION

The present invention relates to compounds which inhibit IMPDH, to methods of making such compounds, and to pharmaceutical compositions containing these compounds. The compounds and pharmaceutical compositions of the invention can be used as therapeutic agents for IMPDH-associated disorders.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"), Jackson et al., *Nature*, 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated. These transcripts are labeled type I and type II and are of identical size (514 amino acids). Collart et al., *J. Biol. Chem.*, 263:15769–15772 (1988); Natsumeda et al., *J. Biol. Chem.*, 265:5292–5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Inhibitors of IMPDH have also been described in the art. WO 97/40028 and U.S. Pat. No. 5,807,876 describe a class of urea derivatives that possess a common urea backbone. WO 98/40381 describes a series of heterocyclic substituted anilines as inhibitors of IMPDH.

Tiazofurin, ribavirin and mizoribine also inhibit IMPDH. These nucleoside analogs are competitive inhibitors of IMPDH; however, these agents inhibit other NAD dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection and autoimmune disorders, psoriasis, inflammatory diseases, including rheumatoid arthritis, tumors and for the treatment of allograft rejection. These are described in U.S. Pat. Nos. 4,686,234, 4,725,622, 4,727,069, 4,753,935, 4,786,637, 4,808,592, 4,861,776, 4,868,153, 4,948,793, 4,952,579, 4,959,387, 4,992,467, and 5,247,083.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

The combination of agents for prevention and/or treatment of IMPDH-associated disorders, especially allograft rejection, has been investigated. In one study, it was observed that cyclic AMP agonists, such as the Type 4 Phosphodiesterase (PDE4) inhibitor Rolipram [4-[3-(cyclopentyloxy)-4-methoxy-phenyl]-2-pyrrolidinone] (Schering AG), synergized with IMPDH inhibitor MPA by a cAMP- and IMPDH-dependent mechanism. (P. A. Canelos et al., *J. Allergy and Clinical Immunology*, 107:593 (2001)). The investigators found that cyclic AMP agonists, such as the PDE4 inhibitor Rolipram (Rol), markedly downregulated antigen-specific T lymphocyte responses through their effects on a variety of signaling pathways. The study defined the potential to use a low concentration of Rol ($10^{-7}$ M, approximate $IC_{10}$) to synergize with a variety of immunosuppressive agents for the prevention and/or treatment of allograft rejection. While little or no synergistic effect on inhibition of antigen-induced proliferation (assessed by $^3$H Thymidine incorporation) could be demonstrated with calcineurin antagonists (cyclosporine and tacrolimus), sirolimus, or corticosteroids, a marked synergistic effect was demonstrated with MPA, the active metabolite of mycophenolate mofetil (CellCept, Roche). This effect was statistically significant over 4 orders of magnitude ($10^{-6}$ to $10^{-9}$ M). This synergism was recapitulated with dibuteryl-cAMP ($2 \times 10^{-6}$ M, approximate $IC_{10}$) and inhibited with the use of H-9, suggesting a mechanism involving both cAMP and protein kinase A.

Since MPA is a selective, uncompetitive, and reversible inhibitor of IMPDH, a key enzyme in the purine salvage pathway, the potential for cAMP-mediated cross-talk at this locus was further investigated. It was found that gene expression for IMPDH types I and II (assessed by RT-PCR) remained unaffected by the administration of rolipram, MPA, or both at low and high concentrations. However, functional reversal of the synergistic effect was demonstrated with the use of deoxyguanosine, a specific antagonist of MPA on IMPDH (% inhibition of proliferation 81±16 vs. 35±12, p<0.05). Finally, despite a marked synergistic effect on inhibition of proliferation, no significant downregulation in the generation of proinflammatory cytokines (IL-2, IL-4, and IFN, each assessed by RT-PCR), could be detected with the administration of Rol $10^{-7}$ M, MPA $10^{-8}$ M, or the combination. It was concluded that Rol demonstrates marked synergy with MPA by a cAMP- and IMPDH-dependent mechanism. The utility of this combination of agents for the induction of T cell tolerance was suggested by the specificity of the observed effect for proliferation, without the abrogation of cytokine generation and early signaling processes.

Unlike type I, type II mRNA is preferentially upregulated in human leukemic cell lines K562 and HL-60. Weber, *J. Biol. Chem.*, 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.*, 268:27286–27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention are effective inhibitors of IMPDH. Inhibitors of IMPDH enzyme are also described in U.S. patent application Ser. No. 10/324,306, titled "Acridone Inhibitors of IMPDH Enzyme," having the same assignee as the present invention and filed concomitantly herewith, the entire contents of which is incorporated herein by reference. Said application also claims priority to U.S. patent application Ser. No. 60/343,234, filed Dec. 21, 2001.

SUMMARY OF THE INVENTION

The present invention provides compounds of the following formula (I), their enantiomers, diastereomers, tautomers and pharmaceutically acceptable salts and solvates thereof, for use as IMPDH inhibitors:

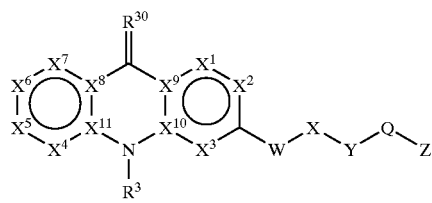

(I)

wherein:

$X^1$ is selected from a bond, $CR^1$ and N;
$X^2$ is selected from $CR^{25}$, N, $NR^2$, O and S;
$X^3$ is selected from $CR^1$, N, $NR^2$, O and S;
$X^4$ is selected from $CR^1$, N, $NR^2$, O and S;
$X^5$ is $CR^1$ or N;
$X^6$ is selected from $CR^{25}$, N, $NR^2$, O, and S;
$X^7$ is selected from a bond, $CR^1$ and N;
$X^8$, $X^9$, $X^{10}$ and $X^{11}$ are independently selected from C and N;

Provided, however, that at least one of $X^1$, $X^2$, $X^3$, $X^4$, $X^5$, $X^6$, $X^7$, $X^8$, $X^9$, $X^{10}$ and $X^{11}$ is N, $NR^2$, O or S; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;

W is —C(=O)—, —S(=O)—, or —S(O)$_2$—; or W may be —CH$_2$— if X is —C(=O)—, —S(=O)—, or —S(O)$_2$—;

X is selected from —CH$_2$—, —N(R$^4$)—, and —O—, except that when W is —CH$_2$—, X is selected from —C(=O)—, —S(=O)—, or —S(O)$_2$—;

Y is a bond or —C(R$^{40}$)(R$^{45}$)—;

Q is selected from a bond, —C(R$^{26}$)(R$^{46}$)—, —C(=O)—, —CH$_2$—O—, —CH$_2$—O—CH$_2$—, —CH$_2$—CO$_2$—NR$^4$—, —CH$_2$—CO$_2$—, —C(=O)NR$^4$—, and —CH=C(R$^{26}$)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C(R$^{40}$)(R$^{45}$)— and Q is a bond or —C(R$^{26}$)(R$^{46}$)—, Z may be CO$_2$H or CO$_2$alkyl;

$R^1$ is the same or different and is selected from hydrogen, halogen, cyano, alkyl, substituted alkyl, alkenyl, substituted alkenyl, alkynyl, substituted alkynyl, O—R$^7$, —(C=O)R$^7$, —(C=O)—O—R$^7$, NR$^8$R$^9$, —(C=O)NR$^8$R$^9$, —SR$^{20}$, —S(=O)R$^{20}$, —SO$_2$R$^{20}$ and —C≡C—Si(OH$_3$)$_3$;

$R^2$ is selected from hydrogen, alkyl, substituted alkyl, aryl, substituted aryl, heteroaryl, substituted heteroaryl, heterocyclyl and substituted heterocyclyl;

$R^3$ is selected from H, OH and NH$_2$;

$R^4$ is selected from H, OH and C$_{1-4}$ alkyl;

$R^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, —C(=O)—NR$^8$R$^9$, C(=O)heteroaryl, aryl, substituted aryl, heterocyclo, substituted heterocyclo, heteroaryl and substituted heteroaryl;

$R^8$ and $R^9$ are independently selected from hydrogen, OR$^7$, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or $R^8$ and $R^9$ are taken together with the nitrogen atom to which they are attached to form a substituted or unsubstituted heterocyclic ring of 3 to 8 atoms, or substituted or unsubstituted heteroaryl ring of 5 atoms;

$R^{20}$ is selected from alkyl and substituted alkyl;

$R^{25}$ is the same or different and is selected from hydrogen, halogen, nitro, cyano, alkyl, substituted alkyl, alkenyl, substituted alkenyl, alkynyl, substituted alkynyl, O—R$^7$, NR$^8$R$^9$, SR$^7$, S(O)R$^7$, SO$_2$R$^7$, SO$_3$R$^7$, SO$_2$NR$^8$R$^9$, —C(=O)R$^7$, CO$_2$R$^7$, C(=O)NR$^8$R$^9$, and —C=C—Si(CH$_3$)$_3$;

$R^{30}$ is selected from =O and =S;

$R^{26}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$cycloalkyl ring; and $R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms.

The present invention also relates to pharmaceutical compositions containing compounds of formula (I), and methods for treating IMPDH-associated disorders using the compounds of formula (I), alone or in combination with PDE4 inhibitors.

DETAILED DESCRIPTION OF THE INVENTION

The following are definitions of the terms as used throughout this specification and claims. The initial definition provided for a group or term herein applies to that group or term throughout the present specification, individually or as part of another group, unless otherwise indicated.

The term "alkyl" refers to straight or branched chain hydrocarbon groups having 1 to 12 carbons atoms, preferably 1 to 8 carbon atoms, and most preferably 1 to 4 carbon atoms. The term "lower alkyl" refers to an alkyl group of 1 to 4 carbon atoms.

The term "substituted alkyl" refers to an alkyl group as defined above, having one, two, or three substituents selected from the group consisting of halo, cyano, O—$R^5$, S—$R^5$, NR$^6$R$^{6a}$, nitro, oxo, cycloalkyl, substituted cycloalkyl, aryl, substituted aryl, heterocyclo, substituted heterocyclo, heteroaryl, substituted heteroaryl, CO$_2$R$^5$, S(O)R$^5$, SO$_2$R$^5$, SO$_3$R$^5$, SO$_2$NR$^6$R$^{6a}$, C(=O) NR$^6$R$^{6a}$, NR$^6$CO$_2$R$^{6a}$, C$_2$NR$^6$NR$^{6a}$ and C(=O)R$^5$.

The term "alkenyl" refers to straight or branched chain hydrocarbon groups having 2 to 12 carbon atoms and one, two or three double bonds, preferably 2 to 6 carbon atoms and one double bond.

The term "substituted alkenyl" refers to an alkenyl group as defined above having one, two, or three substituents selected from the group consisting of halo, cyano, O—$R^5$, S—$R^5$, NR$^6$R$^{6a}$, nitro, oxo, cycloalkyl, substituted cycloalkyl, aryl, substituted aryl, heterocyclo, substituted heterocyclo, heteroaryl, substituted heteroaryl, CO$_2$R$^5$, S(O)R$^5$, SO$_2$R$^5$, SO$_3$R$^5$, SO$_2$NR$^6$R$^{6a}$, C(=O)NR$^6$R$^{6a}$, NR$^6$CO$_2$R$^{6a}$, CO$_2$NR$^6$R$^{6a}$ and C(=O)R$^5$.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above having one, two or three substituents selected from the group consisting of halo, cyano, O—$R^5$, S—$R^5$, NR$^6$R$^{6a}$, nitro, cycloalkyl, substituted cycloalkyl, oxo, aryl, substituted aryl, heterocyclo, heteroaryl, CO$_2$R$^5$, S(O)R$^5$, SO$_2$R$^5$, SO$_3$R$^5$, SO$_2$NR$^6$R$^{6a}$, C(=O)NR$^6$R$^{6a}$, and C(=O)R$^5$.

The term "halo" refers to chloro, bromo, fluoro, and iodo, with chloro, bromo and fluoro being preferred.

The term "cycloalkyl" refers to fully saturated and partially unsaturated monocyclic hydrocarbon rings of 3 to 9, preferably 3 to 7 carbon atoms. Also included in this definition are bicyclic rings where the cycloalkyl ring as defined above has a bridge of one, two or three carbon atoms in the bridge, or a second ring attached in a fused or spiro fashion, i.e., a fused aryl, substituted aryl, cycloalkyl, substituted cycloalkyl, heterocyclo, substituted heterocyclo, heteroaryl or substituted heteroaryl ring, or a spirocycloalkyl or spiroheterocycloalkyl ring, provided that the point of attachment is in the cycloalkyl ring.

Thus, the term "cycloalkyl" includes cyclopropyl, cyclobutyl, cyclopentyl, cyclohexyl, cycloheptyl, cyclooctyl, etc., as well as the following ring systems,

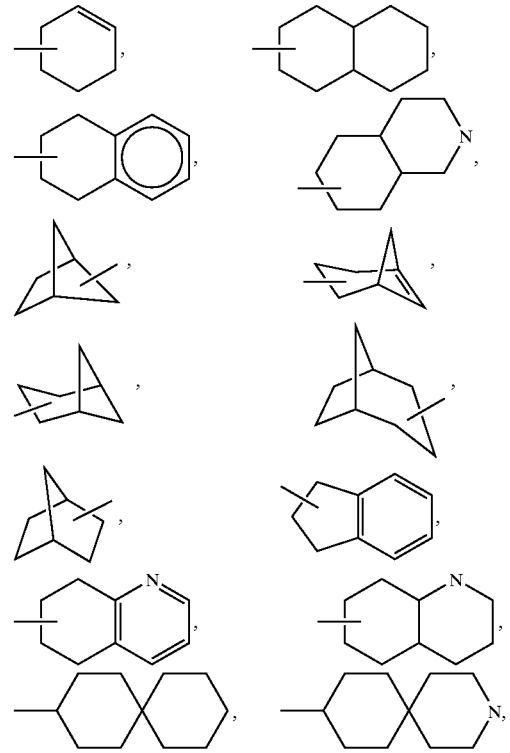

and so forth.

The term "substituted cycloalkyl" refers to such cycloalkyl groups as defined above having one, two or three substituents attached to any available carbon atom of a monocyclic ring or any available carbon or nitrogen atom of a bicyclic ring, wherein said substituents are selected from the group consisting of halogen, nitro, alkyl, substituted alkyl, alkenyl, cyano, cycloalkyl, aryl, heterocyclo, heteroaryl, oxo (=O), —OR$^5$, —CO$_2$R$^5$, —C(=O)NR$^6$R$^{6a}$, —OC(=O)R$^5$, —OC(=O)R$^5$, —OC(=O)OR$^6$R$^{6a}$, —OCH$_2$CO$_2$R$^5$, —C(=O)R$^5$, NR$^6$R$^{6a}$, —NR$^{10}$C(=O)R$^5$, —NR$^{10}$C(=O)OR$^5$, —NR$^{10}$C(=O)C(=O)OR$^5$, —NR$^{10}$C(=O)C(=O)NR$^6$R$^{6a}$, —NR$^{10}$C(=O)C(=O) alkyl, —NR$^{10}$C(NCN)OR$^5$, NR$^{10}$C(=O)NR$^6$R$^{6a}$, —NR$^{10}$(NCN)NR$^6$R$^{6a}$, —NR$^{10}$C(NR$^{11}$)NR$^6$R$^{6a}$, —NR$^{10}$SO$_2$NR$^6$R$^{6a}$, —NR$^{10}$SO$_2$R$^5$, —SR$^5$, —S(O)R$^5$, —SO$_2$R$^5$, —SO$_3$R$^5$, —SO$_2$NR$^6$R$^{6a}$, —NHOR$^5$, —NR$^{10}$NR$^6$R$^{6a}$, —N[C(=O)R$^5$][OR$^{10}$], —N(CO$_2$R$^5$) OR$^{10}$, —C(=O)NR$^{10}$(CR$^{12}$R$^{13}$)$_r$R$^5$, —C(=O)(CR$^{12}$R$^{13}$)$_p$O(CR$^{14}$R$^{15}$)$_q$CO$_2$R$^5$, —C(=O)(CR$^{12}$R$^{13}$)$_r$OR$^5$, —C(=O)(CR$^{12}$R$^{13}$)$_p$Ö(CR$^{14}$R$^{15}$)$_q$R$^5$, —C(=O)(CR$^{12}$R$^{13}$)$_r$NR$^6$R$^{6a}$, —OC(=O)O(CR$^{12}$R$^{13}$)$_m$ NR$^6$R$^{6a}$, —OC(=O)N(CR$^{12}$-R$^{13}$)$_r$R$^5$, —O(CR$^{12}$R$^{13}$)$_m$ NR$^6$R$^{6a}$, —NR$^{10}$C(=O)(CR$^{12}$R$^{13}$)$_r$R$^5$, —NR$^{10}$C(=C)(CR$^{12}$R$^{13}$)$_r$OR$^5$, NR$^{10}$C(=NC)(CR$^{12}$R$^{13}$)$_r$R$^5$, —NR$^{10}$C(=O)(CR$^{12}$R$^{13}$)$_r$NR$^6$R$^{6a}$, —NR$^{10}$(CR$^{12}$R$^{13}$)$_m$OR$^5$, —NR$^{10}$(C$^{12}$R$^{13}$)$_r$CO$_2$R$^5$, —NR$^{10}$(CR$^{12}$R$^{13}$)$_m$NR$^6$R$^{6a}$, —NR$^{10}$(CR$^{12}$R$^{13}$)$_n$SO$_2$(CR$^{14}$R$^{15}$)$_q$R$^5$, —C(=O)NR$^{10}$(CR$^{12}$R$^{13}$)$_n$SO$_2$(C$^{14}$R$^{15}$)$_q$R$^5$, —SO$_2$NR$^{10}$(CR$^{12}$R$^{13}$)$_n$CO(CR$^{14}$R$^{15}$)$_q$R$^5$, —SO$_2$NR$^{10}$(CR$^{12}$R$^{13}$)$_m$OR$^5$, and —SO$_2$NR$^{10}$ (CR$^{12}$R$^{13}$)$_n$Si(alkyl)$_3$.

When a substituted cycloalkyl is substituted with a second ring, including an aryl, heterocyclo, or heteroaryl ring, or a second cycloalkyl ring, said second ring in turn is optionally substituted with one to three R$^{17}$ groups as defined below.

It should be understood that a "substituted cycloalkyl" may have a substituent attached to any atom of the cycloalkyl ring, including its point of attachment to another group. Thus, for example, a cycloalkyl group substituted with a group "R" may comprise,

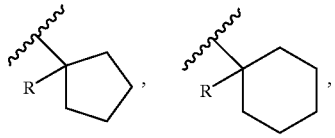

and so forth, where R is a substituent on a cycloalkyl group as defined above.

The term "aryl" refers to the phenyl, 1-naphthyl, and 2-naphthyl, preferably phenyl, as well as an aryl ring having a fused cycloalkyl, substituted cycloalkyl, heterocyclo, substituted heterocyclo, heteroaryl, or substituted heteroaryl ring, provided that the point of attachment is in the aryl ring. Thus, examples of aryl groups include Thus, examples of aryl groups include:

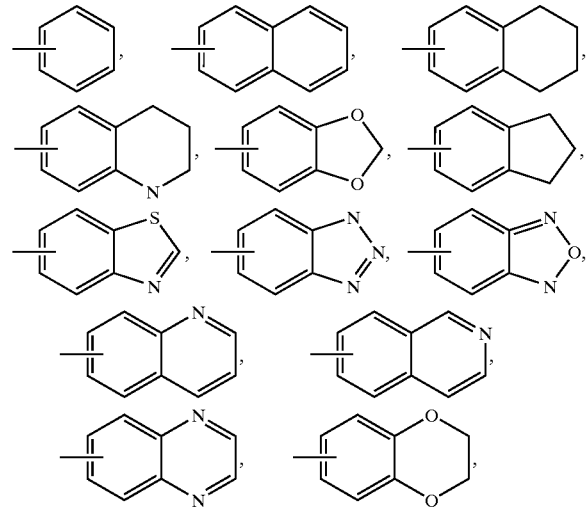

and so forth.

The term "substituted aryl" refers to such aryl groups as defined above having one, two, or three substituents selected from the group consisting of halogen, nitro, alkyl, substituted alkyl, alkenyl, cyano, cycloalkyl, aryl, heterocyclo, heteroaryl, —OR$^5$, —CO$_2$R$^5$, C(=O)NR$^6$R$^{6a}$, —OC(=O) R$^5$, —OC(=O)OR$^5$, —OC(=O)NR$^6$R$^{6a}$, —OCH$_2$CO$_2$R$^5$, —C(=O)R$^5$, NR$^6$R$^{6a}$, —NR$^{10}$C(=O)R$^5$, —NR$^{10}$C(=O) OR$^5$, —NR$^{10}$C(=O)C(=O)OR$^5$, —NR$^{10}$C(=O)C(=O) NR$^6$R$^{6a}$, —NR$^{10}$C(=O)C(=O)alkyl, —NR$^{10}$C(NCN) OR$^5$, NR$^{10}$C(=O)NR$^6$R$^{6a}$, —NR$^{10}$C(NCN)NR$^6$R$^{6a}$, —NR$^{10}$C(NR$^{11}$)NR$^6$R$^{6a}$, —NR$^{10}$SO$_2$NR$^6$R$^{6a}$, —NR$^{10}$SO$_2$R$^5$, —SR$^5$, —S(O)R$^5$, —SO$_2$R$^5$, —SO$_3$R$^5$, —SO$_2$NR$^6$R$^{6a}$, —NHOR$^5$, —NR$^{10}$NR$^6$R$^{6a}$, —N[C(=O) R$^5$][OR$^{10}$], —N(CO$_2$R$^5$)OR$^{10}$, —C(=O)NR$^{10}$(CR$^{12}$R$^{13}$)$_r$ R$^5$, —C(=O)(CR$^{12}$R$^{13}$)$_p$O(CR$^{14}$R$^{15}$)$_q$CO$_2$R$^5$, —C(=O) (CR$^{12}$R$^{13}$)$_r$OR$^5$, —C(=O)(CR$^{12}$R$^{13}$)$_p$O(CR$^{14}$R$^{15}$)$_q$R$^5$, —C(=O)(CR$^{12}$R$^{13}$)$_r$NR$^6$R$^{6a}$, —OC(=O)O(CR$^{12}$R$^{13}$)$_m$ NR$^6$R$^{6a}$, —OC(=O)N(CR$^{12}$R$^{13}$)$_r$R$^5$, —O(CR$^{12}$R$^{13}$)$_m$ NR$^6$R$^{6a}$, —NR$^{10}$C(=O)(CR$^{12}$R$^{13}$)$_r$R$^5$, —NR$^{10}$C(=O) (CR$^{12}$R$^{13}$)$_r$OR$^5$, —NR$^{10}$C(=NC)(CR$^{12}$R$^{13}$)$_r$R$^5$, —NR$^{10}$C (=O)(CR$^{12}$R$^{13}$)$_r$NR$^6$R$^{6a}$, —NR$^{10}$(CR$^{12}$R$^{13}$)$_m$OR$^5$, —NR$^{10}$ (CR$^{12}$R$^{13}$)$_r$CO$_2$R$^5$, —NR$^{10}$(CR$^{12}$R$^{13}$)$_m$NR$^6$R$^{6a}$, —NR$^{10}$ (CR$^{12}$R$^{13}$)$_n$SO$_2$(CR$^{14}$R$^{15}$)$_q$R$^5$, —C(=O)NR$^{10}$(CR$^{12}$R$^{13}$)$_n$ SO$_2$(CR$^{14}$R$^{15}$)$_q$R$^5$, —SO$_2$NR$^{10}$(CR$^{12}$R$^{13}$)$_n$CO(CR$^{14}$R$^{15}$)$_q$ R$^5$, —SO$_2$NR$^{10}$(CR$^{12}$R$^{13}$)$^m$OR$^5$, and —SO$_2$NR$^{10}$ (CR$^{12}$R$^{13}$)$_n$Si(alkyl)$_3$, as well as pentafluorophenyl.

When a substituted aryl is substituted with a second ring, including a cycloalkyl, heterocyclo, or heteroaryl ring, or a second aryl ring, said second ring in turn is optionally substituted with one to three R$^{16}$ groups as defined below.

The term "heterocyclo" refers to saturated or partially saturated monocyclic rings of 3 to 7 members and bicyclic rings of 7 to 11 members having one or two O or S atoms and/or one to four N atoms, provided that the total number of heteroatoms is four or less and that the heterocyclo ring contains at least one carbon atom. The nitrogen and sulfur atoms may optionally be oxidized, and the nitrogen atoms may optionally be quaternized. The bicyclic heterocyclo ring may also contain a bridge of one, two or three carbon atoms between available carbon or nitrogen atoms. The bicyclic heterocyclo rings may also have a cycloalkyl, substituted cycloalkyl, aryl, substituted aryl, heterocyclo, substituted heterocyclo, heteroaryl, or substituted heteroaryl ring fused to the monocyclic ring provided that the point of attachment is through an available carbon or nitrogen atom of the heterocyclo ring. Also included are heterocyclo rings having a second ring attached thereto in a spiro fashion The term "substituted heterocyclo" refers to a heterocyclo ring or ring system as defined above having one, two or three substituents on available carbon or nitrogen atom(s) selected from the group consisting of halogen, nitro, alkyl, substituted alkyl, alkenyl, cyano, cycloalkyl, aryl, heterocyclo, heteroaryl, oxo (=O), —OR$^5$, —CO$_2$R$^5$, —C(=O) NR$^6$R$^{6a}$, —OC(=O)R$^5$, —OC(=O)OR$^5$, —OC(=O) NR$^6$R$^{6a}$,—OCH$_2$CO$_2$R$^5$, —C(=O)R$^5$, NR$^6$R$^{6a}$, —NR$^{10}$C (=O)R$^5$, —NR$^{10}$C(=O)OR$^5$, —NR$^{10}$C(=O)C(=O)OR$^5$, NR$^{10}$C(=O)C(=O)NR$^6$R$^{6a}$, —NR$^{10}$C(=O)C(=O)alkyl, —NR$^{10}$C(NCN)OR$^5$, NR$^{10}$C(=O)NR$^6$R$^{6a}$, —NR$^{10}$C (NCN)NR$^6$R$^{6a}$, —NR$^{10}$C(NR$^{11}$)NR$^6$R$^{6a}$, —NR$^{10}$SO$_2$NR$^6$R$^{6a}$, —NR$^{10}$SO$_2$R$^5$, —SR$^5$, —S(O)R$^5$, —SO$_2$R$^5$, —SO$_3$R$^5$, —SO$_2$NR$^6$R$^{6a}$, —NHOR$^5$, —NR$^{10}$NR$^6$R$^{6a}$, —N[C(=O)R$^5$][OR$^{10}$], —N(CO$_2$R$^5$) OR$^{10}$, —C(=O)NR$^{10}$(CR$^{12}$R$^{13}$)$_r$R$^5$, —C(=O)(CR$^{12}$R$^{13}$)$_p$ O(CR$^{14}$R$^{15}$)$_q$CO$_2$R$^5$, —C(=O)(CR$^{12}$R$^{13}$)$_r$OR$^5$, —C(=O) (CR$^{12}$R$^{13}$)$_p$O(CR$^{14}$R$^{15}$)$_q$R$^5$, —C(=O)(CR$^{12}$R$^{13}$)$_r$NR$_6$R$^{6a}$, —OC(=O)(CR$^{12}$R$^{13}$)$_m$NR$^6$R$^{6a}$, —OC(=O)N(CR$^{12}$R$^{13}$)$_r$ R$^5$, —O(CR$^{12}$R$^{13}$)$_m$NR$^6$R$^{6a}$, —NR$^{10}$C(=O)(CR$^{12}$R$^{13}$)$_r$R$^5$, —NR$^{10}$C(=O)(CR$^{12}$R$^{13}$)$_r$OR$^5$, —NR$^{10}$C(=NC) (CR$^{12}$R$^{13}$)$_r$R$^5$, —NR$^{10}$C(=O)(CR$^{12}$R$^{13}$)$_r$NR$^6$R$^{6a}$, —NR$^{10}$ (CR$^{12}$R$^{13}$)$_m$OR$^5$, —NR$^{10}$(CR$^{12}$R$^{13}$)$_r$CO$_2$R$^5$, —NR$^{10}$ (CR$^{12}$R$^{13}$)$_m$NR$^6$R$^{6a}$, —NR$^{10}$(CR$^{12}$R$^{13}$)$_n$SO$_2$(CR$^{14}$R$^{15}$)$_q$R$^5$, —C(=)NR$^{10}$(CR$^{12}$R$^{13}$)$_n$SO$_2$(CR$^{14}$R$^{15}$)$_q$R$^5$, —SO$_2$NR$^{10}$ (CR$^{12}$R$^{13}$)$_n$CO(CR$^{14}$R$^{15}$)$_q$R$^5$, —SO$_2$NR$^{10}$(CR$^{12}$R$^{13}$)$_m$OR$^5$, and —SO$_2$NR$^{10}$(CR$^{12}$R$^{13}$)$_n$Si(alkyl)$_3$.

When a substituted heterocyclo is substituted with a second ring, including an aryl, cycloalkyl, or heteroaryl ring, or a heterocyclo ring, said second ring in turn is optionally substituted with one to three R$^{17}$ groups as defined below.

Exemplary monocyclic heterocyclo groups include pyrrolidinyl, pyrrolinyl, pyrazolinyl, pyrazolidinyl, oxetanyl, imidazolinyl, imidazolidinyl, oxazolidinyl, isothiazolidinyl, isoxazolinyl, thiazolidinyl, tetrahydrofuryl, piperidinyl, piperazinyl, tetrahydrothiopyranyl, tetrahydropyranyl, morpholinyl, thiamorpholinyl, thiamorpholinyl sulfoxide, thiamorpholinyl sulfone, tetrahydrothiopyranylsulfone, 1,3-dioxolanyl, tetrahydro-1,1-dioxothienyl, dioxanyl, thietanyl, thiiranyl, triazolinyl, triazolidinyl, etc.

Exemplary bicyclic heterocyclo groups include indolinyl, quinuclidinyl, tetrahydroisoquinolinyl, benzimidazolinyl, chromanyl, dihydrobenzofuran, dihydrofuro[3,4-b]pyridinyl, dihydroisoindolyl, dihydroquinazolinyl (such as 3,4-dihydro-4-oxo-quinazolinyl), benzofurazanyl, benzotriazolinyl, dihydrobenzofuryl, dihydrobenzothienyl, dihydrobenzothiopyranyl, dihydrobenzothiopyranyl sulfone, dihydrobenzopyranyl, isoindolinyl, isochromanyl, benzodioxolyl, tetrahydroquinolinyl, etc.

Exemplary spirocyclic heterocyclo groups include 1-aza[4.5]spirodecane, 2-aza[4.5]spirodecane, 1-aza[5.5]spiroundecane, 2-aza[5.5]spiroundecane, 3-aza[5.5]spiroundecane, etc.

The term "heteroaryl" refers to aromatic 5 or 6 membered monocyclic groups and 9 or 10 membered bicyclic groups which have at least one heteroatom (O, S or N) in at least one of the rings. Each ring of the heteroaryl group containing a heteroatom can contain one or two O and S atoms and/or from one to four N atoms, provided that the total number of heteroatoms in each ring is four or less. The bicyclic heteroaryl rings are formed by fusing a cycloalkyl, substituted cycloalkyl, aryl, substituted aryl, heterocyclo, substituted heterocyclo, heteroaryl or substituted heteroaryl group to the monocyclic heteroaryl ring as defined above. The heteroaryl group is attached via an available carbon or nitrogen atom in the aromatic heteroaryl ring. The nitrogen and sulfur atoms may optionally be oxidized and the nitrogen atoms may optionally be quaternized.

The term "substituted heteroaryl" refers to a heteroaryl ring or ring system as defined above having one, two or three substituents on available carbon or nitrogen atom(s) selected from the group consisting of halogen, nitro, alkyl, substituted alkyl, alkenyl, cyano, cycloalkyl, aryl, heterocyclo, heteroaryl, —$OR^5$, —$CO_2R^5$, —$C(=O)NR^6R^{6a}$, —$OC(=O)R^5$, —$OC(=O)OR^5$, —$OC(=O)NR^6R^{6a}$, —$OCH_2CO_2R^5$, —$C(=O)R^5$, $NR^6R^{6a}$, —$NR^{10}C(=O)R^5$, —$NR^{10}C(=O)OR^5$, —$NR^{10}C(=)C(=O)R^5$, —$NR^{10}C(=O)C(=O)NR^6R^{6a}$, —$NR^{10}C(=O)C(=O)$alkyl, —$NR^{10}C(NCN)OR^5$, $NR^{10}C(=O)NR^6R^{6a}NR^{10}C(NCN)NR^6R^{6a}$, —$NR^{10}C(NR^{11})NR^6R^{6a}$, —$NR^{10}SO_2NR^6R^{6a}$, —$NR^{10}SO_2R^5$, —$SR^5$, —$S(O)R^5$, —$SO_2R^5$, —$SO_3R^5$, —$SO_2NR^6R^{6a}$, —$NHOR^5$, —$NR^{10}NR^6R^{6a}$, —$N[C(=O)R^5][OR^{10}]$, —$N(CO_2R^5)OR^{10}$, —$C(=O)NR^{10}(CR^{12}R^{13})_rR^5$, —$C(=O)(CR^{12}R^{13})_pO(CR^{14}R^{15})_qCO_2R^5$, —$C(=O)(CR^{12}R^{13})_rOR^5$, —$C(=O)(CR^{12}R^{13})_pO(CR^{14}R^{15})_rR^5$, —$C(=O)(CR^{12}R^{13})_rNR^6R^{6a}$, —$OC(=O)O(CR^{12}R^{13})_mNR^6R^{6a}$, —$OC(=O)N(CR^{12}R^{13})_rR^5$, —$O(CR^{12}R^{13})_mNR^6R^{6a}$, —$NR^{10}C(=O)(CR^{12}R^{13})_rR^5$, —$NR^{10}C(=O)(CR^{12}R^{13})_rOR^5$, —$NR^{10}C(=NC)(CR^{12}R^{13})_rR^5$, —$NR^{10}C(=O)(CR^{12}R^{13})_rNR^6R^{6a}$, —$NR^{10}(CR^{12}R^{13})_mOR^5$, —$NR^{10}(CR^{12}R^{13})_rCO_2R^5$, —$NR^{10}(CR^{12}R^{13})_mNR^6R^{6a}$, —$NR^{10}(CR^{12}R^{13})_nSO_2(CR^{14}R^{15})_qR^5$, —$C(=O)NR^{10}(CR^{12}R^{13})_nSO_2(CR^{14}R^{15})_qR^5$, —$SO_2NR^{10}(CR^{12}R^{13})_nCO(CR^{14}R^{15})_qR^5$, —$SO_2NR^{10}(CR^{12}R^{13})_mOR^5$, and —$SO_2NR^{10}(CR^{12}R^{13})_nSi$(alkyl)$_3$.

When a substituted heteroaryl is substituted with a second ring, including an aryl, cycloalkyl, or heterocyclo ring, or a second heteroaryl ring, said second ring in turn is optionally substituted with one to three $R^{16}$ groups as defined below.

Exemplary monocyclic heteroaryl groups include pyrrolyl, pyrazolyl, imidazolyl, oxazolyl, isoxazolyl, thiazolyl, thiadiazolyl, isothiazolyl, pyridinyl, furyl, thienyl, oxadiazolyl, 2-oxazepinyl, azepinyl, pyrazinyl, pyrimidinyl, pyridazinyl, triazinyl, triazolyl, etc.

Exemplary bicyclic heteroaryl groups include benzothiazolyl, benzoxazolyl, benzothienyl, benzofuryl, quinolinyl, quinolinyl-N-oxide, isoquinolinyl, benzimidazolyl, benzopyranyl, indolizinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), benzisothiazolyl, benzisoxazolyl, benzodiazinyl, benzothiopyranyl, benzotriazolyl, benzpyrazolyl, naphthyridinyl, phthalazinyl, purinyl, pyridopyridyl, quinazolinyl, thienofuryl, thienopyridyl, thienothienyl, etc.

In the above definitions for substituted alkyl, substituted alkenyl, substituted cycloalkyl, substituted aryl, substituted heterocyclo, and substituted heteroaryl, the groups $R^5$, $R^6$, $R^{6a}$, $R^{10}$, $R^{11}$, $R^{12}$, $R^{13}$, $R^{14}$, $R^{15}$, $R^{16}$, and $R^{17}$, have the definitions set forth below:

$R^5$, $R^{10}$, and $R^{11}$ are independently selected from hydrogen, alkyl, alkenyl, alkynyl, —C(=O)alkyl, —C(=O)cycloalkyl, —C(=O)aryl, —C(=O)heterocyclo, C(=O)heteroaryl, —$CO_2$alkyl, cycloalkyl, aryl, heterocyclo and heteroaryl, wherein each alkyl, cycloalkyl, aryl, heterocyclo, and/or heteroaryl group of each $R^5$, $R^{10}$, and $R^{11}$ in turn is optionally substituted, where valence allows, with one, two or three groups selected from the group $R^{18}$ as defined below;

$R^6$ and $R^{6a}$ are independently selected from hydrogen, alkyl, —C(=O)alkyl, —C(=O)cycloalkyl, —C(=O)aryl, —C(=O)heterocyclo, C(=O)heteroaryl, —$CO_2$alkyl, cycloalkyl, aryl, heterocyclo and heteroaryl, or $R^6$ and $R^{6a}$ taken together with the nitrogen atom to which they are attached complete a heterocyclo or heteroaryl ring, wherein each alkyl, cycloalkyl, aryl, heterocyclo, and/or heteroaryl group of each $R^6$ and $R^{6a}$ (taken alone or together) in turn is optionally substituted, where valence allows, with one, two or three groups selected from the group $R^{16}$ as defined below;

$R^{12}$ and $R^{14}$ are independently selected from hydrogen and alkyl of 1 to 4 carbons;

$R^{13}$ and $R^{15}$ are independently selected from hydrogen, alkyl of 1 to 4 carbons, and alkyl of 1 to 4 carbons substituted with one, two or three $R^{18}$ groups;

$R^{16}$ at each occurrence is independently selected from the group consisting of —$(CH_2)_q$-halo, —$(CH_2)_q$-cyano, —$(CH_2)_q$—$CF_3$, —$(CH_2)_q$—$OR^{19}$, —$(CH_2)_q$—$OCF_3$, —$(CH_2)_q$—$SR^{19}$, —$(CH_2)_q$-nitro, —$(CH_2)_q$—$NR^{19a}R^{19b}$, —$(CH_2)_q$—$NR^{19}$—$(CH_2)_nNR^{19a}R^{19b}$, —$(CH_2)_qNR^{19}$(cycloalkyl), —$(CH_2)_q$—NHC(=O)alkyl, —$(CH_2)_q$—$NHCO_2$(alkyl), —$(CH_2)_q$-cycloalkyl, —$(CH_2)_q$-aryl, —$(CH_2)_q$-heterocyclo, —$(CH_2)_q$-heteroaryl, —$(CH_2)_q$—$CO_2R^{19b}$, —$(CH_2)_q$—S(O)(alkyl), —$(CH_2)_q$—$SO_2$(alkyl), —$(CH_2)_q$—$SO_3$(alkyl), —$(CH_2)_q$—$SO_2NR^{19a}R^{19b}$, —$(CH_2)_q$—C(=O)$NR^{19a}R^{19b}$, and/or —$(CH_2)_q$—C(=O)$R^{19}$;

$R^{17}$ at each occurrence is independently selected from the group consisting of —$(CH_2)_q$-halo, —$(CH_2)_q$-cyano, —$(CH_2)_q$—$CF_3$, —$(CH_2)_q$—$OR^{19}$, —$(CH_2)_q$—$OCF_3$, —$(CH_2)_q$—$SR^{19}$, —$(CH_2)_q$-nitro, oxo(=O), —$(CH_2)_q$—$NR^{19a}R^{19b}$, —$(CH_2)_q$—$NR^{19}$—$(CH_2)_nNR^{19a}R^{19b}$, —$(CH_2)_q$—$NR^{19}$(cycloalkyl), —$(CH_2)_q$—NHC(=O)alkyl, —$(CH_2)_q$—$NHCO_2$(alkyl), —$(CH_2)_q$-cycloalkyl, —$(CH_2)_q$-aryl, —$(CH_2)_q$-heterocyclo, —$(CH_2)_q$-heteroaryl, —$(CH_2)_q$—$CO_2R^{19b}$, —$(CH_2)_q$—S(O)(alkyl), —$(CH_2)_q$—$SO_2$(alkyl), —$(CH_2)_q$—$SO_3$(alkyl), —$(CH_2)_q$—$SO_2NR^{19a}R^{19b}$, —$(CH_2)_q$—C(=O)$NR^{19a}R^{19b}$, and/or —$(CH_2)_q$—C(=O)$R^{19}$;

$R^{18}$ at each occurrence is independently selected from the group consisting of halo, cyano, $CF_3$, OH, O(alkyl), $OCF_3$, SH, S(alkyl), nitro, $NH_2$, NH(alkyl), N(alkyl)$_2$, NH(cycloalkyl), NHC(=O)alkyl, $NHCO_2$(alkyl), cycloalkyl, aryl, heterocyclo, heteroaryl, $CO_2H$, $CO_2$(alkyl), S(O)(alkyl), $SO_2$(alkyl), $SO_3$(alkyl), $SO_2NH_2$, $SO_2NH$(alkyl), $SO_2N$(alkyl)$_2$, C(=O)$NH_2$, C(=O)NH(alkyl), C(=O)N(alkyl)$_2$, C(=O)H, and/or C(=O)(O$_6$alkyl);

$R^{19}$, $R^{19a}$ and $R^{19b}$ are at each occurrence independently selected from hydrogen and alkyl;

m is an integer from 2 to 6;
n is zero or an integer from 1 to 4;
p is an integer from 1 to 3;
q is zero or an integer from 1 to 3; and
r is zero or an integer from 1 to 6.

Preferred Embodiments

According to one aspect of the invention, preferred compounds are those having the formula (Ia):

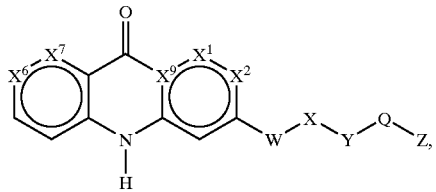

(Ia)

and enantiomers, diastereomers, tautomers, and pharmaceutically acceptable salts and/or solvates thereof, wherein:

$X^1$ is selected from a bond, $CR^1$ and N;
$X^2$ is selected from $CR^{25}$ and N;
$X^6$ is selected from $CR^{25}$ and N; and
$X^7$ is selected from a bond, $CR^1$ and N;
$X^9$ is selected from C and N;
W is —C(=O)—, —S(=O)—, or —S(O)$_2$—; or W may be —CH$_2$— if X is —C(=O)—;
X is selected from —CH$_2$—, —N($R^4$)—, and —O—, except that when W is —CH$_2$—, X is —C(=O)—;
Y is a bond or —C($R^{40}$)($R^{45}$)—;
Q is selected from a bond, —C($R^{26}$)($R^{46}$)—, —C(=O)—, —CH$_2$—O—, —CH$_2$—O—CH$_2$—, —CH$_2$—CO$_2$—NR$^4$—, —CH$_2$—CO$_2$—, —C(=O)NR$^4$—, and —CH=C ($R^{26}$)—;
Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C($R^{40}$)($R^{45}$)— and Q is a bond or —C($R^{26}$)($R^{46}$)—, Z may be $CO_2H$ or $CO_2$alkyl;

$R^1$ is the same or different and is selected from hydrogen, halogen, cyano, alkyl, substituted alkyl, alkenyl, substituted alkenyl, alkynyl, substituted alkynyl, O—$R^7$, —(C=O)$R^7$, —(C=O)—O—$R^7$, $NR^8R^9$, —(C=O)$NR^8R^9$, —$SR^{20}$, —S(=O)$R^{20}$, —SO$_2R^{20}$ and —C≡C—Si(CH$_3$)$_3$;

$R^4$ is selected from H, OH and $C_{1-4}$ alkyl;
$R^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(=O) heterocyclo, —C(=O)—$NR^8R^9$, C(=O)heteroaryl, aryl, substituted aryl, heterocyclo, substituted heterocyclo, heteroaryl and substituted heteroaryl;

$R^8$ and $R^9$ are independently selected from hydrogen, $OR^7$, alkyl, substituted alkyl, cycloalkyl, substituted cycloalkyl, C(=O)alkyl, C(=O)substituted alkyl, C(=O) cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or $R^8$ and $R^9$ are taken together with the nitrogen atom to which they are attached to form a substituted or unsubstituted heterocyclic ring of 3 to 8 atoms, or substituted or unsubstituted heteroaryl ring of 5 atoms;

$R^{20}$ is selected from alkyl and substituted alkyl;
$R^{25}$ is the same or different and is selected from hydrogen, halogen, nitro, cyano, alkyl, substituted alkyl, alkenyl, substituted alkenyl, alkynyl, substituted alkynyl, O—$R^7$, $NR^8R^9$, $SR^7$, $S(O)R^7$, $SO_2R^7$, $SO_3R^7$, $SO_2NR^8R^9$, —C(=O)$R^7CO_2R^7$, C(=O)$NR^8R^9$, and —C≡C—Si(CH$_3$)$_3$;

$R^{26}$ and $R^{46}$ are independently selected from hydrogen, $C_{1-4}$alkyl, hydroxy, halogen, hydroxy$C_{1-4}$alkyl, halo$C_{1-4}$ alkyl, and heterocyclo$C_{1-4}$alkyl, or taken together form a $C_{3-7}$ cycloalkyl ring; and $R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms.

In compounds of formula (I), including those of formula (Ia) as defined above, preferably $R^1$ and $R^{25}$ are selected from hydrogen, halogen, cyano, $C_{1-4}$alkyl, $C_{2-4}$ alkenyl, hydroxy, —O—$C_{1-4}$alkyl, $CF_3$, —O—$CF_3$, C(=O)H, C(=O)$C_{1-4}$alkyl, —(C=O)—OH, —C(=O)O—$C_{1-4}$alkyl, —$NH_2$, —NHC$_{1-4}$alkyl, N($C_{1-4}$alkyl)$_2$, —SH, —S($C_{1-4}$ alkyl), —S(=O)($C_{1-4}$alkyl), —$SO_2NH_2$, —$SO_2NHC_{1-4}$ alkyl, —$SO_2N(C_{1-4}$alkyl)$_2$, and —$SO_2(C_{1-4}$alkyl).

In compounds of formula (I), including those of formula (Ia) as defined above, preferably $R^2$ is hydrogen, —$C_{1-6}$ alkyl, or —$C_{1-4}$alkyl substituted with up to two of cyano, halogen, $CF_3$, —O—$CF_3$, hydroxy, —O—$C_{1-4}$alkyl, NHC$_{1-4}$alkyl, N($C_{1-4}$alkyl)$_2$, —S($C_{1-4}$alkyl), —S(=O)($C_{1-4}$ alkyl), and/or —$SO_2(CO_2(C_{1-4}$alkyl).

In compounds of formula (I), including those of formula (Ia) as defined above, preferably Z is selected from $Z^1$ and $Z^2$, wherein when Y and Q are both a bond, Z is $Z^1$; and when Y is —C($R^{40}$)($R^{45}$)— and Q is selected from a bond, —C($R^{26}$)($R^{46}$)—, —C(=O)—, —CH$_2$—O—, —CH$_2$—O—CH$_2$—, —CH$_2$—CO$_2$—NR$^4$—, —CH$_2$—CO$_2$—, —C(=O)NR$^4$—, and —CH=C($R^{26}$)—, then Z is $Z^2$; $Z^1$ is

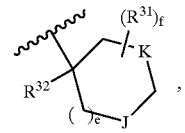

wherein J and K are each independently a bond, O, $NR^{31}$, or —$CHR^{31}$—;

$Z^1$ is selected from
a) $C_{1-6}$alkyl optionally substituted with one to two $R^{31}$;
b) piperidyl, piperazinyl, morpholinyl, or $C_{3-7}$cycloalkyl optionally substituted with one to three $R^{41}$; and
c) phenyl, napthyl, benzocyclopentyl, indolyl, tetrahydroquinolyl, oxazolyl, imidazolyl, thiazolyl, pyridyl, pyridinyl, pyrimidinyl, and pyrazinyl, optionally substituted with one to three $R^{42}$;

$R^4$ is selected from H and $C_{1-4}$ alkyl;

$R^{40}$ and $R^{45}$ are independently selected from hydrogen, cyano, $C_{1-6}$alkyl, and $C_{1-6}$alkyl substituted with hydroxy, or $R^{40}$ and $R^{45}$ are taken together to form a substituted or unsubstituted cycloalkyl ring of 3 to 7 atoms;

$R^{32}$ is selected from cyano, $OR^{34}$, alkyl, substituted alkyl, alkenyl, substituted alkenyl, alkynyl, and substituted alkynyl;

$R^{34}$ is selected from hydrogen, alkyl, and trifluoromethyl;

$R^{31}$ and $R^{41}$ are independently selected from =O, =CH$_2$, halogen, trifluoromethyl, $C_{2-4}$alkenyl, $C_{2-4}$alkynyl, $SR^{60}$, cyano, $S(=O)$alkyl, $SO_2$(alkyl), $CO_2$(alkyl), $SO_2NR^{50}R^{51}$, $NR^{50}R^{51}$, $OR^{60}$; or a group $R^{62}$; or a $C_{1-6}$alkyl optionally substituted with up to two groups selected from $R^{62}$, $NR^{50}R^{51}$, $OR^{60}$, and $SO_2$(alkyl);

$R^{42}$ is at each occurrence independently selected from halogen, trifluoromethyl, $C_{2-4}$alkenyl, $C_{2-4}$alkynyl, S(alkyl), cyano, $S(=O)$alkyl, $SO_2$(alkyl), $CO_2$(alkyl), $SO_2NR^{50}NR^{51}$, $NR^{50}R^{51}$, $OR^{60}$; or a group $R^{62}$; or a $C_{1-6}$alkyl optionally substituted with up to two groups selected from $R^{62}$, $NH_2$, $NH(C_{1-4}$alkyl$)$, $N(C_{1-4}$alkyl$)_2$, $OR^{60}$, and $SO_2$(alkyl);

$R^{50}$ and $R^{51}$ are independently selected from hydrogen, hydroxy, alkyl, $-(CH_2)_d$-cycloalkyl, $-(CH_2)_d$-heterocyclo, O(alkyl), $O(Si)(C_{1-4}$alkyl$)_3$, or $C_{1-6}$alkyl substituted with O(alkyl), $NH_2$, $NH(C_{1-4}$alkyl$)$, or $N(C_{1-4}$alkyl$)_2$, or $R^{50}$ and $R^{51}$ together form a four to six membered heterocyclo ring, wherein when $R^{50}$ or $R^{51}$ is a heterocyclo, said heterocyclo in turn is optionally substituted with up to two groups selected from lower alkyl, $NH_2$, $NH(C_{1-4}$alkyl$)$, and/or $N(C_{1-4}$alkyl$)_2$;

$R^{60}$ is selected from hydrogen, alkyl, pyridyl, pyrimidinyl, and $C_{1-6}$alkyl substituted with O(alkyl), $NH_2$, $NH(C_{1-4}$alkyl$)$, $N(C_{1-4}$alkyl$)_2$, or five or six membered heterocyclo, wherein each $R^{60}$ in turn is optionally substituted with up to two groups selected from $C_{1-4}$alkyl, S(alkyl), $NH_2$, $NH(C_{1-4}$alkyl$)$, and/or $N(C_{1-4}$alkyl$)_2$;

$R^{62}$ is selected from phenyl, five to seven membered heterocyclo, or five to six membered heteroaryl, wherein each $R^{62}$ in turn is optionally substituted with one to two groups selected from OH, $SO_2$(alkyl), $CH_2-OH$, $CH_2-OCH_3$, $NHC(=O)CH_3$, $NH_2$, NH ($C_{1-4}$alkyl), and/or $N(C_{1-4}$alkyl$)_2$;

d is 0, 1, 2, 3 or 4;

e is 1, 2, or 3; and f is 0, 1, 2, or 3.

According to another aspect of the invention, there are provided preferred compounds having the formula (Ib):

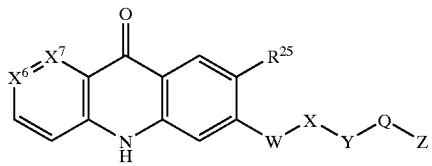

and enantiomers, diastereomers, tautomers, or pharmaceutically acceptable salts or solvates thereof, wherein one of $X^6$ and $X^7$ is N and the other of $X^6$ and $X^7$ is $CR^{25}$, and W, X, Y, Q, Z and $R^{25}$ are as defined above for compounds of formula (Ia).

According to another aspect of the invention, preferred compounds are those having formula (Ib), as defined above, wherein $R^{25}$ is selected from hydrogen, cyano, $-CH_3$, $-CH_2CH_3$, $-OCH_3$, $-SCH_3$, $-S(=O)CH_3$, $-S(O)_2CH_3$, and halogen; the groups W—X taken together are $-C(=O)NR^4-$; Y is $-C(R^{40})(R^{45})$, wherein $R^{40}$ and $R^{45}$ are both methyl, or one of $R^{40}$ and $R^{45}$ is methyl and the other of $R^{40}$ and $R^{45}$ is cyano, or $R^{40}$ and $R^{45}$ together form cyclopropyl, cyclobutyl, or cyclopentyl; and Q and Z are as defined above for compounds of formula (Ia).

Further preferred compounds are those according to formula (Ib), as immediately defined above, wherein Z is lower alkyl, four to nine membered monocyclic or bicyclic heterocyclo or substituted heterocyclo, or phenyl or pyridyl optionally substituted with up to two groups selected from alkyl, substituted alkyl, haloalkyl, halogen, $OR^{27}$, and/or $NR^{28}R^{29}$, wherein $R^{27}$, $R^{28}$, and $R^{29}$ are each independently selected from hydrogen, alkyl, and substituted alkyl.

According to another aspect of the invention, preferred compounds are provided having the following formula (Ic):

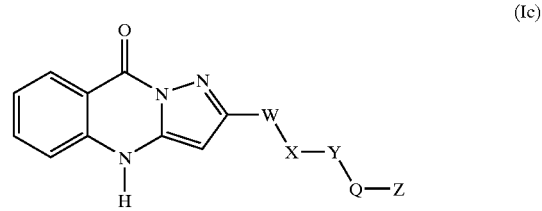

wherein W, X, Y, Q, and Z are as defined above for compounds of formula (Ia) and (Ib).

According to another aspect of the invention, preferred compounds are provided having the above formula (Ic), wherein the groups W—X taken together are $-C(=O)NR^4-$; Y is $-C(R^{40})(R^{45})$, wherein $R^{40}$ and $R^{45}$ are both methyl, or one of $R^{40}$ and $R^{45}$ is methyl and the other of $R^4$ and $R^{45}$ is cyano, or $R^{40}$ and $R^{45}$ together form cyclopropyl, cyclobutyl, or cyclopentyl; and $R^4$ is hydrogen or $C_{1-4}$alkyl.

According to another aspect of the invention, preferred compounds are provided having the following formula (Id):

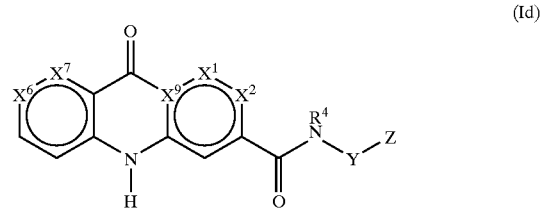

wherein $X^1$ is selected from a bond, $CR^1$ and N;

$X^2$ is selected from $CR^{25}$ and N;

$X^6$ is selected from $CR^{25}$ and N;

$X^7$ is selected from a bond, $CR^1$ and N;

$X^9$ is selected from C and N;

$R^1$ and $R^{25}$ are selected from hydrogen, halogen, cyano, $C_{1-4}$alkyl, $C_{2-4}$alkenyl, hydroxy, $-O-C_{1-4}$alkyl, $CF_3$, $-O-CF_3$, $C(=O)H$, $C(=O)C_{1-4}$alkyl, $-(C=O)-OH$, $-C(=O)O-C_{1-4}$alkyl, $-NH_2$, $-NHC_{1-4}$alkyl, $N(C_{1-4}$alkyl$)_2$, $-SH$, $-S(C_{1-4}$alkyl$)$, $-S(=O)(C_{1-4}$alkyl$)$, $-SO_2NH_2$, $-SO_2NHC_{1-4}$alkyl, $-SO_2N(C_{1-4}$alkyl$)_2$, and $-SO_2(C_{1-4}$alkyl$)$;

$R^4$ is hydrogen or $C_{1-4}$alkyl;

Y is a bond or $-C(R^{40})(R^{45})-$;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl; and $R^{40}$ and $R^{45}$ are both methyl, or one of $R^{40}$ and $R^{45}$ is methyl and the other of $R^{40}$ and $R^{45}$ is cyano, or $R^{40}$ and $R^{45}$ together form cyclopropyl, cyclobutyl, or cyclopentyl.

In compounds of formula (I), including compounds of formulae (Ia), (Ib), (Ic), and (Id), above, preferably W is —C(=O)—.

In compounds of formula (I), including compounds of formulae (Ia), (Ib), (Ic), and (Id), above, preferably Q—Z taken together comprise a group selected from:

$C_{1-4}$alkyl optionally substituted with up to two $R^{31}$;

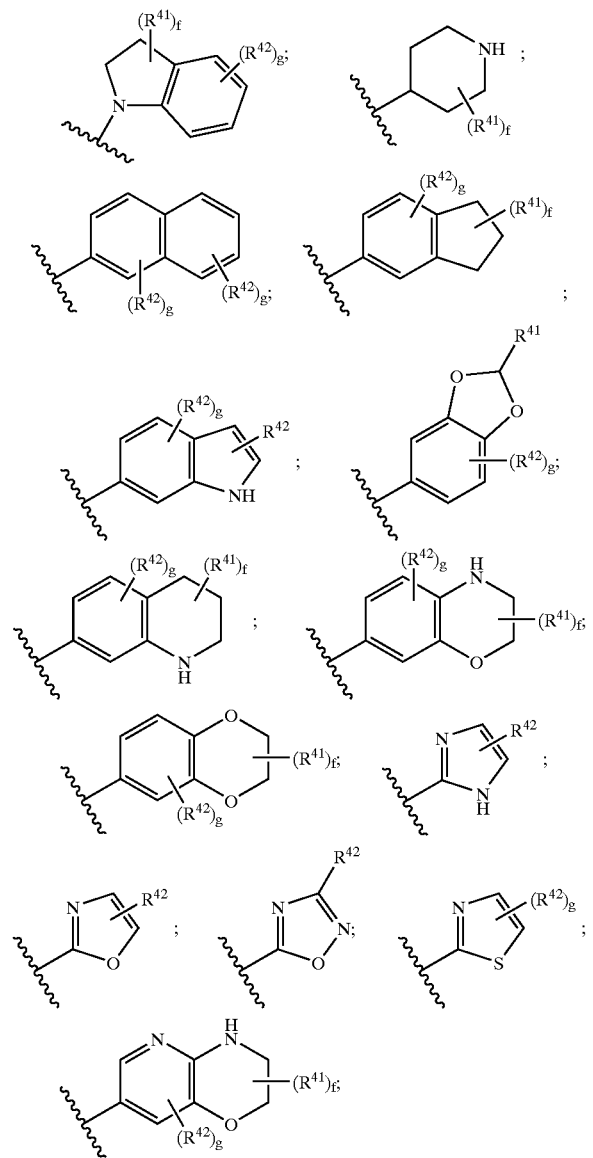

or, Q is selected from a bond, —CH($R^{26}$)—, —CH$_2$—O—, —CH$_2$—O—CH$_2$—, and —CH$_2$—CO$_2$—NH—, and Z is selected from

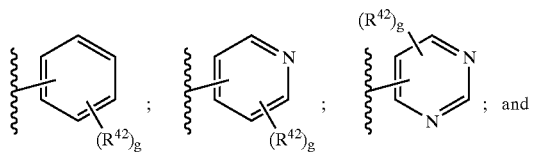

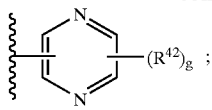

$R^{26}$ is selected from hydrogen, hydroxy, halogen, hydroxy$C_{1-4}$alkyl, and halo$C_{1-4}$alkyl;

$R^{31}$ and $R^{41}$ are at each occurrence independently selected from =O, =CH$_2$, halogen, trifluoromethyl, $C_{2-4}$alkenyl, $C_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$; or a group $R^{62}$; or a $C_{1-6}$alkyl optionally substituted with up to two groups selected from $R^{62}$, NH$_2$, NH($C_{1-4}$alkyl), N($C_{1-4}$alkyl)$_2$, OR$^{60}$, and SO$_2$(alkyl);

R is at each occurrence independently selected from halogen, trifluoromethyl, $C_{2-4}$alkenyl, $C_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$ or a group $R^{62}$; or a $C_{1-6}$alkyl optionally substituted with up to two groups selected from $R^{62}$, NH$_2$, NH($C_{1-4}$alkyl), N($C_{1-4}$alkyl)$_2$, OR$^{60}$, and SO$_2$(alkyl);

$R^{50}$ and $R_{51}$ are independently selected from hydrogen, hydroxy, alkyl, —(CH$_2$)$_d$-cycloalkyl, —(CH$_2$)$_d$-heterocyclo, O(alkyl), O(Si)($C_{1-4}$alkyl)$_3$, or $C_{1-6}$alkyl substituted with O(alkyl), NH$_2$, NH($C_{1-4}$alkyl), or N($C_{1-4}$-alkyl)$_2$, or $R^{50}$ and $R^{51}$ together form a four to six membered heterocyclo ring, wherein when $R^{50}$ or $R^{51}$ is a heterocyclo, said heterocyclo in turn is optionally substituted with lower alkyl, NH$_2$, NH($C_{1-4}$alkyl), or N($C_{1-4}$alkyl)$_2$;

$R^{60}$ is hydrogen, alkyl, pyridyl or pyrimidinyl in turn optionally substituted with $C_{1-4}$alkyl, S(alkyl), NH$_2$, NH($C_{1-4}$alkyl), N($C_{1-4}$alkyl)$_2$, or $C_{1-6}$alkyl substituted with O(alkyl), NH$_2$, NH($C_{1-4}$alkyl), N($C_{1-4}$alkyl)$_2$, or five or six membered heterocyclo;

$R^{62}$ is selected from phenyl, tetrahydrofuryl, azetidinyl, morpholinyl, thiamorpholinyl, piperazinyl, pyrrolidinyl, diazapinyl, seven membered bicyclic heterocyclo having at least one nitrogen atom and zero or one oxygen atom, wherein each $R^{62}$ in turn is optionally substituted with one to two of OH, SO$_2$(alkyl), CH$_2$—OH, CH$_2$—OCH$_3$, NHC(=O)CH$_3$, NH$_2$, NH($C_{1-4}$alkyl), and/or N($C_{1-4}$alkyl)$_2$;

d is 0, 1, or 2;

f is 0, 1, 2 or 3; and g is 0, 1 or 2.

In compounds of formula (I), including compounds of formulae (Ia), (Ib), (Ic), and (Id), above, preferably Z is selected from methyl, ethyl, 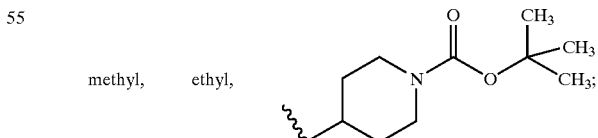

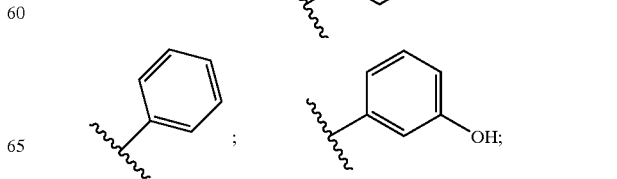

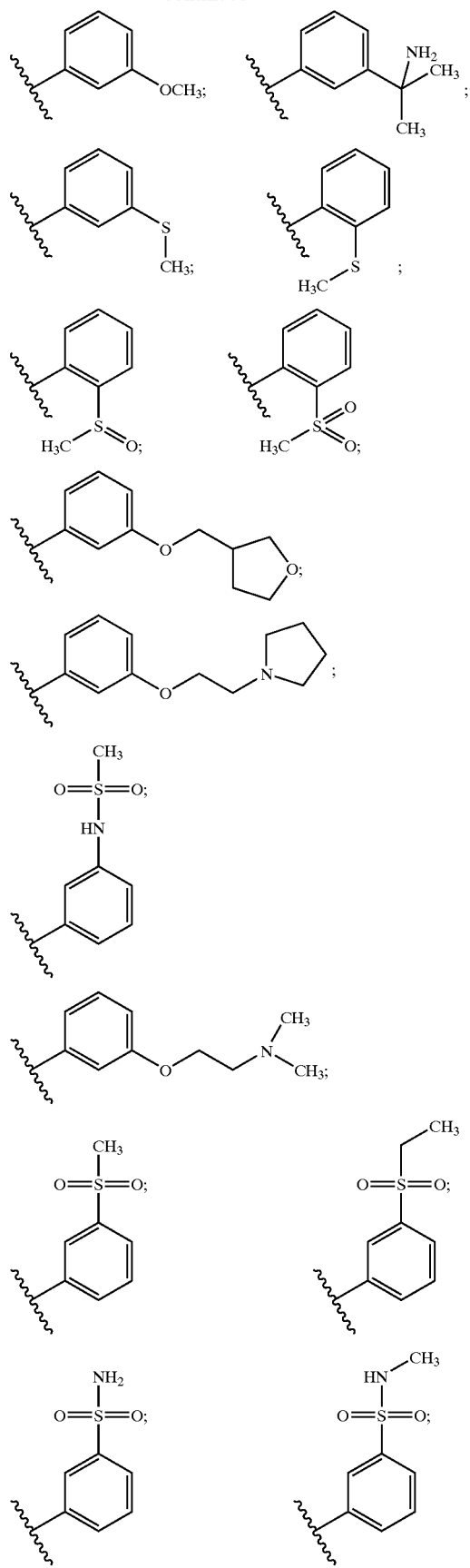
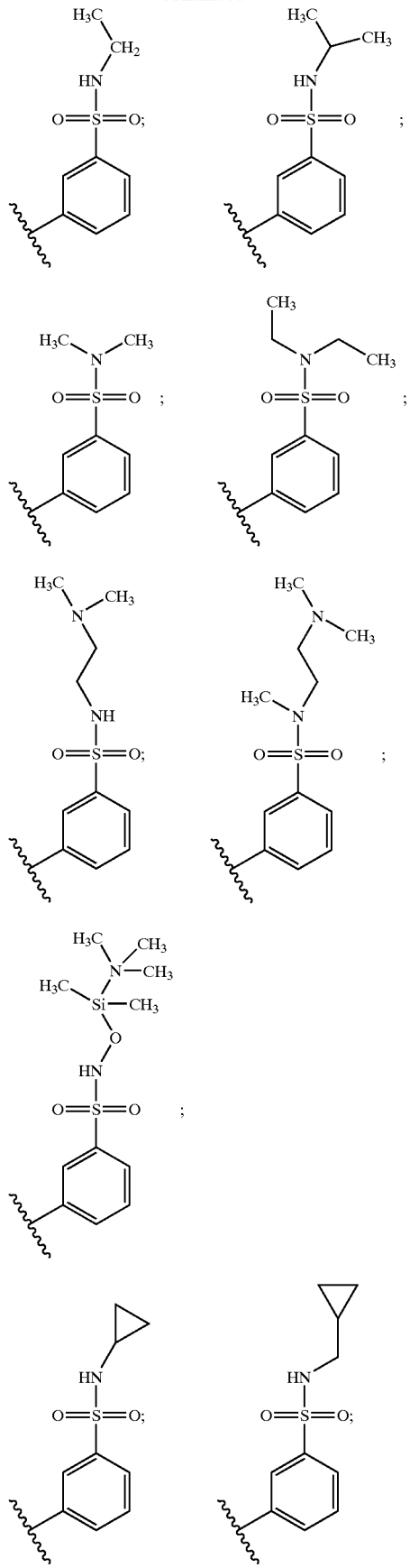

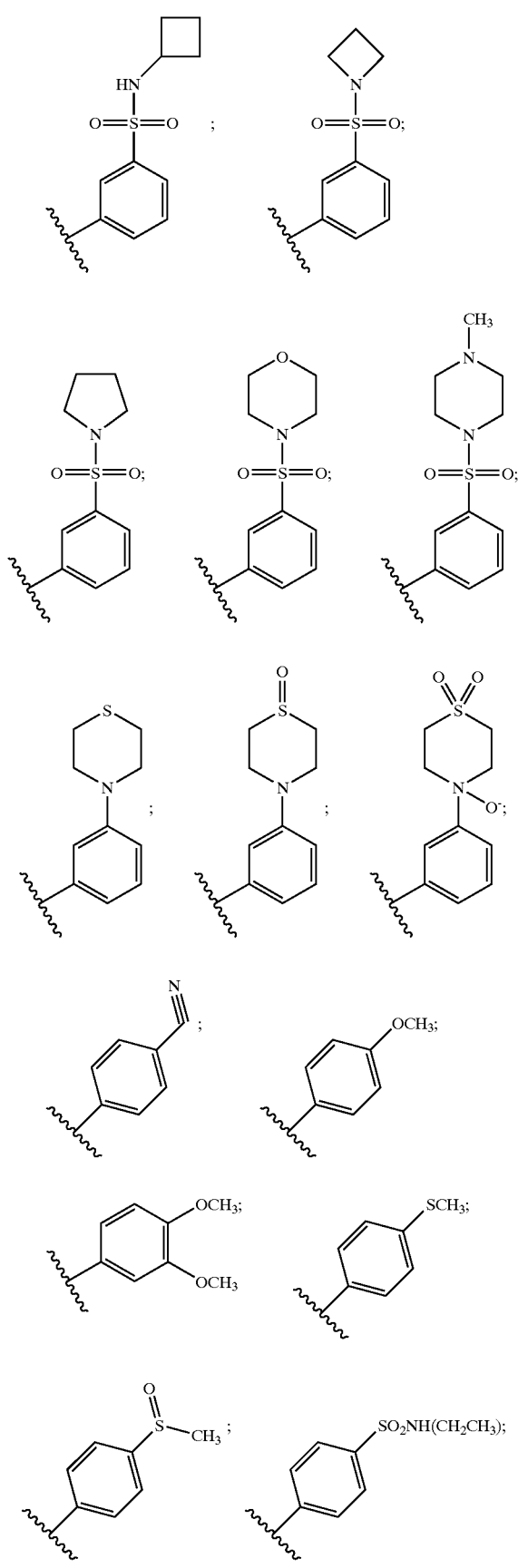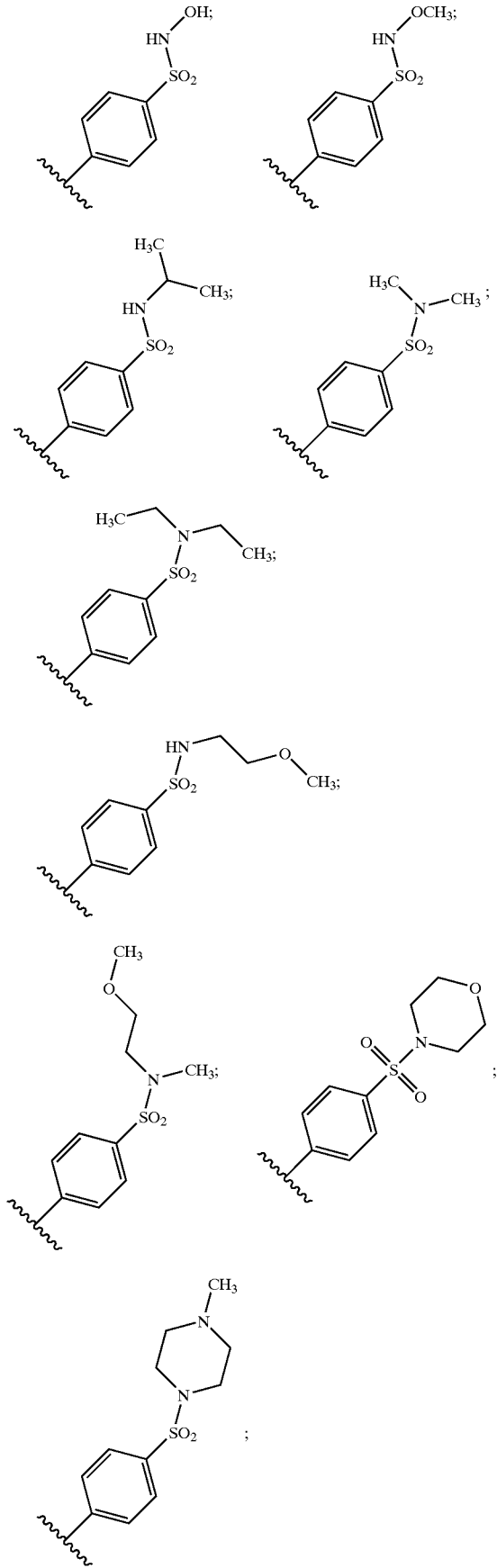

-continued
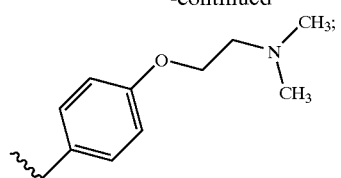
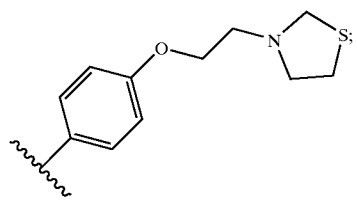
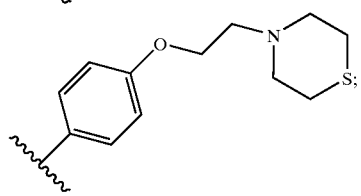
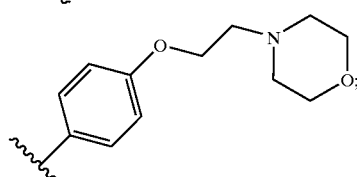
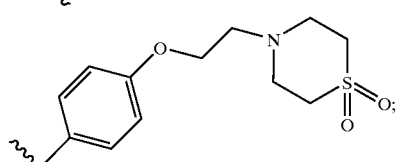
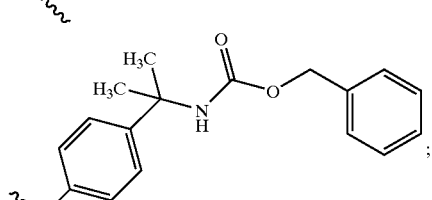
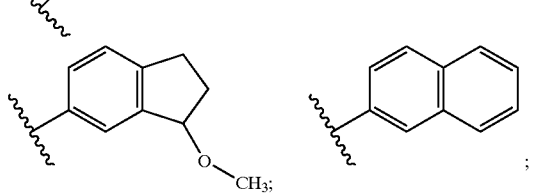
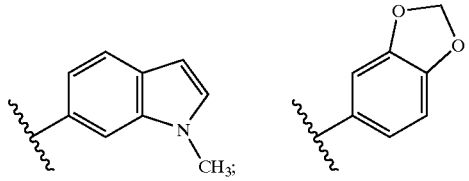
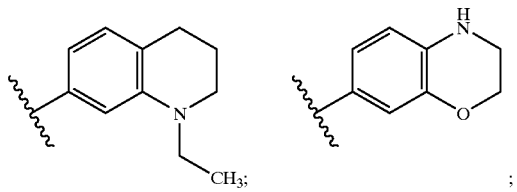
-continued
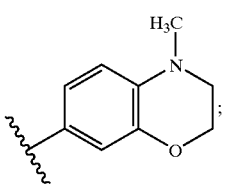 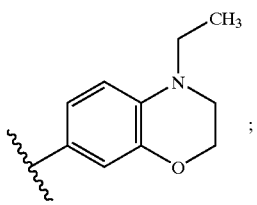
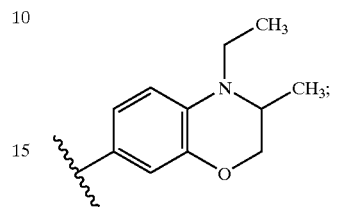 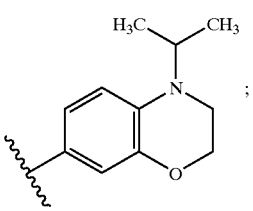
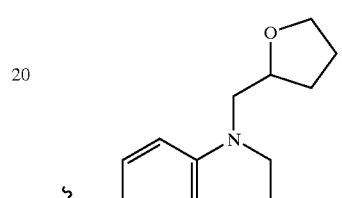 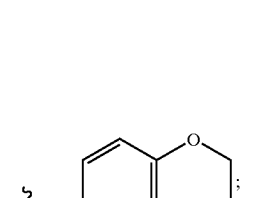
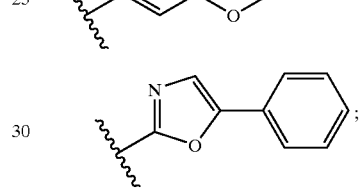
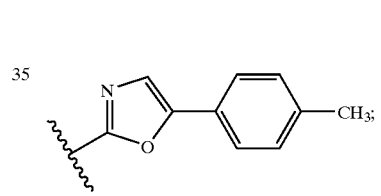 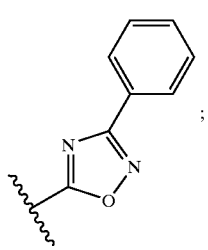
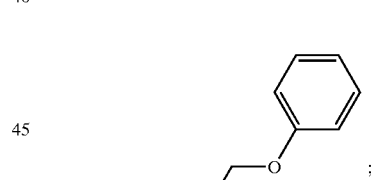
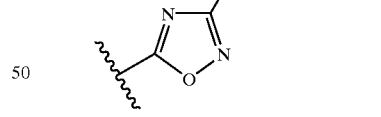
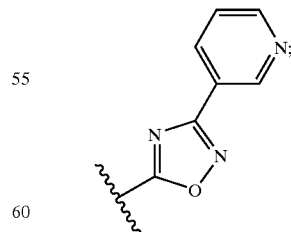
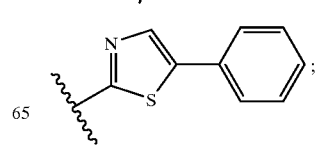 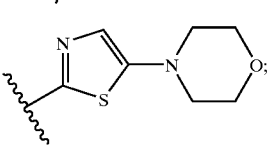

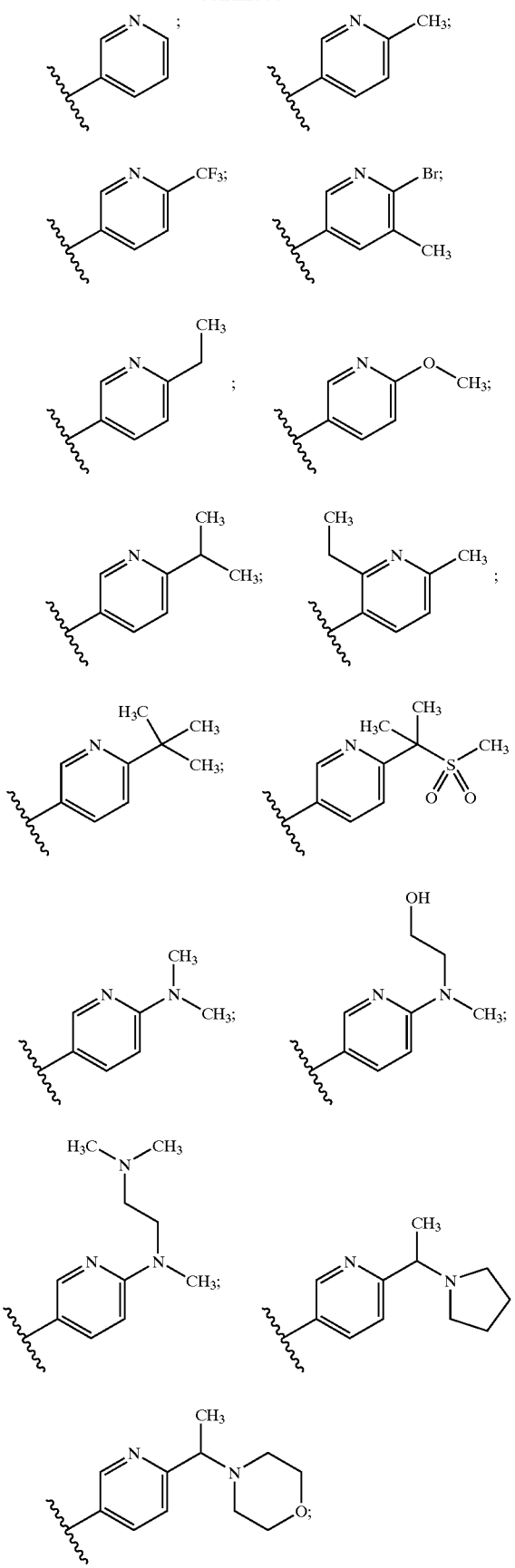
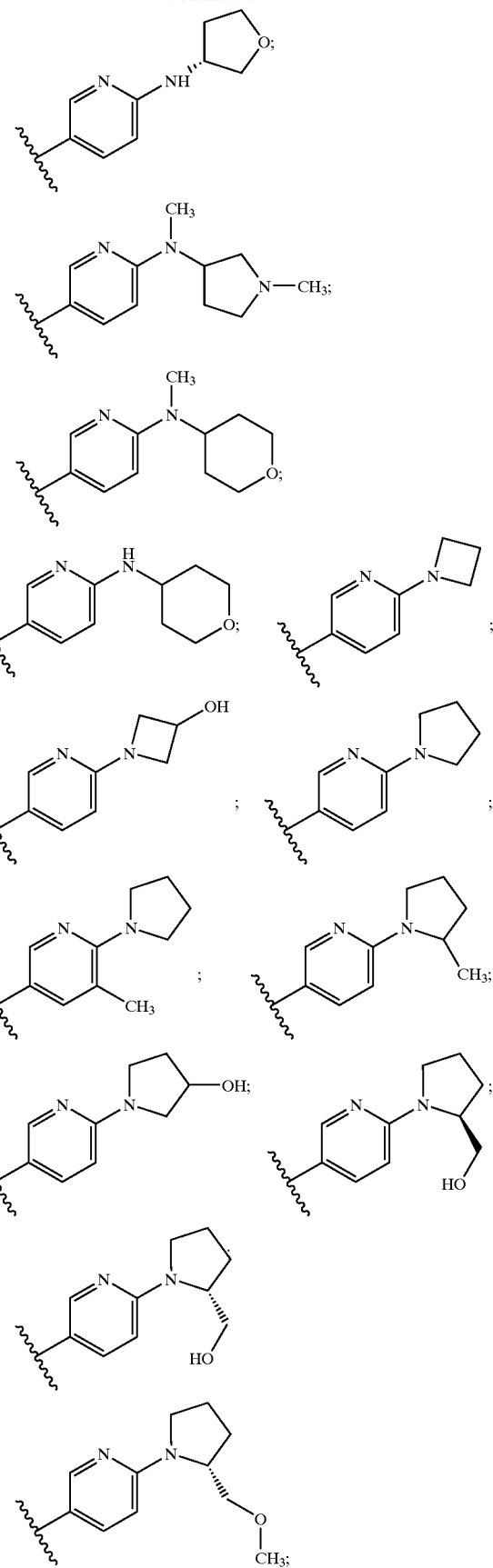

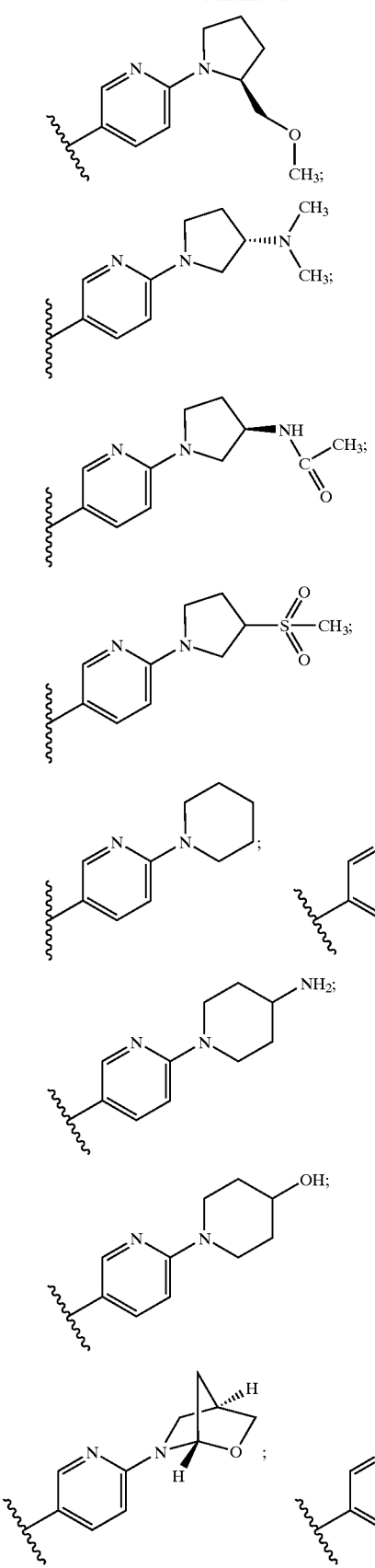
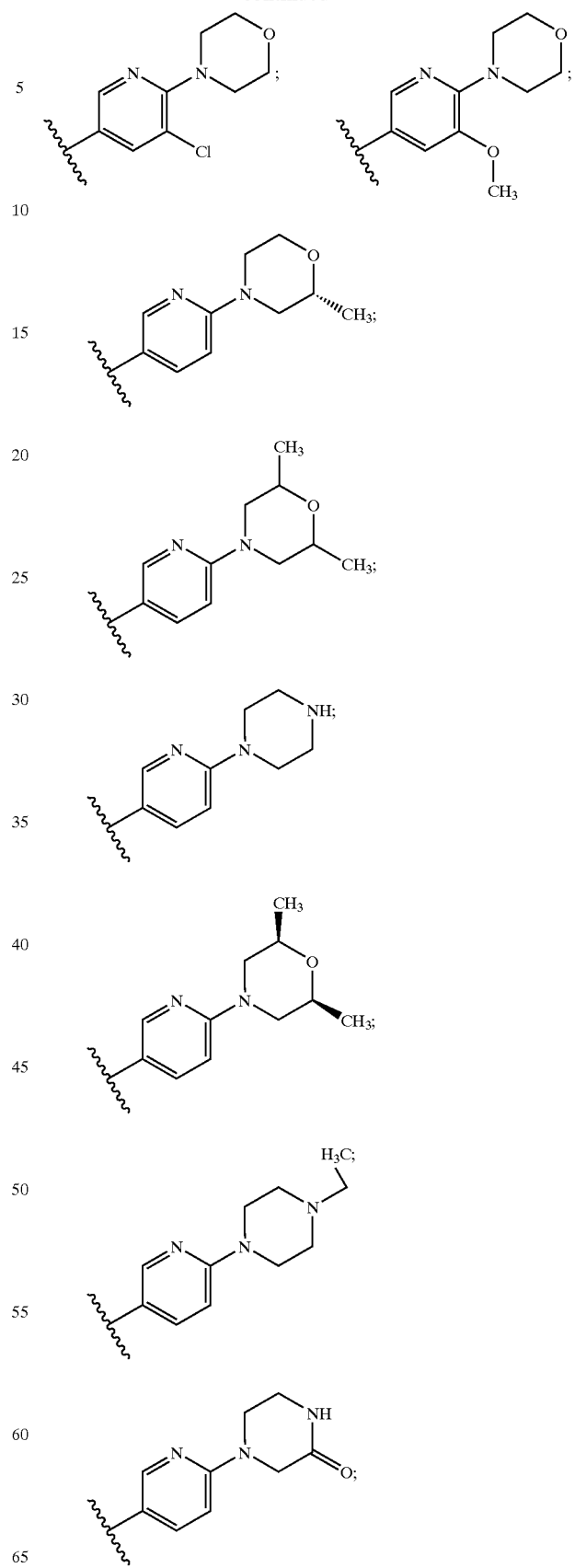

-continued
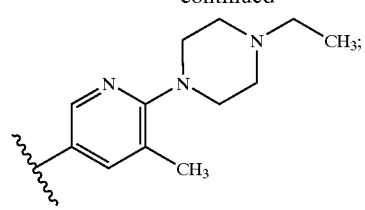
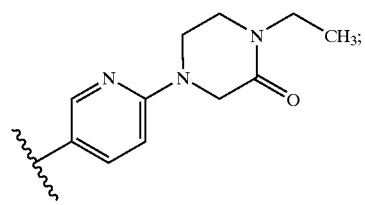
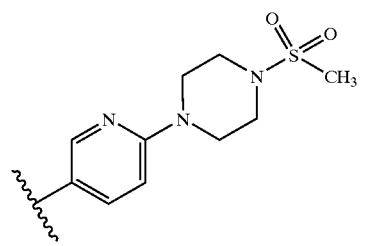
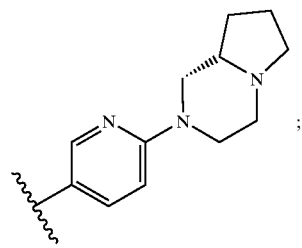
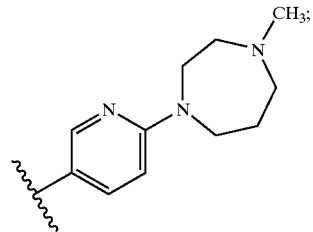
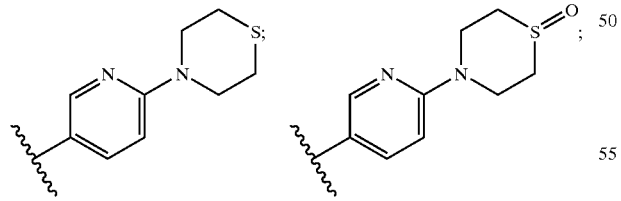
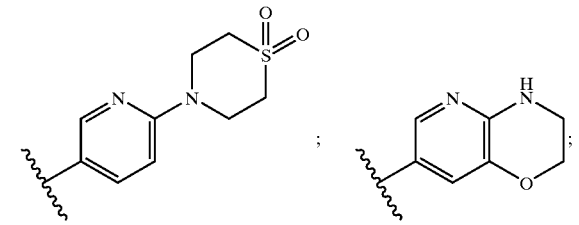
-continued
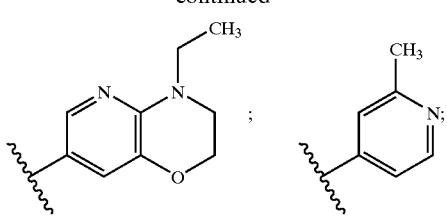
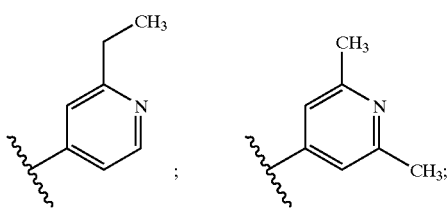
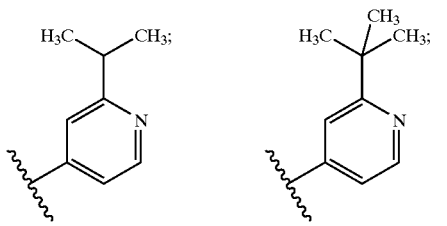
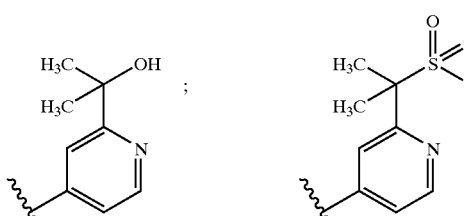
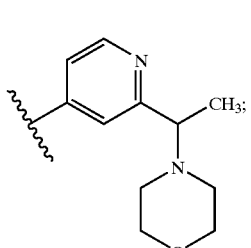
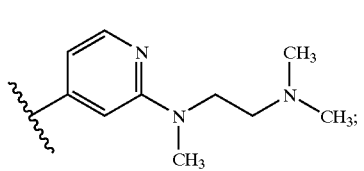
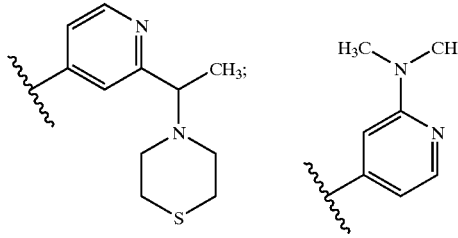

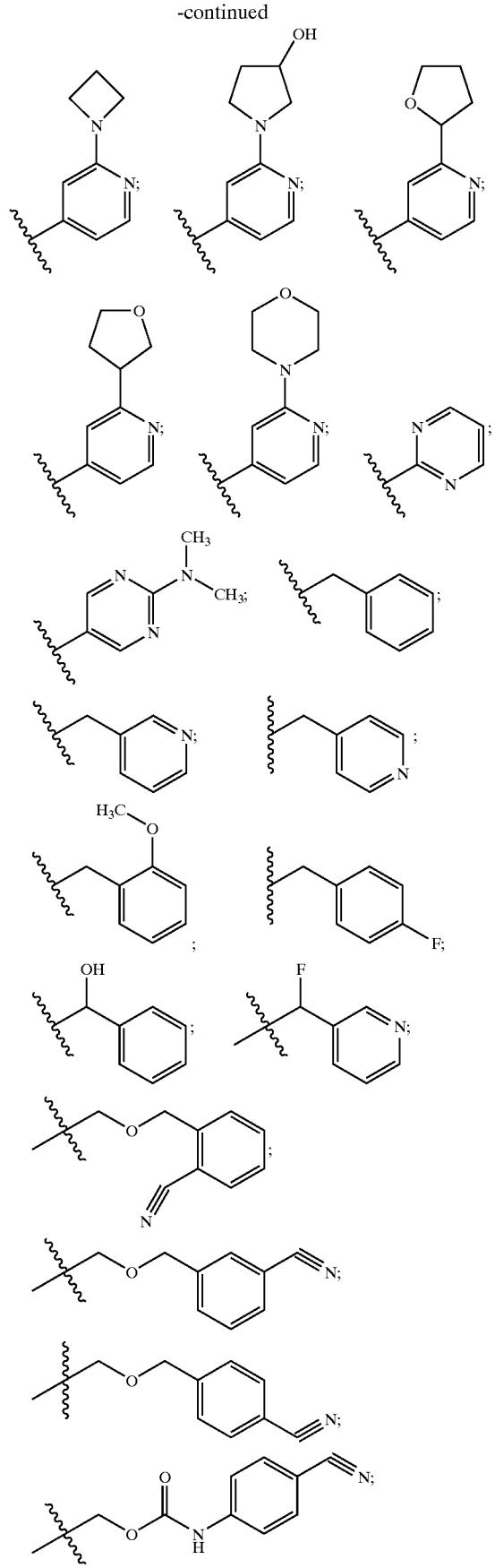
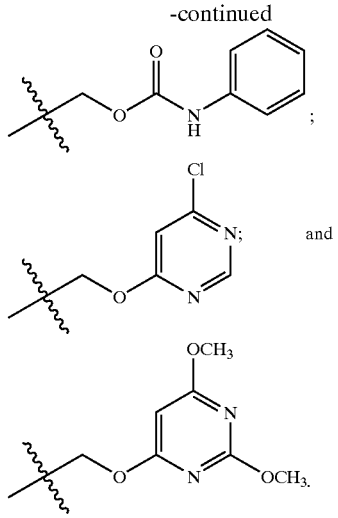
According to another aspect of the invention, in compounds of formula (I), including compounds of formulae (Ia), (Ib), (Ic), and (Id), above, preferably Y is a bond and Z is selected from
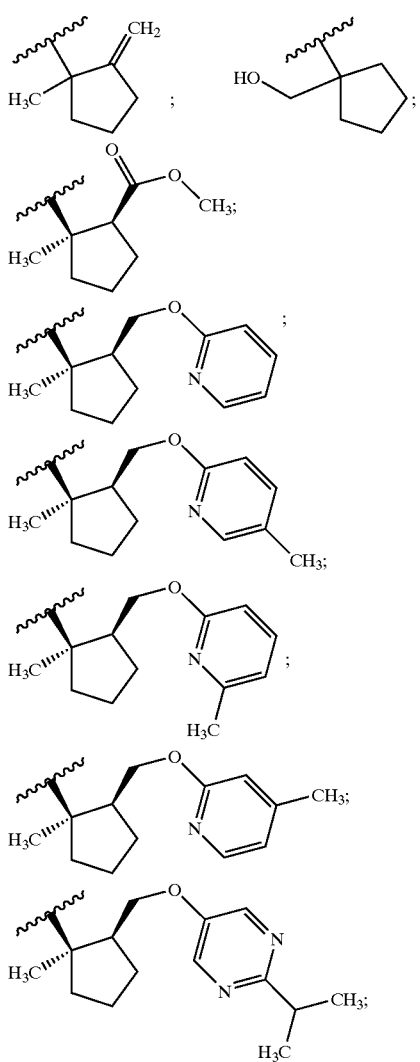

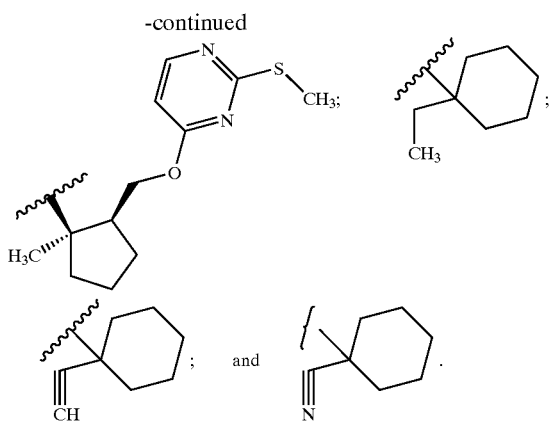

According to another aspect of the invention, preferred compounds are those having Formula (II):

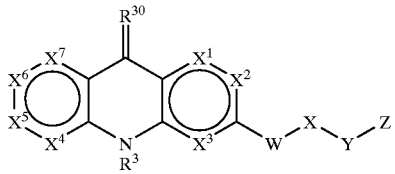

(II)

and enantiomers, diastereomers, tautomers, and pharmaceutically acceptable salts or solvates thereof wherein:

$X^1$ is selected from a bond, $CR^1$ and N;
$X^2$ is selected from $CR^{25}$, N, $NR^2$, O and S;
$X^3$ is selected from $CR^1$, N, $NR^2$, O and S;
$X^4$ is selected from $CR^1$, N, $NR^2$, O and S;
$X^5$ is $CR^1$ or N;
$X^6$ is selected from $CR^{25}$, N, $NR^2$, O, S and substituted heterocycle;
$X^7$ is selected from a bond, $CR^1$ and N;
Provided that $X^1$, $X^2$, $X^3$, $X^4$, $X^5$, $X^6$ and $X^7$ are selected such that an aromatic ring system is formed;
$R^1$ is the same or different and is selected from hydrogen, halogen, cyano, $C_{1-4}$ alkyl, substituted alkyl, alkenyl, substituted alkenyl, alkynyl, substituted alkynyl, O—$R^7$, —(C=O)$R^7$, —(C=O)—O—$R^7$, $NR^8R^9$, —(C=O)$NR^8R^9$, —$SR^{20}$, —S(=O)$R^{20}$, —$SO_2R^{20}$ and —C≡C—Si(CH$_3$)$_3$;
$R^2$ is selected from hydrogen, alkyl and substituted alkyl;
$R^3$ is selected from H, OH and NH$_2$;
$R^4$ is selected from H, OH and $C_{1-4}$ alkyl;
$R^7$ is selected from hydrogen, alkyl, substituted alkyl, alkenyl, alkynyl, cycloalkyl, substituted cycloalkyl, C(O) alkyl, C(O)substituted alkyl, C(O)cycloalkyl, C(O) substituted cycloalkyl, C(O)aryl, C(O)substituted aryl, C(O)O-alkyl, C(O)O-substituted alkyl, C(O)heterocycloalkyl, —C(O)—$NR^8R^9$, C(O)heteroaryl, aryl, substituted aryl, heterocycloalkyl, substituted heterocycloalkyl, heteroaryl and substituted heteroaryl;
$R^8$ and $R^9$ are independently selected from hydrogen, $OR^7$, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O) aryl, C(O)substituted aryl, C(O)O-alkyl, C(O)O-substituted alkyl, C(O)heterocycloalkyl, C(O)heteroaryl, aryl, substituted aryl, heterocycloalkyl, substituted heterocycloalkyl, heteroaryl and substituted heteroaryl, or $R^8$ and $R^9$ are taken together with the nitrogen atom to which they are attached to form a substituted or unsubstituted heterocycloalkyl ring or substituted or unsubstituted heteroaryl ring of 3 to 8 atoms;

$R^{20}$ is selected from alkyl and substituted alkyl;
$R^{25}$ is the same or different and is selected from hydrogen, halogen, nitro, cyano, alkyl, substituted alkyl, alkenyl, substituted alkenyl, alkynyl, substituted alkynyl, O—$R^7$, $NR^8R^9$, $SR^7$, S(O)$R^7$, $SO_2R^7$, $SO_3R^7$, $SO_2NR^8R^9$, $CO_2R^7$, C(O)$NR^8R^9$, C(O)alkyl, C(O)substituted alkyl and —C≡C—Si(CH$_3$)$_3$;
$R^{30}$ is selected from =O and =S;
$R^{40}$ and $R^{45}$ are independently selected from hydrogen, cyano, alkyl, substituted alkyl, cycloalkyl, substituted cycloalkyl, alkenyl, substituted alkenyl, alkynyl, substituted alkynyl, aryl, substituted aryl, heterocycloalkyl, substituted heterocycloalkyl, heteroaryl and substituted heteroaryl, or $R^{40}$ and $R^{45}$ taken together form a substituted or unsubstituted cycloalkyl ring of 3 to 8 atoms or a substituted or unsubstituted heterocycloalkyl ring of 3 to 8 atoms;
W is selected from —CH$_2$, —C=O, $NR^4$, SO and SO$_2$;
X is selected from —CH$_2$, C=O, —O—, $NHR^4$, and $NR^4$;
when W is CH$_2$, X is not CH$_2$;
Y is a bond or C($R^{40}$)($R^{45}$); and
Z is selected from alkyl, substituted alkyl, alkenyl, substituted alkenyl, alkynyl, substituted alkynyl, alkoxy cycloalkyl, substituted cycloalkyl, aryl, substituted aryl, heteroaryl, substituted heteroaryl, heterocyclyl and substituted heterocyclyl.

Further preferred compounds are those having the formula (II), above, wherein:

$X^1$ is selected from a bond, $CR^1$ and N;
$X^2$ is selected from $CR^{25}$ and N;
$X^3$ is $CR^1$;
$X^4$ is $CR^1$;
$X^5$ is $CR^1$;
$X^6$ is selected from $CR^{25}$ and N;
$X^7$ is selected from a bond, $CR^1$ and N;
Provided that $X^1$, $X^2$, $X^3$, $X^4$, $X^5$, $X^6$ and $X^7$ are selected such that an aromatic ring system is formed;
$R^1$ is the same or different and is selected from hydrogen, halogen, cyano, $C_{1-4}$ alkyl, substituted $C_{1-4}$ alkyl, O—$R^7$, —(C=O)$R^7$, —(C=O)—O—$R^7$, $NR^8R^9$, —(C=O) $NR^8R^9$, —$SR^{20}$, —S(=O)$R^{20}$, —$SO_2R^{20}$ and —C≡C—Si (CH$_3$)$_3$;
$R^3$ is H;
$R^4$ is selected from H and $C_{1-4}$ alkyl;
$R^7$, $R^8$, and $R^9$ are selected from hydrogen and $C_{1-4}$ alkyl;
$R^{20}$ is selected from $C_{1-4}$alkyl and substituted $C_{1-4}$alkyl;
$R^{25}$ is the same or different and is selected from hydrogen, halogen, cyano, $C_{1-4}$alkyl, substituted $C_{1-4}$alkyl, O—$R^7$, $NR^8R^9$, $SR^7$, S(O)$R^7$, $SO_2R^7$, $SO_3R^7$, $SO_2NR^8R^9$, $CO_2R^7$, C(O)$NR^8R^9$, C(O)alkyl, C(O) substituted alkyl and —C≡C—Si(CH$_3$)$_3$;
$R^{30}$ is =O;
$R^{40}$ and $R^{45}$ are independently selected from hydrogen, $C_{1-4}$alkyl, and substituted $C_{1-4}$alkyl, or $R^{40}$ and $R^{45}$ taken together form a substituted or unsubstituted cycloalkyl ring of 3 to 7 atoms;
W is selected from —CH$_2$ and —C=O;
X is selected from —CH$_2$, C=O, $NHR^4$, and $NR^4$;
when W is CH$_2$, X is not CH$_2$;
Y is a bond or C($R^{40}$) ($R^{45}$); and
Z is selected from $C_{1-4}$alkyl, substituted $C_{1-4}$alkyl, cycloalkyl, substituted cycloalkyl, aryl, substituted aryl, heteroaryl, substituted heteroaryl, heterocyclyl and substituted heterocyclyl.

Utility

The compounds of the present invention inhibit IMPDH enzyme and are thus useful in the treatment of disorders which are affected by cells that are sensitive to IMPDH inhibition. The present invention thus provides methods for the treatment of IMPDH-associated disorders, comprising administering to a subject in need thereof at least one compound of Formula (I) in an amount effective therefor. As used herein, the term "treating" includes both prophylactic and therapeutic (responsive) uses and thus includes the alleviation of symptoms of an IMPDH-associated condition in a patient, the improvement of an ascertainable measurement associated with such a condition, or the prevention of such a condition or its symptoms. The term "patient" refers to a mammal, preferably a human.

In view of the inventive compounds' activity in inhibiting the IMPDH enzyme, the compounds may be used to treat hyperproliferative diseases and conditions. Below are non-limiting examples of particular diseases and conditions the inventive compounds may be used to treat.

The compounds of the present invention may be used to treat transplant rejection, such as, for example, kidney, liver, heart, lung, pancreas (e.g., islet cells), skin allografts, skin homografts (such as employed in burn treatment), bone marrow, small bowel and/or cells derived from any of these organs. The inventive compounds also may be used to treat conditions associated with and/or developed as a consequence of transplant rejections, such as, for example, serum sickness, graft vs. host disease, and ischemic or reperfusion injury.

The compounds of the present invention may be used to treat inflammatory and/or autoimmune diseases and conditions, such as rheumatoid arthritis, psoriatic arthritis, multiple sclerosis, diabetes (type 1) inflammatory bowel disease, (such as Crohn's disease and ulcerative colitus), pyoderma gangrenosum, lupus (systemic lupus erythematosis), myasthenia gravis, uveitis, Behcet's or Sjogren's syndrome (dry eyes/mouth), pernicious or immunohemolytic anemia, glomerulonephritis, Guillain-Barre syndrome, osteoarthritis, acute pancreatitis, chronic pancreatitis, and vascular diseases which have an inflammatory and/or a proliferative component such as restenosis, stenosis and atherosclerosis.

The inventive compounds may be used to treat autoimmune endocrine disorders, such as, for example, autoimmune thyroiditis, Grave's disease, Hashimoto's thyroiditis, autoimmune polyglandular syndrome (e.g., Addison's disease), hypoparathyroidism, autoimmune testicular failure, autoimmune ovarian failure, and autoimmune hypopituitarism.

The inventive compounds may be used to treat inflammatory conditions of the skin having internal or external etiology, such as, for example, psoriasis, dermatomyositis, Sezary's syndrome, and mycosis fungiodes; eczema, atopic dermatitis, contact dermatitis, urticaria, seborrhea, scleroderma, morphea, lichen planus, vitiligo (depigmentation of the skin), alopecia areata, autoimmune alopecia, and T-cell mediated hypersensitivity diseases, including contact hypersensitivity, delayed-type hypersensitivity, uticaria, and contact dermatitis (including that due to poison ivy).

The compounds also may be used to treat respiratory allergies and conditions, such as, for example, asthma, pulmonary fibrosis, alveolitis, allergic rhinitis, hayfever, oxygen toxicity, emphysema, chronic bronchitis, gluten-sensitive enteropathy (Celiac disease), acute respiratory distress syndrome (ARDs), and any chronic obstructive pulmonary disease (COPD).

Additionally, the inventive compounds may be used to treat infectious diseases, including viral, bacterial, and fungal infections. For example, the inventive compounds may be used in the treatment of DNA or RNA viral replication diseases, such herpes simplex type 1 (HSV-1), herpes simplex type 2 (HSV-2), hepatitis (including hepatitis B and hepatitis C), cytomegalovirus, Epstein-Barr, and human immunodeficiency virus (HIV).

The inventive compounds may be used in the treatment of cancer and tumor disorders, such as solid tumors, lymphomas and leukemia; the compounds of the present invention are useful in treating tumor growth, as an adjunct to chemotherapy, and for treating cancer, more particularly cancer of the lung, prostate, colon, breast, ovaries, and bone.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the Formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The present invention also provides pharmaceutical compositions comprising at least one of the compounds of Formula I, or a pharmaceutically-acceptable salt thereof, capable of treating an IMPDH-associated disorder in an amount effective therefor, alone or in combination with at least one additional therapeutic agent, and a pharmaceutically acceptable carrier, adjuvant or vehicle. "Additional therapeutic agent" encompasses, but is not limited to, an agent selected from the group consisting of an immunosuppressant, an anti-cancer agent, an anti-viral agent, an anti-inflammatory agent, an anti-fungal agent, an antibiotic, or an anti-vascular hyperproliferative compound. These other therapeutic agent(s) may be administered prior to, simultaneously with, or following the administration of the compound(s) of the present invention.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen, celecoxib, rofecoxib, and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4 and/or B7 agonists/antagonists (LEA29Y), CD40 ligand antagonists, other IMPDH inhibitors (such as mycophenolate [CellCept®] and VX-497 [merimepodib]), methotrexate (FK506), leflunomide, integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG). Exemplary other therapeutic agents also include cyclosporins (e.g., cyclosporin A), antibodies such as anti-ICAM-3, anti-IL-2 receptor (Anti-Tac), CD4 antagonists (e.g., priliximab), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, and fusion proteins constructed from CD40 and/or CD154/gp39 (e.g., CD40Ig and CD8gp39).

The inventive compounds may be used in combination with other agents used to treat respiratory conditions such as asthma, COPD, and allergic rhinitis, such as β-adrenergic agonists (such as albuterol, terbutaline, formoterol, salbutamol, salmeterol, bitolterol, pilbuterol, and. fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); MJ cholinergic antagonists (e.g., Spiriva®), PDE 4 inhibitors (e.g. rolipram, cilomilast, piclamilast, or roflumilast [Airoflo®]), histamine $H_1$ antagonists, Allegra® (hexohenadine), Claritin® (loratidone), and/or Clarinex® (deskratidine).

Examples of suitable antiviral agents for use with the inventive compounds include abacavir, nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, C-11294A, CDC-801, BAY-19-8004, cipamfylline, SCH351591, YM-976, PD-189659, mesiopram, pumafentrine, CDC-998, IC-485, and KW-4490.

In view of their usefulness in treating ischemia (e.g., post-operative), the inventive compounds may be used in combination with agents for inhibiting $F_1F_0$-ATPase, including efrapeptin, oligomycin, autovertin B, azide, and compounds described in U.S. patent application Ser. No. 60/339, 108, filed Dec. 10, 2001 and assigned to the present assignee; -alpha- or beta- adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also, be used with lipid-lowering agents, lipid profile modulators and/or antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, atavastatin or visastatin), squalene synthetase inhibitors, fibrates, bile acid sequestrants (such as questran), niacin and niacin/statin combinations, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760, 246), cholesterol absorption inhibitors, cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The inventive compounds may also be useful in combination with antiangiogenic agents, such as compounds that are inhibitors of VEGF receptors, or in conjunction with antitumor agents such as paclitaxel, adriamycin, epithilones, cisplatin, and carboplatin. Examples of anticancer and other cytotoxic agents that may be used in combination with the inventive compounds include azathiaprine, cyclophosphamide, and epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

Another useful application for the inventive compounds is in methods of inhibiting smooth muscle cell proliferation in a patient and as a coating material in making medical devices, e.g., stent devices, catheters, and other transluminal devices. Methods for coating stents are described in U.S. Pat. Nos. 5,356,433, 5,213,898, 5,049,403, 4,807,784 and 4,565,740, each of which is incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 µl.

Compounds disclosed herein are capable of inhibiting the enzyme IMPDH at a measurable level, under the above-described assay or an assay which can determine an effect of inhibition of the enzyme IMPDH.

METHODS OF PREPARATION

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence to give the desired compound(s). All documents cited herein are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. Methods for preparing heterocycles useful to this invention are described in the literature, including Katritzky, A. R., Rees, C. W. Eds, *Comprehensive Heterocyclic Chemistry, The Structure, Reactions, Synthesis and Uses of Heterocyclic Compounds,* Pergamon Press New York (First edition 1984), and Katritzky, A. R., Rees, C. W. and Scriven, E., F. Eds, *Comprehensive Heterocyclic Chemistry II, A Review of the Literature* 1982–1995: *The Structure, Reactions, Synthesis and Uses of Heterocyclic Compounds,* Pergamon Press New York (1996).

Various methods for the synthesis of acridones and acridone acids have been described in the literature. See, e.g., MacNeil et al., *Synlett,* Vol. 4 (1998), at p. 419; Kato, *Chem. Pharm. Bull.,* Vol. 41 (1993), at p. 445; Rewcastle et al., *J. Med. Chem.,* Vol. 29 (1986), at p. 472; Rewcastle et al., *Synthetic Comm.* (1987), at 309; Horiguchi, et al., *Heterocycles,* Vol. 53 (2000), at 1305; Sharp, et al., WO 98/52923 (1998).

Amines such as anilines or heterocyclic amines, useful for preparing compounds according to the invention may be commercially available or readily prepared by many methods known to one skilled in the art of organic chemistry. For example, such methods are described in Richard C. Larock, *Comprehensive Organic Transformations A Guide to Functional Group Preparation,* pp 385–439 (VCH Publishers, Inc. 1989). Examples include but are not limited to reduction of a nitro group, and reduction of an azide.

A general method for the synthesis of the anilines useful in this invention can be performed by metal catalyzed cross-coupling methods known in the literature. The simplest case is a Suzuki-type cross coupling of an aryl boronic acid or ester with an appropriate bromoheterocycle in the presence of a suitable catalyst such as tetrakis (triphenylphosphine) palladium. (See, e.g., Miyaura et al., *Synth. Comm.* 11(7):513–519 (1981); A. Suzuki et. al., *J. Am. Chem. Soc.* 111:513 (1989); and V. N. Kalinin, *Russ. Chem. Rev.* 60:173 (1991)). After the cross coupling has been performed, the product may be deprotected. The choice of protecting group and the method of removal will be-readily apparent to one skilled in the art of organic chemistry. Such considerations and methods are, for example, described by Greene and Wuts, *Protective Groups in Organic Synthesis,* John Wiley and Sons, Inc., New York, N.Y. ($2^{nd}$ Ed. 1991).

Methods for preparing acridones and amine compounds useful in preparing compounds of the present invention are also described in U.S. patent application Ser. No. 10/324, 306, titled "Acridone Inhibitors of IMPDH Enzyme," having the same assignee as the present invention and filed concomitantly herewith, the entire contents of which is incorporated herein by reference. Said application also claims priority to U.S. patent application Ser. No. 60/343,234, filed Dec. 21, 2001.

Schemes 1, 2, and 3 describe various methods for the synthesis of 10-Oxo-5,10-dihydro-benzo[b][1,6]-naphthyridine-7-carboxylic acid, 9-Oxo-4,9-dihydro-pyrazolo[5,1-b]quinazoline-2-carboxylic acid, and their respective derivatives. Various modifications to these methods may be envisioned by those skilled in the art to achieve similar results to those described below. For example, in Scheme 1, other bases may be used to hydrolyze 1B to give 1C and BOP-Cl may also be substituted by other peptide-coupling reagents to synthesize 1E.

Scheme 1

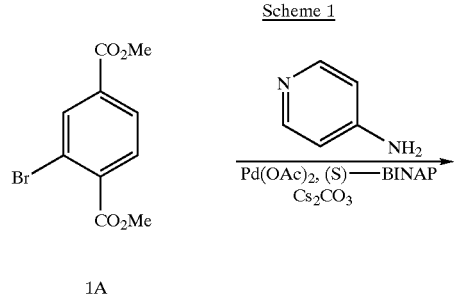

1A

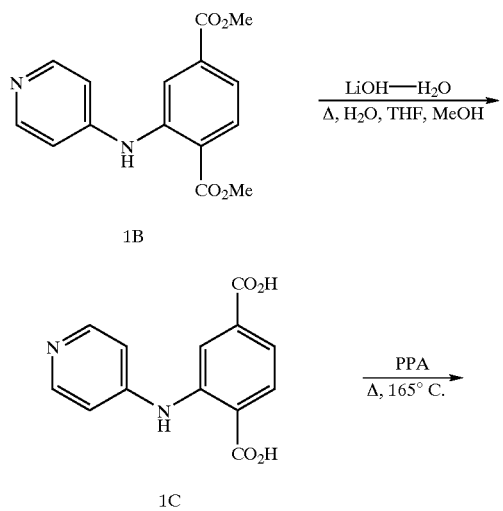

1B

1C

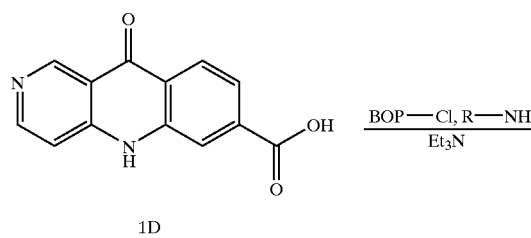

1D

1E

In Scheme 2, reaction of sodium or potassium salt of dialkyl oxaloacetate (R=alkyl, M=Na or K) with 2-aminobenzoyl hydrazide in the presence of a base such as sodium carbonate gives 9-oxo-4,9-dihydro-pyrazolo[5,1-b]quinazoline-2-carboxylic acid 2C. The reaction can be carried out between room temperature to 200° C. for a period of 0.5 to 24 hours. Reaction of 2C with an amine (R'NH$_2$) in the presence of a peptide coupling agent such as BOP-Cl yields 2D.

2-aminobenzoylhydrazides are either commercially available or readily prepared by many methods known to one skilled in the art of organic chemistry and are described in Jerry, "Advanced Organic Chemistry" pages 418 and 423, (March 1992), Wiley Interscience publishers.

Amines of the type RNH$_2$ or R'NH$_2$ are either commercially available or readily prepared by many methods known to one skilled in the art of organic chemistry. Of particular note is the synthesis of a tertiary amine through the conversion of a nitrile group using MeLi/CeCl$_3$.

Scheme 2

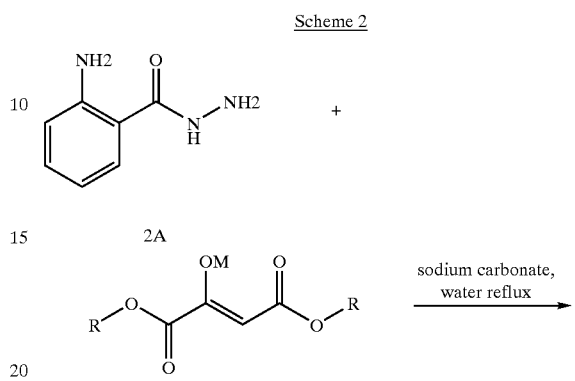

2A

2B

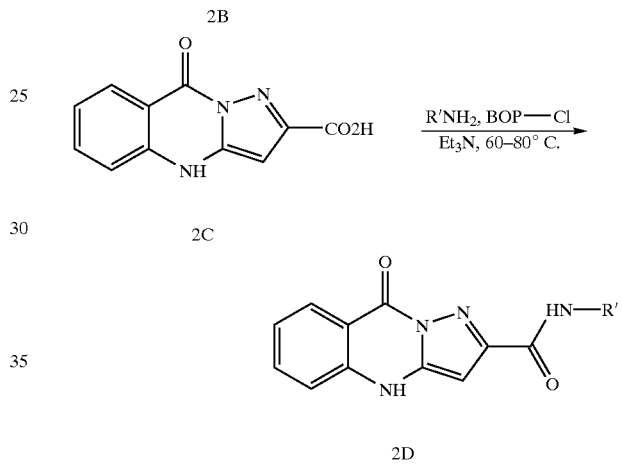

2C

2D

Scheme 3

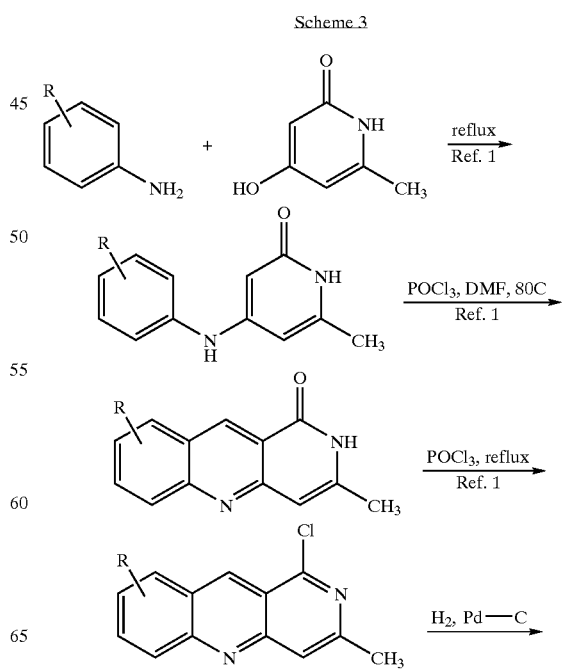

43

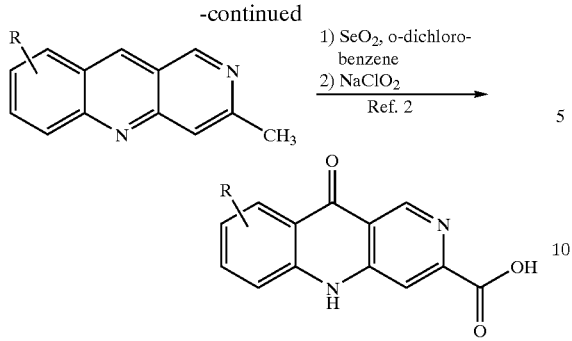

Scheme 3 describes the synthesis of 3-aza-acridone-2-carboxylic acid based on the literature, i.e., Ref. 1: Rivalle, C. and Bisangi E., *J. Heterocycl. Chem.*, Vol. 17 (1980), at pp. 245-248; and Ref. 2: Chen, Q. and Deady, L. W., *Aust. J. Chem.*, Vol. 46 (7) (1993), at pp. 987-993.

Abbreviations

The following abbreviations are used in the Examples herein, for ease of reference.

| | |
|---|---|
| Ac | Acetyl |
| AcOH | Acetic acid |
| aq. | Aqueous |
| CDI | Carbonyldiimidazole |
| Bn | Benzyl |
| Boc | tert-Butoxycarbonyl |
| BOP-Cl | Bis (2-oxo-3-oxazolidinyl)phosphinic chloride |
| DCM | Dichloromethane |
| DMAP | Dimethylaminopyridine |
| DMF | Dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HMPA | Hexamethylphosphoramide |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | Liquid chromatography |
| LDA | Lithium diisopropylamide |
| MCPBA | 3-Chloroperoxybenzoic acid |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | Normal |
| Pd/c | Palladium on carbon |
| Ph | Phenyl |
| PPA | polyphosphoric acid |
| PPTS | Pyridinium p-toluenesulfonate |
| Pr | Propyl |
| p-TsOH | para-Toluenesulonic acid |
| Ret Time | Retention time |
| rt or RT | Room temperature |
| sat. | Saturated |
| TBAF | tetra-n-Butylammonium fluoride |
| TBDMS | t-Butyldimethylsilane |
| TBTU | O-(1H-benzotriazol-1-yl)-N,N,N',N'-tetramethyluronium tetrafluoroborate |
| TBDMSCl | t-Butyldimethylsilyl chlordie |
| THF | Tetrahydrofuran |
| TFA | Trifluoroacetic acid |
| TOSMIC | Tosylmethyl isocyanide |
| YMC | YMC mc, Wilmington, NC 28403 |

44

Abbreviation for HPLC Conditions:

Condition A=YMC ODS column; 4.6×50 mm (4 min. gradient); Solvent A=10% MeOH, 90% H$_2$O, 0.1% TFA; solvent B=90% MeOH, 10% H$_2$O, 0.1% TFA.

EXAMPLES

The invention will now be further described by the following working examples, which are preferred embodiments of the invention. HPLC conditions were as set forth in the above Abbreviations. These examples are illustrative rather than limiting. There may be other embodiments that fall within the spirit and scope of the invention as defined by the appended claims.

Example 1

10-Oxo-5,10-dihydro-benzo[b][1,6]naphthyridine-7-carboxylic acid (1-benzo[1,3]dioxol-5-yl-1-methyl-ethyl)-amide

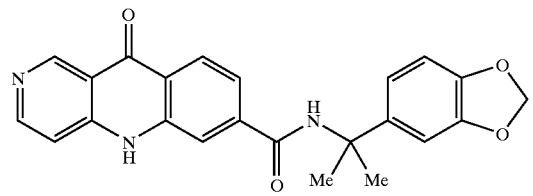

1A

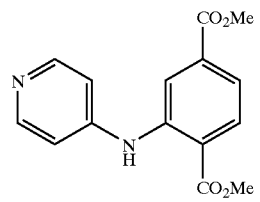

To a mixture of dimethyl bromoterephthalate (2.73 g, 10.0 mmol), 4-aminopyridine (1.13 g, 12.0 mmol), (S)-(−)-2,2'-Bis(diphenylphosphino)-1,1'-binaphthyl (560 mg, 0.90 mmol), and toluene (30 mL) was added cesium carbonate (4.56 g, 14.0 mmol), followed by palladium(II) acetate (0.134 g, 0.6 mmol). The mixture was heated to 100° C. for 24 h. The reaction mixture was cooled to room temperature, diluted with diethyl ether and filtered under reduced pressure through a pad of Celite. The filtrate was concentrated under reduced pressure and purified by silica gel chromatography (hexane-ethyl acetate 7:3 then dichlormethane-ethyl acetate 6:4) to give 0.85 g (30%) of 1A as a light yellow solid. HPLC retention time=1.743 min. (Condition A) and LC/MS $M^++=287^+$. $^1$H-NMR (400 MHz, CDCl$_3$): δ 9.88 (bs, 1H), 8.41 (d, J=6.50, 1H), 8.19 (d, J=1.44, 1H), 8.12 (d, J=8.25, 1H), 7.68 (dd, J=1.44, J=8.25, 1H), 7.15 (d, J=6.50, 1H), 3.96 (s, 3H), 3.95 (s, 3H).

1B.

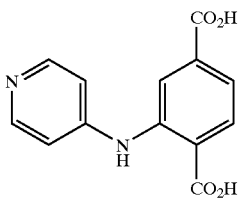

A mixture of 1A (0.84 g, 2.93 mmol) and lithium hydroxide monohydrate (0.37 g, 8.80 mmol) in a 1:1 methanol-THF (10 mL) and water (5 mL) was heated to reflux for 1 h. After cooling, the organic solvents were removed under reduced pressure, and the aqueous residue was diluted with water. The pH was adjusted to 3.5 with 3N aqueous hydrochloric acid. The resulting precipitate was collected by vacuum filtration, rinsed with water and dried under high vacuum to provide 0.79 g (99%) of 1B as a white solid. HPLC retention time=1.19 min. (Column: YMC ODS-A 4.6×50 mm (4 min.); Solvent A=10% MeOH, 90% $H_2O$, 0.1% TFA; Solvent B=90% MeOH, 10% $H_2O$, 0.1% TFA) and a LC/MS $M^+ + 1 = 259^+$.

1C. 10-Oxo-5,10-dihydro-benzo[b][1,6]naphthyridine-7-carboxylic acid

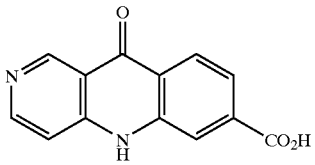

To a round bottom flask containing polyphosphoric acid (7 g) at 165° C. was added finely ground 1B (0.365 g, 1.41 mmol). The reaction mixture was heated to 185–190° C. and stirred for 3.0 h. The mixture was slowly added to iced water and the pH was adjusted to 3.5 with 50% sodium hydroxide. The precipitate was collected by filtration, rinsed with water, and azeotripic evaporated several times with methanol and DCM to give, after drying under high vacuum, 312 g (92%) of 1C as dark brown solid. HPLC retention time=1.544 min. (Condition A) and LC/MS $M^+ + 1 = 241^+$. $^1$H-NMR (400 MHz, DMSO-$d_6$) δ 12.20 (bs, 1H), 9.30 (s, 1H), 8.62 (d, J=1.50 Hz, 1H), 8.32 (d, J=7.80 Hz, 1H), 8.15 (s, 1H), 7.80 (d, J=7.80 Hz, 1H), 7.40 (d, J=1.50, 1H).

1D.

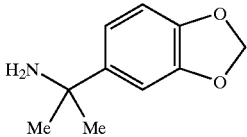

To a flame-dried flask under nitrogen was added cerium chloride (2.47 g, 10.0 mmol), followed by anhydrous THF (20 mL). The mixture was stirred vigorously for 2 h, during which time the cerium chloride became finely suspended. The suspension was cooled to −78° C., and methyl lithium (7.0 mL, 10.0 mmol, 1.4 M in ether) was added dropwise. After the addition was complete, the reaction mixture was stirred for 0.5 h at −78° C. A solution of piperonylonitrile (0.49 g, 3.3 mmol) in THF (3 mL) was added via cannula to the −78° C. solution. The dry-ice bath was removed, and the reaction mixture was stirred at room temperature overnight. The mixture was quenched with a concentrated aqueous ammonium hydroxide (5 mL) and the mixture was stirred vigorously for 1 h. The mixture was filtered through Celite, rinsed with DCM. The combined filtrates were concentrated under reduced, pressure. Further purification using silica gel chromatography ($CH_2Cl_2$-MeOH—$NH_4OH$:95:5:0.5) gave 0.575 g (80%) of compound 1D (HCl salt) as a yellow solid. HPLC retention time=1.203 min. (Condition A) and LC/MS $M^+ + 1 = 182^+$. $^1$H-NMR (400 MHz, DMSO-$d_6$) δ 8.56 (bs, 2H), 7.20 (d, J=1.77, 1H), 6.99 (dd, J=1.77, J=8.20, 1H), 6.95 (d, J=8.20, 1H), 6.04 (s, 2H), 1.59 (s, 6H)

1E.

Example 1

To 1C (48 mg, 0.2 mmol) was sequentially added compound 1D (HCl salt, 86 mg, 0.4 mmol), $Et_3N$ (0.14 mL, 1.0 mmol), anhydrous DMF (1.5 mL), and BOP-Cl (92 mg, 0.36 mmol). The reaction mixture was stirred for 18 h at 50° C., then cooled to room temperature, and concentrated under reduced pressure. The crude residue purified by preparative HPLC on a reversed $C_{18}$ column (YMC ODS column, 100×20 mm, 0–100% gradient over 10 min; Solvent A=10% MeOH, 90% $H_2O$, 0.1% TFA; Solvent B=90% MeOH, 10% $H_2O$, 0.1% TFA) to give Example 1 as a yellow solid. HPLC retention time=2.226 min (Condition A) and LC/MS $M^+ + 1 = 402^+$. $^1$H-NMR (400 MHz, DMSO-$d_6$) δ 12.17 (bs, 1H), 9.30 (s, 1H), 8.72 (s, 1H), 8.62 (d, J=5.87, 1H), 8.29 (d, J=8.40, 1H), 7.90 (s, 1H), 7.73 (d, J =8.40, 1H), 7.43 (d, J=5.87, 1H), 6.97 (s, 1H), 6.88 (dd, J=1.56, J=8.16, 1H), 6.83 (d, J=8.16, 1H), 5.98 (s, 2H), 1.67 (s, 6H).

Example 2

10-Oxo-5,10-dihydro-benzo[b][1,5]naphthyridine-7-carboxylic acid(1-benzo[1,3]dioxol-5-yl-1-methyl-ethyl)-amide

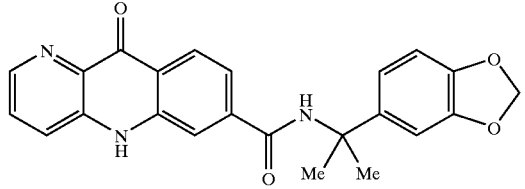

2A. 10-Oxo-5,10-dihydro-benzo[b][1,5]naphthyridine-7-carboxylic acid

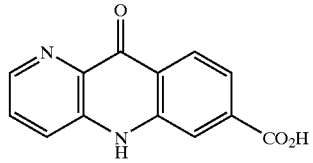

Compound 2A was prepared from dimethyl bromoterephthalate and 3-aminopyridine by a route analogous to that used for the preparation of compound 1C. Compound 2A is a brown solid. HPLC retention time=1.413 min. (Condition A) and LC/MS $M^+ + 1 = 241^+$. $^1$H-NMR (400 MHz, DMSO-d$_6$) δ 12.00 (s, 1H), 8.65 (s, 1H), 8.35 (d, J=8.07 Hz, 1H), 8.19 (s, 1H), 8.02 (d, J=7.52 Hz, 1H), 7.76 (m, 1H).

2B.

Example 2

Using acid 2A and amine 1D and a route analogous to that used for the preparation of example 1, Example 2 was prepared as a yellow solid. HPLC retention time=2.343 min. (Condition A) and LC/MS M$^+$+1=402$^+$. $^1$H-NMR (400 MHz, DMSO-d$_6$) δ 11.99 (bs, 1H), 8.69 (bs, 1H), 8.64 (m, 1H), 8.32 (d, J=8.38, 1H), 8.00 (dd, J=0.82, J=8.53, 1H), 7.92 (s, 1H), 7.74 (dd, J=4.09, J=8.53, 1H), 7.69 (d, J=8.38, 1H), 6.97 (s, 1H), 6.88 (dd, J=1.66, J=8.17, 1H), 6.83 (d, J=8.17, 1H), 5.98 (s, 2H), 1.68 (s, 6H).

Example 3

9-Oxo-4,9-dihydro-pyrazolo[5,1-b]quinazoline-2-carboxylic acid tert-butylamide

3A

A solution of 2-aminobenzoyl hydrazide (2 g, 13.24 mmol) and sodium salt of diethyl oxaloacetate (2.8 g, 13.24 mmol) in water (40 mL) was refluxed for two hours. The reaction mixture was cooled to room temperature, sodium carbonate (1.42 g, 13.24 mmol) was added, and refluxing was continued for two more hours. The reaction mixture was cooled to 0° C. and concentrated hydrochloric acid (2.6 mL, 26.48 mmol) was added. The yellow solid that separated out was filtered and dried to provide compound 3A. Yield: 1.3 g (43%). $^1$H NMR (DMSO-d6): 8.2 (d, 1H), 7.8 (t, 1H), 7.5 (d, 1H), 7.3 (t, 1H), 6.4 (s, 1H).

3B.

Example 3

To compound 3A (40 mg, 0.17 mmol) was sequentially added tert-butylamine (18 μl, 0.17 mmol), Et$_3$N (49 μl, 0.17 mmol), anhydrous DMF (1.0 mL), and BOP-Cl (44 mg, 0.17 mmol). The reaction mixture was stirred at 60° C. for one hour, cooled to room temperature and concentrated under reduced pressure. The crude residue was purified by preparative HPLC on a reversed phase C$_{18}$ column to give Example 3. Yield: 15 mgs (30%). HPLC retention time=2.86 min. (Condition A). M$^+$=285.30.

Example 4

9-Oxo-4,9-dihydro-pyrazolo[5,1-b]quinazoline-2-carboxylic acid (1-methyl-1-phenyl-ethyl)-amide To compound 3A (40 mg, 0.17 mmol) was sequentially added phenylisopropylamine (24 μl, 0.17 mmol), Et$_3$N (49 μg, 0.17 mmol), anhydrous DMF (1.0 mL), and BOP-Cl (44 mg, 0.17 mmol). The reaction mixture was stirred at 80° C. for one hour, cooled to room temperature, and concentrated under reduced pressure. The crude residue was purified by preparative HPLC on a reversed phase C$_{18}$ column to give Example 4. Yield: 25 mgs (41%). HPLC retention time=3.17 min. (Condition A). M$^+$=347.21.

Example 5

To compound 3A (40 mg, 0.17 mmol) was sequentially added 2-(4-fluorobenzyl)propylamine (29 μl, 0.17 mmol), Et$_3$N (49 μl, 0.17 mmol), anhydrous DMF (1.0 mL), and BOP-Cl (44 mg, 0.17 mmol). The reaction mixture was stirred at 80° C. for one hour, cooled to room temperature, and concentrated under reduced pressure. The crude residue was purified by preparative HPLC on a reversed phase C$_{18}$ column to give Example 5. Yield: 17 mgs (26%). HPLC retention time=3.42 min. (Condition A). M$^+$=379.21.

We claim:

1. A compound having the formula, or an enantiomer, diastereomer, tautomer or pharmaceutically acceptable salt, solvate, or prodrug thereof, wherein:

$X^1$ is $CR^1$;

$X^2$ is selected from $CR^{25}$ and N;

$X^6$ is selected from $CR^{25}$ and N;

$X^7$ is $CR^3$;

$X^9$ is C;

Provided, however, that at least one of $X^2$ and $X^6$ is N; and provided further that $X^1$, $X^2$, $X^6$, $X^7$ and $X^9$ are selected such that a tricyclic heteroaryl ring system is formed;

W is —C(=O)—, —S(=O)—, or —S(O)$_2$—;

Y is a bond or —C(R$^{40}$)(R$^{45}$)—;

Q is selected from a bond, —C(R$^{26}$)(R$^{48}$)—, —C(=O)—, —CH$_2$—O—, —CH$_2$—O—CH$_2$—, CO$_2$—NR$^4$—, —CH$_2$—CO$_2$—, —C(=O)NR$^4$—, and —CH=C(R$^{25}$)—;

Z is selected from Z$^1$ and Z$^2$, wherein when Y and Q are both a bond, Z is Z$^1$; and when Y is —C(R$^{40}$)(R$^{46}$)— and Q is selected from a bond, —C(R$^{26}$)(R$^{46}$)—, —C(=O)—, —CH$_2$—O—CH$_2$—, —CH$_2$—CO$_2$—NR$^4$—, —CH$_2$—CO$_2$—, —C(=O)NR$^4$—, and —CH=C(CR$^{28}$)—, then Z is Z$^2$;

Z$^1$ is

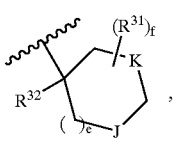

wherein J and K are each independently a bond, O, NR$^{31}$, or —CHR$^{31}$—;

Z$^2$ is selected from a) C$_{1-6}$alkyl optionally substituted with one to two R$^{31}$;

b) piperidyl, piperazinyl, morpholinyl, or C$_{3-7}$cycloalkyl optionally substituted with one to three R$^{41}$; and c) phenyl, napthyl, benzocyclopentyl, indolyl, tetrahydroquinolyl, oxazolyl, imidazolyl, thiazolyl, pyridyl, pyridinyl, pyrimidinyl, and pyrazinyl, optionally substituted with one to three R$^{42}$;

R$^1$ is the same or different and is selected from hydrogen, halogen, cyano, alkyl, substituted alkyl, alkenyl, substituted alkenyl, alkynyl, substituted alkynyl, O—R$^7$, —(C=O)R$^7$, —(C=O)—O—R$^7$, NR$^8$R$^9$, —(C=O)NR$^8$R$^9$, —SR$^{20}$, —S(=O)R$^{20}$, —SO$_2$R$^{20}$ and —C≡C—Si(CH$_3$)$_3$;

R$^4$ is selected from H and C$_{1-4}$ alkyl;

R$^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(=O)heterocyclo, —C(=O)—NR$^8$R$^9$, C(=O)heteroaryl, aryl, substituted aryl, heterocyclo, substituted heterocyclo, heteroaryl and substituted heteroaryl;

R$^8$ and R$^9$ are independently selected from hydrogen, OR$^7$, alkyl, substituted alkyl, cycloalkyl, substituted cycloalkyl, C(=O)alkyl, C(=O)substituted alkyl, C(=O)cycloalkyl. C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or R$^6$ and R$^9$ are taken together with the nitrogen atom to which they are attached to form a substituted or unsubstituted heterocyclic ring of 3 to 8 atoms, or substituted or unsubstituted heteroaryl ring of 5 atoms;

R$^{20}$ is selected from alkyl and substituted alkyl;

R$^{25}$ is the same or different and is selected from hydrogen, halogen, nitro, cyano, alkyl, substituted alkyl, alkenyl, substituted alkenyl, alkynyl, substituted alkynyl, O—R$^7$, NR$^8$R$^9$, SR$^7$, S(O)R$^7$, SO$_2$R$^7$, SO$_3$R$^7$, SO$_2$NR$^8$R$^9$, —C(=O)R$^7$, CO$_2$R$^7$, C(=O)NR$^8$R$^9$, and —C≡C—Si(CH$_3$)$_3$;

R$^{28}$ and R$^{46}$ are independently selected from hydrogen, C$_{1-4}$alkyl, hydroxy, halogen, hydroxyC$_{1-4}$alkyl, haloC$_{1-4}$alkyl, and heterocycloC$_{1-4}$alkyl, or taken together form a C$_{3-7}$ cycloalkyl ring;

R$^{40}$ and R$^{45}$ are independently selected from hydrogen, cyano, C$_{1-8}$alkyl, and C$_{1-8}$alkyl substituted with hydroxy, or R$^{40}$ and R$^{45}$ are taken together to form a substituted or unsubstituted cycloalkyl ring of 3 to 7 atoms;

R$^{32}$ is selected from cyano, OR$^{34}$, alkyl, substituted alkyl, alkenyl, substituted alkenyl, alkynyl, and substituted alkynyl, R$^{34}$ is selected from hydrogen, alkyl, and trifluoromethyl;

R$^{31}$ and R$^{41}$ are independently selected from =O, =CH$_2$, halogen, trifluoromethyl, C$_{2-4}$alkenyl, C$_{2-4}$alkynyl, SR$^{60}$, cyano, S(=O)alkyl, SO$_2$(alkyl), CO$_2$(alkyl), SO$_2$NR$^{50}$R$^{51}$, NR$^{50}$R$^{51}$, OR$^{60}$; or a group R$^{62}$; or a C$_{1-6}$alkyl optionally substituted with up to two groups selected from R$^{62}$, NR$^{50}$R$^{51}$, OR$^{50}$, and SO$_2$(alkyl);

R$^{42}$ is at each occurrence independently selected from halogen, trifluoromethyl, C$_{2-4}$alkenyl, C$_{2-4}$alkynyl, S(alkyl), cyano, S(=O)alkyl, SO$_2$(alkyl), CO$_2$(alkyl), SO$_2$NR$^{50}$R$^{51}$, NR$^{60}$R$^{51}$, OR$^{60}$; or a group R$^{62}$; or a C$_{1-6}$alkyl optionally substituted with up to two groups selected from R$^{62}$, NH$_2$, NH(C$_{1-4}$alkyl), N(C$_{1-4}$alkyl)$_2$, OR$^{60}$, and SO$_2$(alkyl);

R$^{50}$ and R$^{51}$ are independently selected from hydrogen, hydroxy, —(CH$_2$)$_d$-cycloalkyl, —(CH$_2$)$_d$-heterocyclo, O(alkyl), O(SI)(C$_{1-4}$alkyl)$_3$, or R$^{50}$ and R$^{51}$ together form a four to six membered heterocyclo ring, wherein when R$^{50}$ or R$^{51}$ is a heterocyclo, said heterocyclo in turn is optionally substituted with up to two groups selected from lower alkyl, NH$_3$, NH(C$_{1-4}$alkyl), and/or N(C$_{1-4}$alkyl)$_2$;

R$^{60}$ is selected from hydrogen, alkyl, pyridyl, pyrimidinyl, and C$_{1-6}$alkyl substituted with O(alkyl), NH$_2$, NH(C$_{1-4}$alkyl), N(C$_{1-4}$alkyl)$_2$, or five or six membered heterocyclo, wherein each R$^{60}$ in turn is optionally substituted with up to two groups selected from C$_{1-4}$alkyl, S(alkyl), NH$_2$, NH(C$_{1-4}$alkyl), and/or N(C$_{1-4}$ alkyl)$_2$;

R$^{62}$ is selected from phenyl, five to seven membered heterocyclo, or five to six membered heteroaryl, wherein each R$^{62}$ in turn is optionally substituted with one to two groups selected from OH, SO$_2$(alkyl), CH$_2$—OH, CH$_2$—OCH$_3$, NHC(=O)CH$_3$, NH$_2$, NH(C$_{1-4}$alkyl), and/or N(C$_{1-4}$alkyl)$_2$;

d is 0, 1, 2, 3 or 4;

e is 1, 2, or 3; and f is 0, 1, 2, or 3.

2. A compound having the formula,

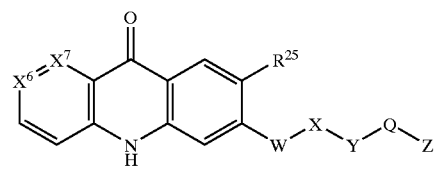

or an enantiomer, diastereomer, tautomer or pharmaceutically acceptable salt, solvate, or prodrug thereof, wherein:

X⁵ is N

X⁷ is CR¹;

W is —C(=O)—, —S(=O)—, or —S(O)₂—; or W may be —CH₂— if X is —C(=O)—, —S(=O)—, or —S(O)₂—;

X is selected from —CH₂—, —N(R⁴)—, and —O—, except that when W is —CH₂, X is selected from —C(=O)—, —S(=O)—, or —S(O)₂—; or the groups W—X taken together are —C(=O)NR⁴—;

Y is —C(R⁴⁰)(R⁴⁵)—;

Q is selected from a bond, —C(R²⁶)(R⁴⁶)—, —C(=O)—, —CH₂—O—, —CH₂—O—CH₂, —CH₂—CO₂—NR⁴—, —CH₂—CO₂—, —C(=O)NR⁴—, and —CH=C(R²⁶)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Q is a bond or —C(R²⁶)(R⁴⁶)—, Z may be CO₂H or CO₂alkyl;

R¹ is the same or different and is selected from hydrogen, halogen, cyano, alkyl, substituted alkyl, alkenyl, substituted alkenyl, alkynyl, substituted alkynyl, O—R⁷, —(C=O)R⁷, —(C=O)—O—R⁷, NR⁸R⁹, —(C=O)NR⁸R⁹, —SR²⁰, —S(=O)R²⁰, —SO₂R²⁰ and —C≡C—Si(CH₃)₃;

R⁴ is selected from H, OH and C₁₋₄alkyl;

R⁷ is selected from hydrogen, alkyl, substituted alkyl, alkenyl, alkynyl, cycloalkyl, substituted cycloalkyl, C(=O)alkyl, C(=O)substituted alkyl, C(=O) cycloalkyl, C(=O) substituted cycloalkyl, C(=O)aryl, C(=O)substituted aryl, C(=O)O-alkyl C(=O)O-substituted alkyl, C(=O)heterocyclo, —C(=O)—NR⁸R⁹, C(=O)heteroaryl, aryl, substituted aryl, heterocyclo, substituted heterocyclo, heteroaryl and substituted heteroaryl;

R⁸ and R⁹ are independently selected from hydrogen, OR⁷, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or R⁸ and R⁹ are taken together with the nitrogen atom to which they are attached to form a substituted or unsubstituted heterocyclic ring of 3 to 8 atoms, or substituted or unsubstituted heteroaryl ring of 5 atoms;

R²⁰ is selected from alkyl and substituted alkyl;

R²⁵ is the same or different and is selected from hydrogen, halogen, nitro, cyano, alkyl, substituted alkyl, alkenyl, substituted alkenyl, alkynyl, substituted alkynyl, O—R⁷, NR⁸R⁹, SR⁷, S(O)R⁷, SO₂R⁷, SO₃R⁷, SO₂NR⁸R⁹, —C(=O)R⁷, CO₂R⁷, C(=O)NR⁸R⁹, and —C≡C—Si(CH₃)₃;

R²⁶ and R⁴⁶ are independently selected from hydrogen, C₁₋₄alkyl, hydroxy, halogen, hydroxyC₁₋₄alkyl, haloC₁₋₄alkyl, and heterocycloC₁₋₄alkyl or taken together form a C₃₋₇cycloalkyl ring; and R⁴⁰ and R⁴⁵ are both methyl, or one of R⁴⁰ and R⁴⁵ is methyl and the other of R⁴⁰ and R⁴⁵ is cyano, or R⁴⁰ and R⁴⁵ together form cyclopropyl, cyclobutyl, or cyclopentyl.

3. A compound having the formula,

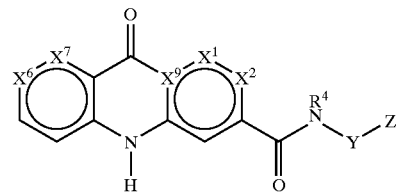

or an enantiomer, diastereomer, tautomer or pharmaceutically acceptable salt, solvate, or prodrug thereof, wherein:

X¹ is CR¹;

X² is selected from CR²⁵ and N;

X⁶ is selected from CR²⁵ and N;

X⁷ is CR¹;

X⁹ is C;

Provided, however, that at least one of X² and X⁶ is N; and provided further that X¹, X², X⁶, X⁷ and X⁹ are selected such that a tricyclic heteroaryl ring system is formed;

Y is —C(R⁴⁰)(R⁴⁵)—;

Z is lower alkyl, heterocyclo, substituted heterocyclo, or phenyl or pyridyl optionally substituted with up to two groups selected from alkyl, substituted alkyl, haloalkyl, halogen OR²⁷, and NR²⁸R²⁹;

R¹ is selected from hydrogen, cyano, —CH₃, —CH₂CH₃, —OCH₃, —SCH₃, —S(=O)CH₃, —S(O)₂CH₃, and halogen;

R⁴ is hydrogen or C₁₋₄alkyl;

R²⁵ is selected from hydrogen, cyano, —CH₃, —CH₂CH₃, —OCH₃, —SCH₃, —S(=O)CH₃, —S(O)₂CH₃, and halogen;

R²⁷, R²⁸, and R²⁹ are each independently selected from hydrogen, alkyl, and substituted alkyl; and R⁴⁰ and R⁴⁵ are both methyl, or one of R⁴⁰ and R⁴⁵ is methyl and the other of R⁴⁰ and R⁴⁵ is cyano, or R⁴⁰ and R⁴⁵ together form cyclopropyl, cyclobutyl, or cyclopentyl.

4. A compound according to claim 2, or an enantiomer, diastereomer, tautomer, or pharmaceutically-acceptable salt, solvate, or prodrug thereof, wherein:

Q—Z taken together comprises a group selected from:

C₁₋₄alkyl optionally substituted with up to two R³¹;

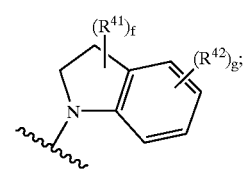 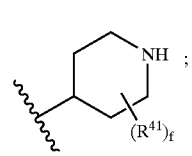

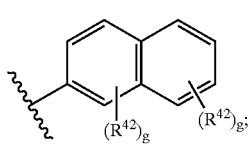 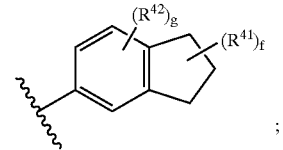

-continued or, Q is selected from a bond, —CH($R^{26}$)—, —CH$_2$—O—, —CH$_2$—O—CH$_2$—, and —CH$_2$—CO$_2$—NH—, and Z is selected from $R^{26}$ is selected from hydrogen, hydroxy, halogen, hydroxyC$_{1-4}$alkyl, and haloC$_{1-4}$alkyl;

$R^{31}$ and $R^{41}$ are at each occurrence independently selected from =O, =CH$_2$, halogen, trifluoromethyl, C$_{2-4}$alkenyl, C$_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$; or a group R$^{62}$; or a C$_{1-6}$alkyl optionally substituted with up to two groups selected from R$^{62}$, NH$_2$, NH(C$_{1-4}$alkyl), N(C$_{1-4}$alkyl)$_2$, OR$^{60}$, and SO$_2$(alkyl);

$R^{42}$ is at each occurrence independently selected from halogen, trifluoromethyl, C$_{2-4}$alkenyl, C$_{2-4}$alkynyl, S(alkyl), cyano, S(=O)alkyl, SO$_2$(alkyl), CO$_2$(alkyl), SO$_2$NR$^{50}$R$^{51}$, NR$^{50}$R$^{51}$, OR$^{60}$ or a group R$^{62}$; or a C$_{1-6}$alkyl optionally substituted with up to two groups selected from R$^{62}$, NH$_2$, NH(C$_{1-4}$alkyl), N(C$_{1-4}$alkyl)$_2$, OR$^{60}$, and SO$_2$(alkyl);

$R^{50}$ and $R^{51}$ are independently selected from hydrogen, hydroxy, alkyl, —(CH$_2$)$_d$-cycloalkyl, —(CH$_2$)$_d$-heterocyclo, O(alkyl), O(SI)(C$_{1-4}$alkyl)$_3$, or C$_{1-4}$alkyl substituted with O(alkyl), NH$_2$, NH(C$_{1-4}$alkyl), or N(C$_{1-4}$alkyl)$_2$, or R$^{50}$ and R$^{61}$ together form a four to six membered heterocyclo ring, wherein when R$^{50}$ or R$^{51}$ is a heterocyclo, said heterocyclo in turn is optionally substituted with lower alkyl, NH$_2$, NH(C$_{1-4}$alkyl), or N(C$_{1-4}$alkyl)$_2$;

$R^{60}$ is hydrogen, alkyl, pyridyl or pyrimidinyl in turn optionally substituted with C$_{1-4}$alkyl, S(alkyl), NH$_2$, NH(C$_{1-4}$alkyl), N(C$_{1-4}$alkyl)$_2$, or C$_{1-6}$alkyl substituted with O(alkyl), NH$_2$, NH(C$_{1-4}$alkyl), N(C$_{1-4}$alkyl)$_2$, or five or six membered heterocyclo;

$R^{62}$ is selected from phenyl, tetrahydrofuryl, azetidinyl, morpholinyl, thiamorpholinyl, piperazinyl, pyrrolidinyl, diazapinyl, seven membered bicyclic heterocyclo having at least one nitrogen atom and zero or one oxygen atom, wherein each R$^{62}$ in turn is optionally substituted with one to two of OH, SO$_2$(alkyl), CH$_2$—OH, CH$_2$—OCH$_3$, NHC(=O)CH$_3$, NH$_2$, NH(C$_{1-4}$alkyl), and/or N(C$_{1-4}$alkyl)$_2$;

d is 0, 1, or 2;

f is 0, 1, 2 or 3; and g is 0, 1 or 2.

5. A compound having the formula (I), (I)

or an enantiomer, diastereomer, tautomer or pharmaceutically acceptable salt, solvate, or prodrug thereof, wherein:

$X^1$ is CR$^1$;

$X^2$ is selected from CR$^{25}$ and N;

$X^3$ is CR$^1$;

$X^4$ is CR$^1$;

$X^5$ is CR$^1$;

$X^6$ is selected from CR$^{25}$ and N;

$X^7$ is CR$^1$;

$X^8$, $X^9$, $X^{10}$ and $X^{11}$ are C;

Provided, however, that at least one of $X^2$ and $X^6$ is N; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;

W is —C(=O)—, —S(=O)—, or —S(O)$_2$—; or W may be —CH$_2$— if X is —C(=O)—, —S(=O)—, or —S(O)$_2$—;

X is selected from —CH$_2$—, —N(R$^4$)—, and —O—, except that when W is —CH$_2$—, X is selected from —C(=O)—, —S(=O)—, or —S(O)$_2$—;

Y is a bond or —C(R$^{40}$)(R$^{45}$)—;

Q is selected from a bond, —C(R$^{26}$)(R$^{48}$)—, —C(=O)—, —CH$_2$—O—, —CH$_2$—O—CH$_2$—, —CH$_2$—CO$_2$NR$^4$—, —CH$_2$—CO$_2$—, —C(=O)NR$^4$—, and —CH=C(R$^{26}$)—;

$R^1$ is the same or different and is selected from hydrogen, halogen, cyano, alkyl, substituted alkyl, alkenyl, substituted alkenyl, alkynyl, substituted alkynyl, O—R$^7$, —(C=O)R⁷, —(C=O)—O—R⁷, NR⁸R⁹, —(CO)NR⁸R⁹, —SR²⁰, —S(=O)R²⁰, —SO₂R²⁰ and —C≡C—SI(CH₃)₃;

R³ is selected from H, OH and NH₂;

R⁴ is selected from H, OH and C₁₋₄alkyl;

R⁷ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(=O)heterocyclo, —C(=O)—NR⁸R⁹, C(=O)heteroaryl, aryl, substituted aryl, heterocyclo, substituted heterocyclo, heteroaryl and substituted heteroaryl;

R⁸ and R⁹ are independently selected from hydrogen, OR⁷, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or R⁸ and R⁹ are taken together with the nitrogen atom to which they are attached to form a substituted or unsubstituted heterocyclic ring of 3 to 8 atoms, or substituted or unsubstituted heteroaryl ring of 5 atoms;

R²⁰ is selected from alkyl and substituted alkyl;

R²⁶ is the same or different and is selected from hydrogen, halogen, nitro, cyano, alkyl, substituted alkyl, alkenyl, substituted alkenyl, alkynyl, substituted alkynyl, O—R⁷, NR⁸R⁹SR⁷, S(O)R⁷, SO₂R⁷, SO₃R⁷, SO₂NR⁸R⁹, —C(=O)R⁷, CO₂R⁷, C(=O)NR⁸R⁹, and —C≡C—SI(CH₃)₃;

R³⁰ is selected from =O and =S;

R²⁶ and R⁴⁶ are independently selected from hydrogen, C₁₋₄alkyl, hydroxy, halogen, hydroxyC₁₋₄alkyl, haloC₁₋₄alkyl, and heterocycloC₁₋₄alkyl, or taken together form a C₃₋₇cycloalkyl ring;

R⁴⁰ and R⁴⁵ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or R⁴⁰ and R⁴⁵ are taken together to form a substituted or unsubstituted cycloalkyl ring of 3 to 8 atoms or a substituted or unsubstituted heterocyclo ring of 3 to 8 atoms; and Z is selected from methyl, ethyl, 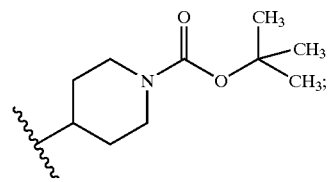

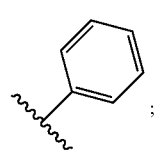

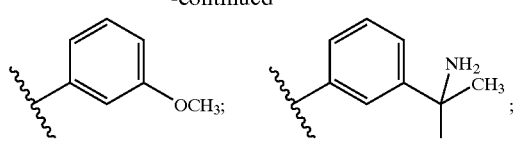

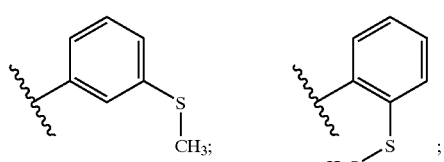

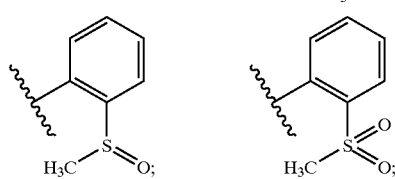

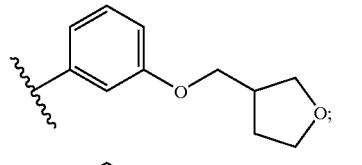

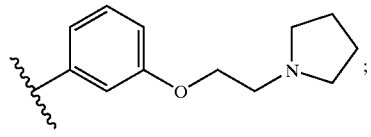

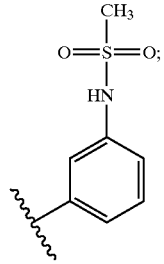

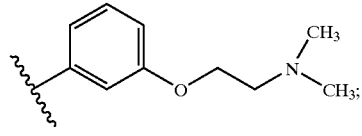

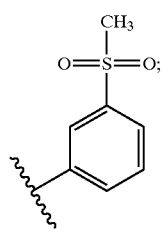
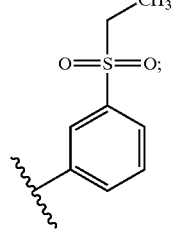

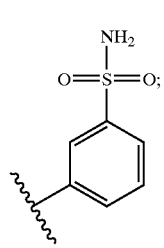
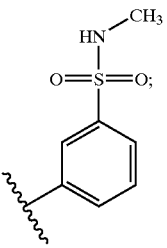

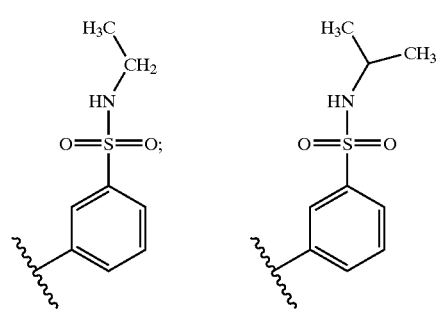
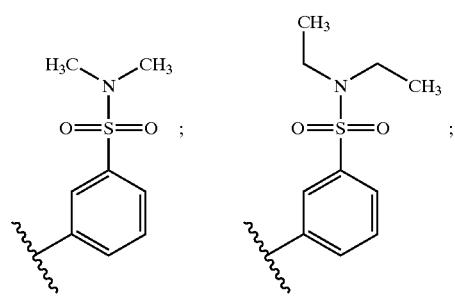
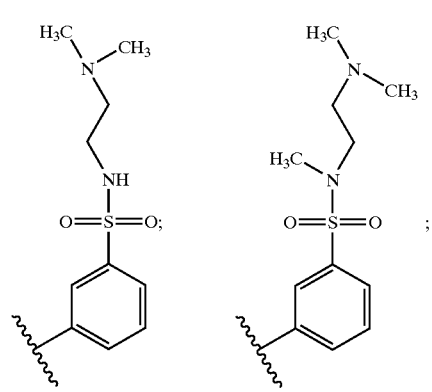
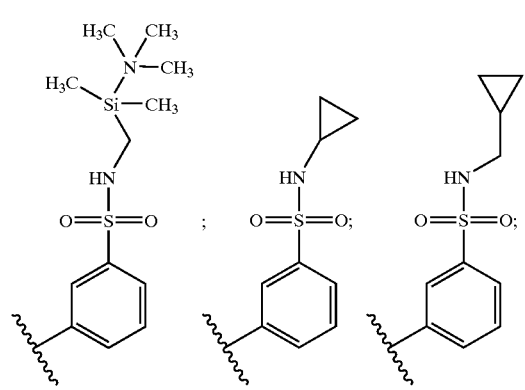
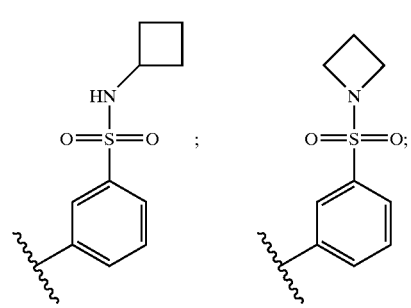
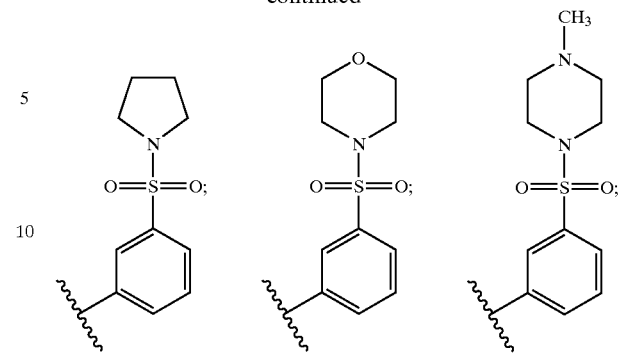
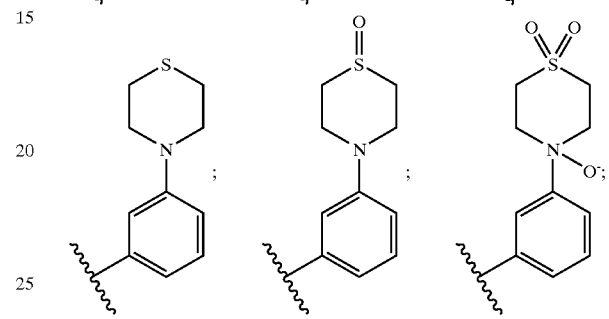
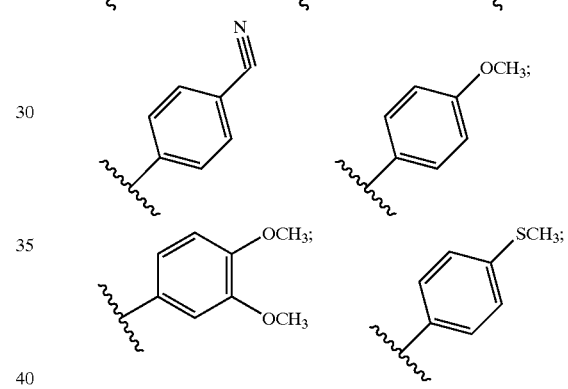
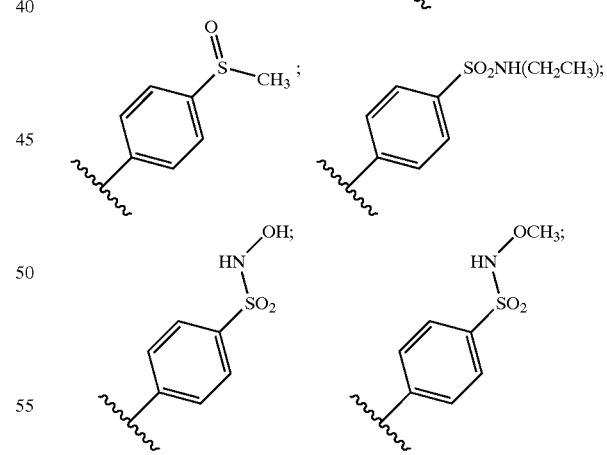
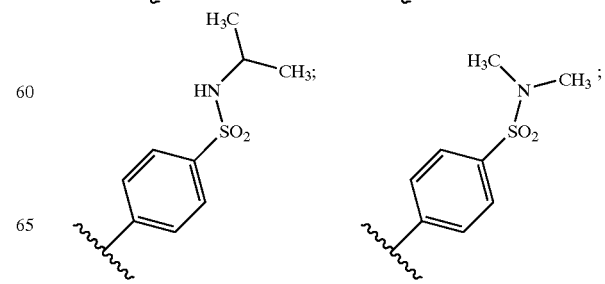

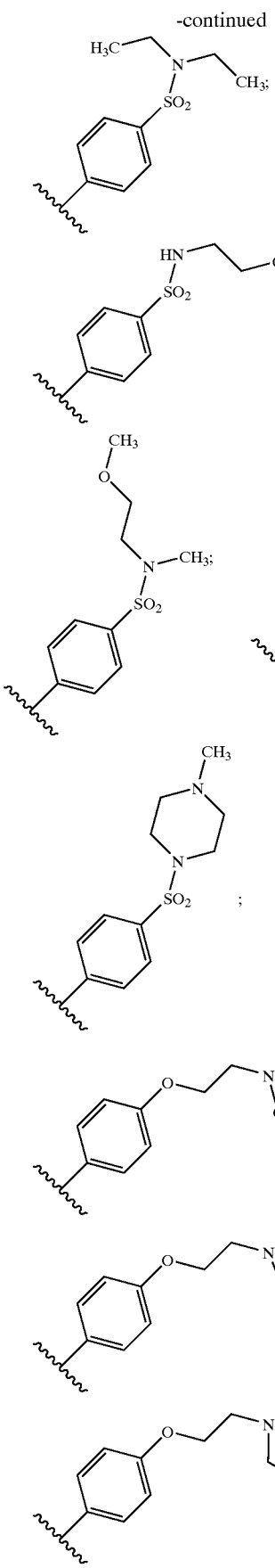
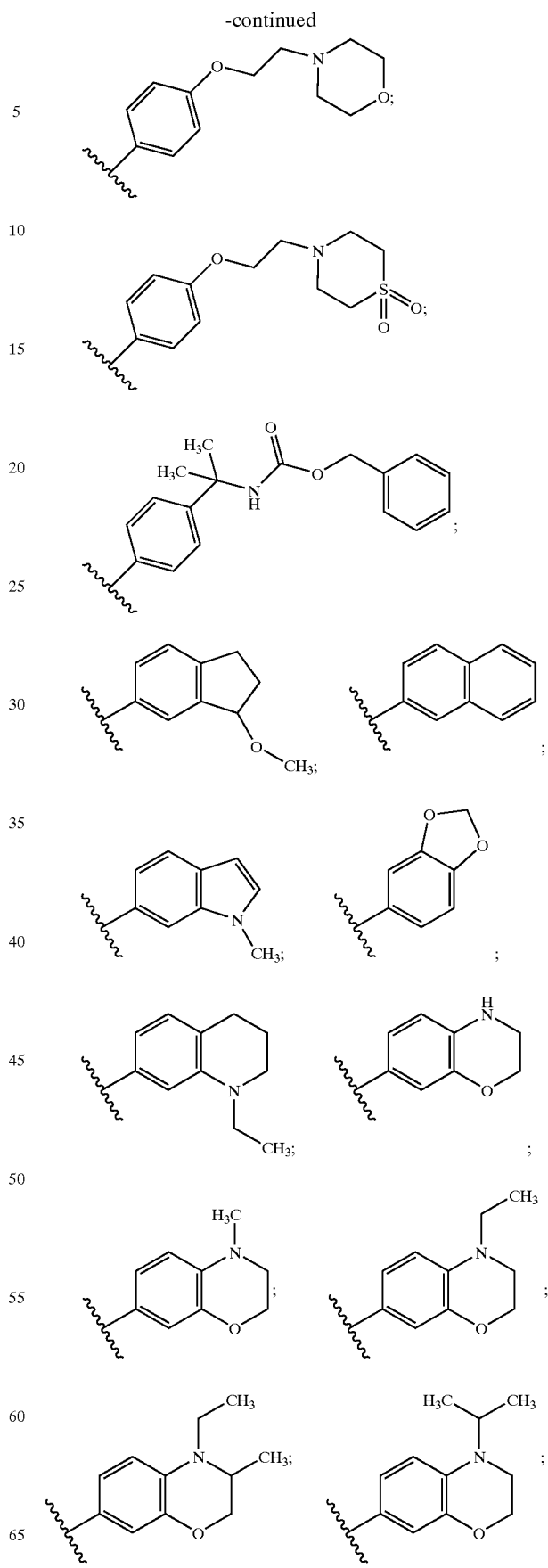

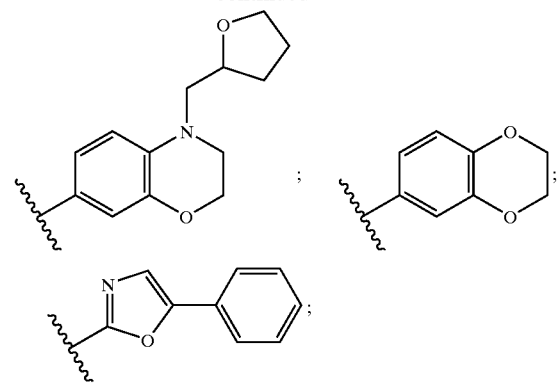
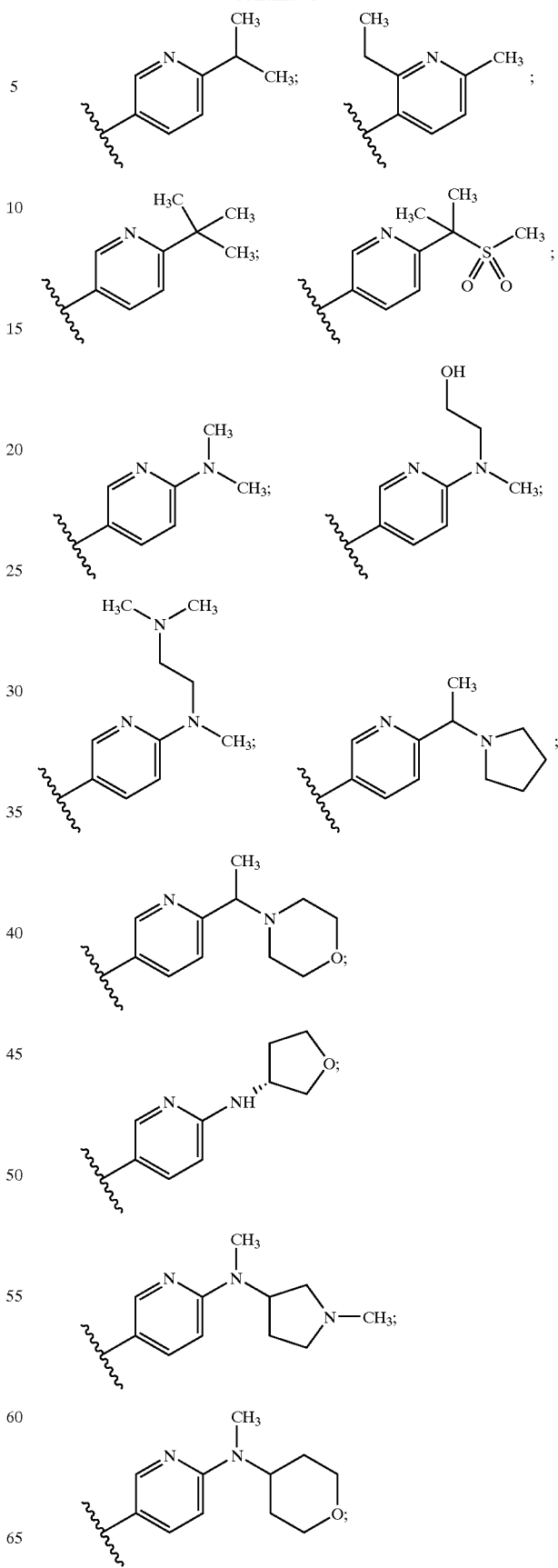

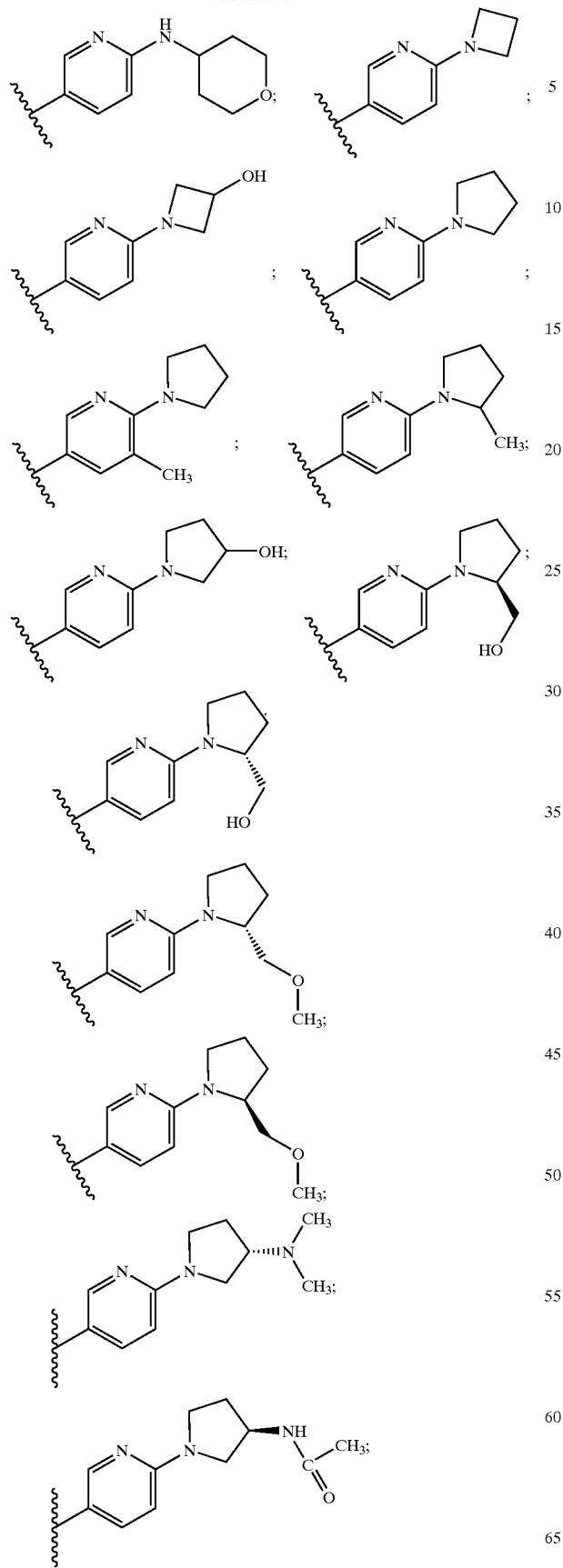
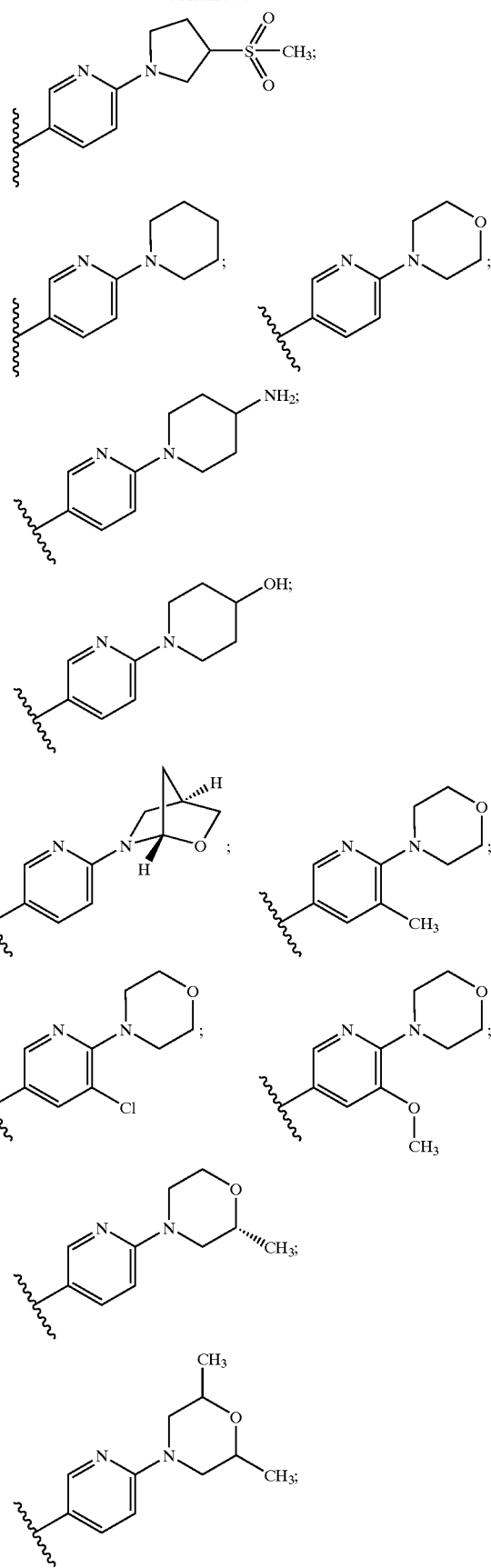

65
-continued
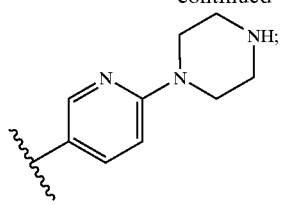
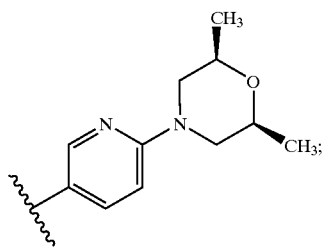
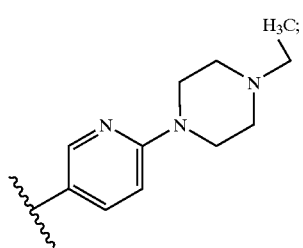
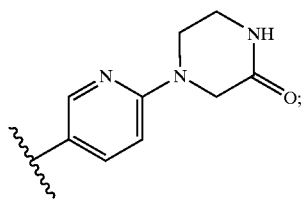
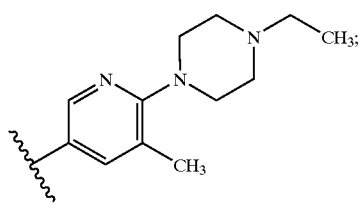
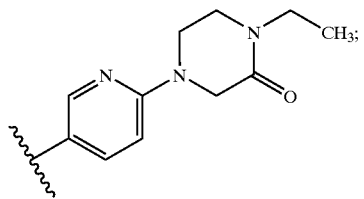
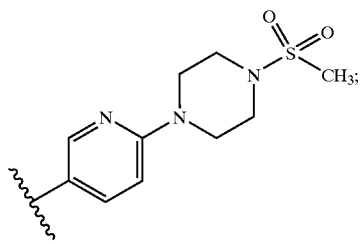
66
-continued
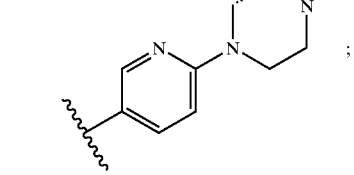
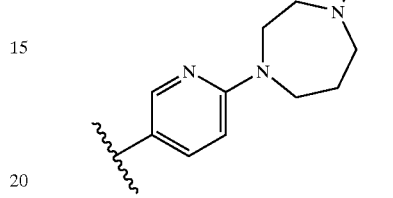
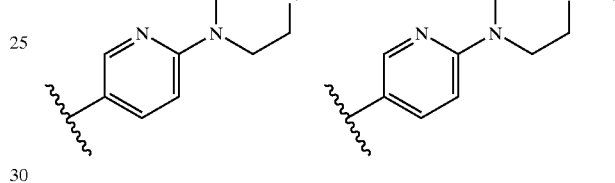
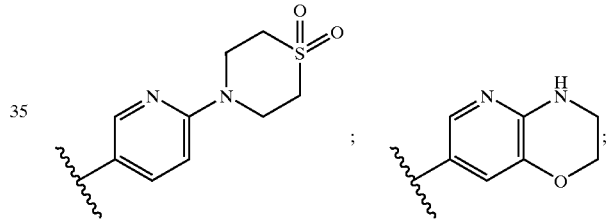
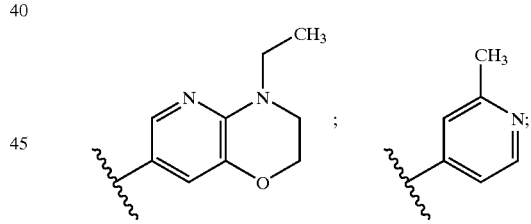
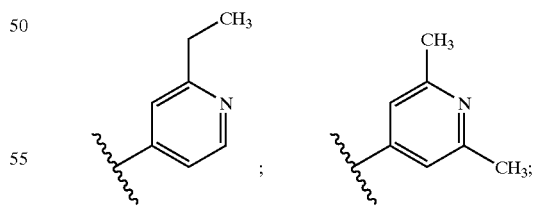
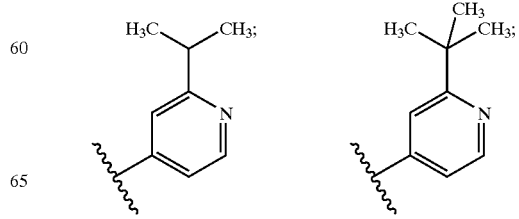

-continued
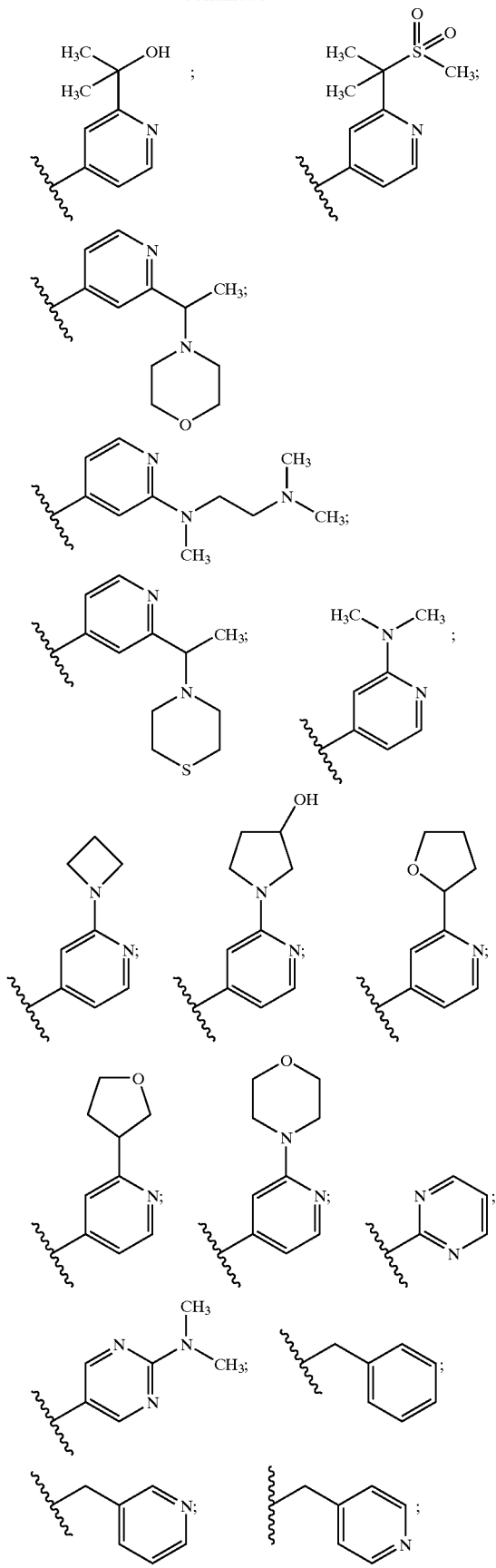
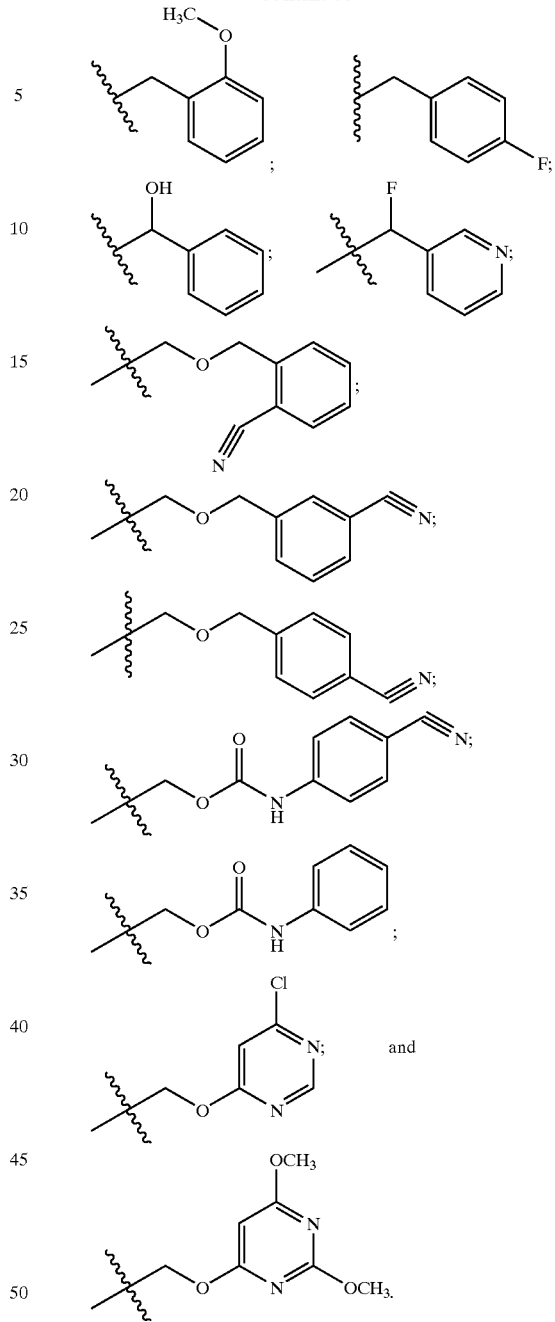
6. A compound having the formula (I),
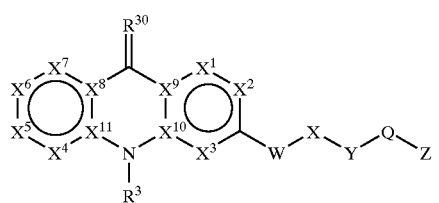
or an enantiomer, diastereomer, tautomer or pharmaceutically acceptable salt, solvate, or prodrug thereof, wherein:

$X^1$ is $CR^1$;

$X^2$ is selected from $CR^{25}$ and N;

$X^3$ is $CR^1$;

$X^4$ is $CR^1$;

$X^5$ is $CR^1$;

$X^6$ is selected from $CR^{25}$ and N;

$X^7$ is $CR^1$;

$X^8$, $X^9$, $X^{10}$ and $X^{11}$ are C;

Provided, however, that at least one of $X^2$ and $X^8$ is N; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;

W is —C(=O)—, —S(=O)—, or —S(O)$_2$—; or W may be —CH$_2$— if X is —C(=O)—, —S(=O)—, or —S(O)$_2$—;

X is selected from —CH$_2$—, —N(R$^4$)—, and —O—, except that when W is —CH$_2$—, X is selected from —C(=O)—, —S(=O)—, or —S(O)$_2$—;

Y is a bond;

Q is selected from a bond, —C(R$^{26}$)(R$^{45}$)—, —C(=O)—, —CH$_2$—O—, —CH$_2$—O—CH$_2$—, —CH$_2$—CO$_2$—NR$^4$—, —CH$_2$CO$_2$—, —C(=O)NR$^4$—, and —CH=C(R$^{26}$)—;

$R^1$ is the same or different and is selected from hydrogen, halogen, cyano, alkyl, substituted alkyl, alkenyl, substituted alkenyl, alkynyl, substituted alkynyl, O—R$^7$, —(C=O)R$^7$, —(C=O)—O—R$^7$, NR$^8$R$^9$, —(C=O)NR$^8$R$^9$, —SR$^{20}$, —S(=O)R$^{20}$, —SO$_2$R$^{20}$ and —C≡C—SI(CH$_3$)$_3$;

$R^3$ is selected from H, OH and NH$_2$;

$R^4$ is selected from H, OH and C$_{1-4}$ alkyl;

$R^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(=O)heterocyclo, —C(=O)—NR$^8$R$^9$, C(=O)heteroaryl, aryl, substituted aryl, heterocyclo, substituted heterocyclo, heteroaryl and substituted heteroaryl;

$R^8$ and $R^9$ are independently selected from hydrogen, OR$^7$, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or $R^8$ and $R^9$ are taken together with the nitrogen atom to which they are attached to form a substituted or unsubstituted heterocyclic ring of 3 to 8 atoms, or substituted or unsubstituted heteroaryl ring of 5 atoms;

$R^{20}$ is selected from alkyl and substituted alkyl;

$R^{25}$ is the same or different and is selected from hydrogen, halogen, nitro, cyano, alkyl, substituted alkyl, alkenyl, substituted alkenyl, alkynyl, substituted alkynyl, O—R$^7$, NR$^8$R$^9$, SR$^7$, S(O)R$^7$, SO$_2$R$^7$, SO$_3$R$^7$, SO$_2$NR$^8$R$^9$, —C(=O)R$^7$, CO$_2$R$^7$, C(=O)NR$^8$R$^9$, and —C≡C—SI(CH$_3$)$_3$;

$R^{30}$ is selected from =O and =S;

$R^{26}$ and $R^{48}$ are independently selected from hydrogen, C$_{1-4}$alkyl, hydroxy, halogen, hydroxyC$_{1-4}$alkyl, haloC$_{1-4}$alkyl, and heterocycloC$_{1-4}$alkyl, or taken together form a C$_{3-7}$cycloalkyl ring; and Z is selected from

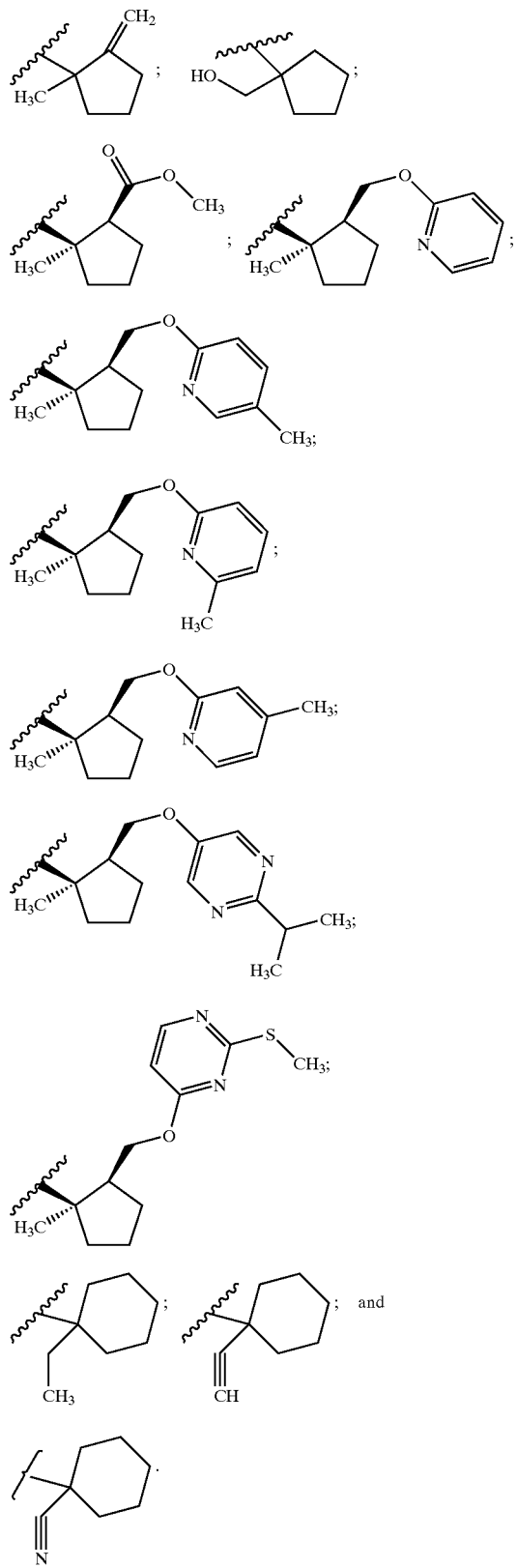

7. A compound having the formula (I),

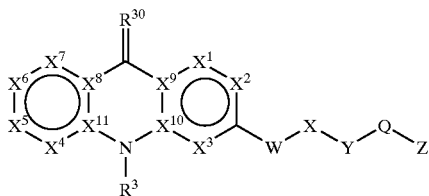

or an enantiomer, diastereomer, tautomer or pharmaceutically acceptable salt, solvate, or prodrug thereof,
wherein:
$X^1$ is $CR^1$;
$X^2$ is selected from $CR^{25}$ and N;
$X^3$ is $CR^1$;
$X^4$ is $CR^1$;
$X^5$ is $CR^1$;
$X^6$ is selected from $CR^{25}$ and N;
$X^7$ is $CR^1$;
$X^8$, $X^9$, $X^{10}$ and $X^{11}$ are C;
Provided, however, that at least one of $X^2$ and $X^8$ is N; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;
the groups W—X—Y—Q—Z taken together are selected from:

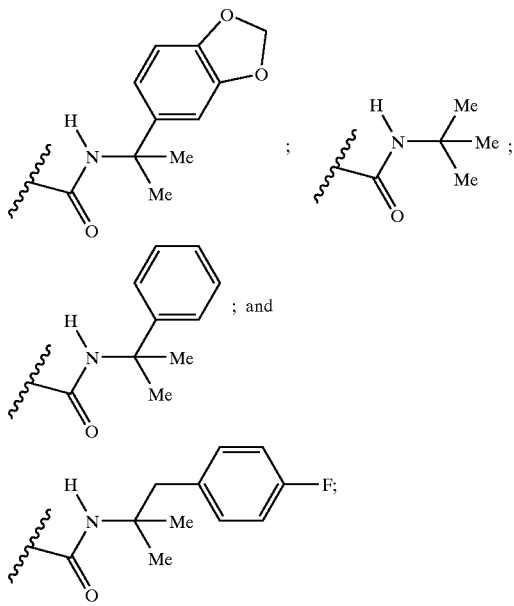

$R^1$ is the same or different and is selected from hydrogen, halogen, cyano, alkyl, substituted alkyl, alkenyl, substituted alkenyl, alkynyl, substituted alkynyl, O—$R^7$, —(C=O)$R^7$, —(C=O)—O—$R^7$, $NR^8R^9$, —(C=O) $NR^8R^9$, —$SR^{20}$, —S(=O)$R^{20}$, —$SO_2R^{20}$ and —C≡C—Si(CH$_3$)$_3$;
$R^3$ is selected from H, OH and NH$_2$;
$R^7$ is selected from hydrogen, alkyl, substituted alkyl, alkenyl, alkynyl, cycloalkyl, substituted cycloalkyl, C(=O)alkyl, C(=O)substituted alkyl, C(=O) cycloalkyl, C(=O) substituted cycloalkyl, C(=O)aryl, C(=O)substituted aryl, C(=O)O-alkyl, C(=O)O-substituted alkyl, C(=O)heterocyclo, —C(=O)—NR$^8$R$^9$, C(=O)heteroaryl, aryl, substituted aryl, heterocyclo, substituted heterocyclo, heteroaryl and substituted heteroaryl;
$R^8$ and $R^9$ are independently selected from hydrogen, OR$^7$, alkyl, substituted alkyl, cycloalkyl, substituted cycloalkyl, C(=O)alkyl, C(=O)substituted alkyl, C(=O)cycloalkyl C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or R$^8$ and R$^9$ are taken together with the nitrogen atom to which they are attached to form a substituted or unsubstituted heterocyclic ring of 3 to 8 atoms, or substituted or unsubstituted heteroaryl ring of 5 atoms;
$R^{20}$ is selected from alkyl and substituted alkyl;
$R^{25}$ is the same or different and is selected from hydrogen, halogen, nitro, cyano, alkyl, substituted alkyl, alkenyl, substituted alkenyl, alkynyl, substituted alkynyl, O—R$^7$, NR$^8$R$^9$, SR$^7$, S(O)R$^7$, SO$_2$R$^7$, SO$_3$R$^7$, SO$_2$NR$^8$R$^9$, —C(=O)R$^7$, CO$_2$R$^7$, C(=O)NR$^8$R$^9$, and —C≡C—Si(CH$_3$)$_3$; and
$R^{30}$ is selected from =O and =S.

8. A pharmaceutical composition comprising a compound having the formula (I),

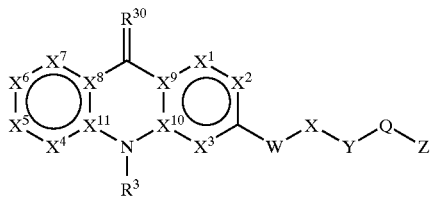

or an enantiomer, diastereomer, tautomer or pharmaceutically acceptable salt, solvate, or prodrug thereof,
wherein:
$X^1$ is $CR^1$;
$X^2$ is selected from $CR^{25}$ and N;
$X^3$ is $CR^1$;
$X^4$ is $CR^1$;
$X^5$ is $CR^1$;
$X^6$ selected from $CR^{25}$ and N;
$X^7$ is $CR^1$;
$X^8$, $X^9$, $X^{10}$ and $X^{11}$ are C;
Provided, however, that at least one of $X^2$ and $X^6$ is N; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;
W is —C(=O)—, —S(=O)—, or —S(O)$_2$—; or W may be —CH$_2$— if X is —C(=O)—, —S(=O)—, or —S(O)$_2$—;
X is selected from —CH$_2$—, —N(R$^4$)—, and —O—, except that when W is —CH$_2$, X is selected from —C(=O)—, —S(=O)—, or —S(O)$_2$—;
Y is a bond or —C(R$^{40}$)(R$^{45}$)—;
Q is selected from a bond, —C(R$^{26}$)(R$^{48}$)—, —C(=O)—, —CH$_2$O—, —CH$_2$—O—CH$_2$—, —CH$_2$—CO$_2$NR$^4$—, —CH$_2$—CO$_2$—, —C(=O) NR$^4$—, and —CH=C(R$^{26}$)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C($R^{40}$)($R^{45}$)— and Q is a bond or —C($R^{26}$)($R^{46}$)—, Z may be $CO_2H$ or $CO_2$alkyl;

$R^1$ is the same or different and is selected from hydrogen, halogen, cyano, alkyl, substituted alkyl, alkenyl, substituted alkenyl, alkynyl, substituted alkynyl, O—$R^7$, —(C=O)$R^7$, —(C=O)—O—$R^7$, $NR^8R^9$, —(C=O)$NR^8R^9$, —$SR^{20}$, —S(=O)$R^{20}$, —$SO_2R^{20}$ and —C≡C—Si($CH_3$)$_3$;

$R^3$ is selected from H, OH and $NH_2$;

$R^4$ is selected from H, OH and $C_{1-4}$ alkyl;

$R^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(O)heterocyclo, —C(=O)—$NR^8R^9$, C(=O)heteroaryl, aryl, substituted aryl, heterocyclo, substituted heterocyclo, heteroaryl and substituted heteroaryl;

$R^8$ and $R^9$ are independently selected from hydrogen, $OR^7$, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=C))O-substituted alkyl, C(=O)heterocyclo, C(=O)heteroaryl, aryl, substituted aryl, heterocyclyl, substituted heterocyclyl, heteroaryl and substituted heteroaryl, or $R^8$ and $R^9$ are taken together with the nitrogen atom to which they are attached to form a substituted or unsubstituted heterocyclic ring of 3 to 8 atoms, or substituted or unsubstituted heteroaryl ring of 5 atoms;

$R^{20}$ is selected from alkyl and substituted alkyl;

$R^{25}$ is the same or different and is selected from hydrogen, halogen, nitro, cyano, alkyl, substituted alkyl, alkenyl, substituted alkenyl, alkynyl, substituted alkynyl, O—$R^7$, $NR^8R^9$, $SR^7$, S(O)$R^7$, $SO_2R^7$, $SO_3R^7$, $SO_2NR^8R^9$, —C(=O)$R^7$, $CO_2R^7$, C(=O)$NR^8R^9$, and —C≡C—Si($CH_3$)$_3$;

$R^{50}$ is selected from =O and =S;

$R^{20}$ and $R^{40}$ are independently selected from hydrogen, $C_{1-4}$alkyl, hydroxy, halogen, hydroxy$C_{1-4}$alkyl halo-$C_{1-4}$alkyl, and heterocyclo$C_{1-4}$alkyl, or taken together form a $C_{3-7}$ cycloalkyl ring;

$R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to a atoms;

and a pharmaceutically acceptable carrier.

9. A method of treating at least one inosine monophosphate dehydrogenase associated disorder, wherein the disorder is selected from psoriasis, transplant rejection, and rheumatoid arthritis, comprising administering to a subject in need of treatment thereof an effective amount of at least one compound having the formula (I),

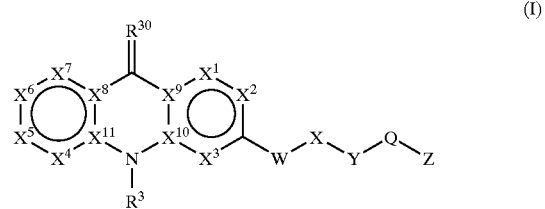

(I)

or an enantiomer, diastereomer, tautomer or pharmaceutically acceptable salt, solvate, or prodrug thereof,
wherein:

$X^1$ is $CR^1$;

$X^2$ is selected from $CR^2$ and N;

$X^3$ $CR^1$;

$X^4$ is $CR^1$;

$X^5$ is $CR^1$;

$X^6$ is selected from $CR^{25}$ and N;

$X^7$ is $CR^1$;

$X^8$, $X^9$, $X^{10}$ and $X^{11}$ are C;

Provided, however, that at least one of $X^2$ and $X^5$ is N; and provided further that $X^1$, $X^2$, $X^3$, $X^4$, $X^5$, $X^6$, $X^7$, $X^8$, $X^9$, $X^{10}$ and $X^{11}$ are selected such that a tricyclic heteroaryl ring system is formed;

W is —C(=O)—, —S(=O)—, or —S(O)$_2$—; or W may be —$CH_2$— if X is —C(=O)—, —S(=O)—, or —S(O)$_2$—;

X is selected from —$CH_2$—, —N($R^4$)—, and —O—, except that when W is —$CH_2$—, X is selected from —C(=O)—, —S(=O)—, or —S(O)$_2$—;

Y is a bond or —C($R^{40}$)($R^{45}$)—;

Q is selected from a bond, —C($R^{26}$)($R^{46}$)—, —C(=O)—, —$CH_2$—O—, —$CH_2$—O—$CH_2$—, —$CH_2$—$CO_2$—$NR^4$—, —$CH_2$—$CO_2$—, —C(=O)$NR^4$—, and —CH=C($R^{26}$)—;

Z is selected from alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl, and when Y is —C($R^{40}$)($R^{45}$)— and Q is a bond or —C($R^{28}$)($R^{46}$)—, Z may be $CO_2H$ or $CO_2$alkyl;

$R^1$ is the same or different and is selected from hydrogen, halogen, cyano, alkyl, substituted alkyl, alkenyl, substituted alkenyl, alkynyl, substituted alkynyl, O—$R^7$, —(C=O)$R^7$, —(C=O)—O—$R^7$, $NR^8R^9$, —(C=O)$NR^8R^9$, —$SR^{20}$, —S(=O)$R^{20}$, —$SO_2R^{20}$ and —C≡C—Si($CH_3$)$_3$;

$R^3$ is selected from H, OH and $NH_2$;

$R^4$ is selected from H, OH and $C_{1-4}$ alkyl;

$R^7$ is selected from hydrogen, alkyl, substituted alkyl, alkenyl, alkynyl, cycloalkyl, substituted cycloalkyl, C(=O)alkyl, C(=O)substituted alkyl, C(=O)cycloalkyl, C(=O) substituted cycloalkyl, C(=O)aryl, C(=O)substituted aryl, C(=O)O-alkyl, C(=O)O-substituted alkyl, C(=O)heterocyclo, —C(=O)—$NR^8R^9$, C(=O)heteroaryl, aryl, substituted aryl, heterocyclo, substituted heterocyclo, heteroaryl and substituted heteroaryl;

$R^8$ and $R^9$ are independently selected from hydrogen, $OR^7$, alkyl, substituted alkyl, cycloalkyl, substituted cycloalkyl, C(=O)alkyl, C(=O)substituted alkyl, C(=O)cycloalkyl, C(=O)substituted cycloalkyl, C(=O)aryl, C(=O)substituted aryl, C(=O)O-alkyl, C(=O)O-substituted alkyl, C(=O)heterocyclo, C(=O)heteroaryl, aryl, substituted aryl, heterocyclyl, substituted heterocyclyl, heteroaryl and substituted heteroaryl, or $R^8$ and $R^9$ are taken together with the nitrogen atom to which they are attached to form a substituted or unsubstituted heterocyclic ring of 3 to 8 atoms, or substituted or unsubstituted heteroaryl ring of 5 atoms;

$R^{20}$ is selected from alkyl and substituted alkyl;

$R^{25}$ is the same or different and is selected from hydrogen, halogen, nitro, cyano, alkyl, substituted alkyl, alkenyl, substituted alkenyl, alkynyl, substituted alkynyl, O—$R^7$, $NR^8R^9$, $SR^7$, $S(O)R^7$, $SO_2R^7$, $SO_3R^7$, $SO_2NR^8R^9$, —C(=O)$R^7$, $CO_2R^7$, C(=O)$NR^8R^9$, and —C≡O—Si(CH$_3$)$_3$;

$R^{30}$ is selected from =O and =S;

$R^{28}$ and $R^{46}$ are independently selected from hydrogen, $C_{1-4}$alkyl, hydroxy, halogen, hydroxy$C_{1-4}$alkyl, halo$C_{1-4}$alkyl, and heterocyclo$C_{1-4}$alkyl, or taken together form a $C_{3-7}$ cycloalkyl ring; and $R^{40}$ and $R^{45}$ are independently selected from hydrogen, cyano, alkyl, substituted alkyl, alkenyl, substituted alkenyl, alkynyl, substituted alkynyl, cycloalkyl, substituted cycloalkyl, aryl, substituted aryl, heterocyclo, substituted heterocyclo, heteroaryl and substituted heteroaryl, or $R^{40}$ and $R^{45}$ are taken together to form a substituted or unsubstituted cycloalkyl ring of 3 to 8 atoms or a substituted or unsubstituted heterocyclo ring of 3 to 8 atoms.

* * * * *

UNITED STATES PATENT AND TRADEMARK OFFICE
CERTIFICATE OF CORRECTION

PATENT NO. : 6,916,809 B2  Page 1 of 4
APPLICATION NO. : 10/325009
DATED : July 12, 2005
INVENTOR(S) : Chen et al.

It is certified that error appears in the above-identified patent and that said Letters Patent is hereby corrected as shown below:

Column 48, lines 46-55,

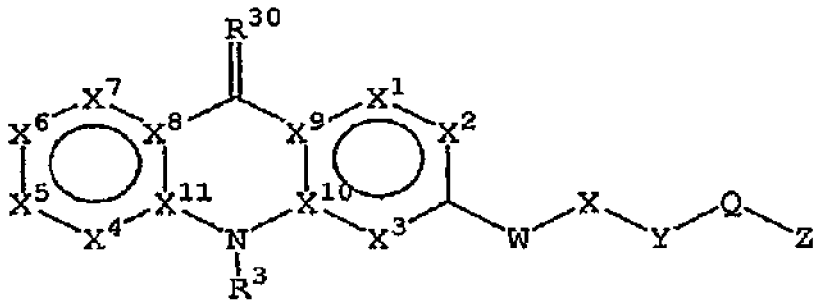

should read:

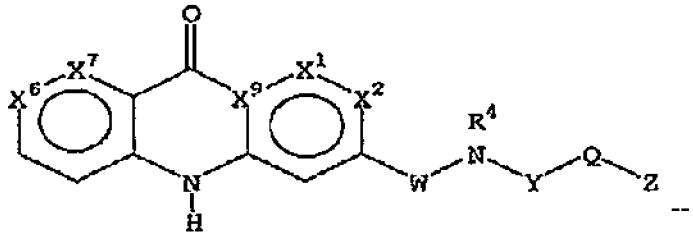

-- --

Column 49, lines 3-6, "Q is selected from a bond, -C($R^{26}$)($R^{48}$)-, -C(=O)-, -CH$_2$-O-, -CH$_2$-O-CH$_2$-CO$_2$-NR$^4$-, -CH$_2$-CO$_2$-, -C(=O)NR$^4$-, and -CH=C($R^{25}$)-;" should read : -- Q is selected from a bond, -C($R^{26}$)($R^{46}$)-, -C(=O)-, -CH$_2$-O-, -CH$_2$-O-CH$_2$-, -CH$_2$-CO$_2$-NR$^4$-, -CH$_2$-CO$_2$-, -C(=O)NR$^4$-, and -CH=C($R^{26}$)-; --

Column 50, lines 8-12, "both a bond, Z is $Z^1$; and when Y is –C($R^{40}$)($R^{46}$)– and Q is selected from a bond, -C($R^{26}$)($R^{46}$)-, -C(=O)-, -CH$_2$-O-CH$_2$-, -CH$_2$-CO$_2$-NR$^4$-, -CH$_2$-CO$_2$-, -C(=O)NR$^4$-, and -CH=C(C$R^{26}$)-, then Z is $Z^2$;" Should read: -- both a bond, Z is $Z^1$; and when Y is –C($R^{40}$)($R^{45}$)– and Q is selected from a bond, -C($R^{26}$)($R^{46}$)-, -C(=O)-, -CH$_2$-O-, -CH$_2$-O-CH$_2$-, -CH$_2$-CO$_2$-NR$^4$-, -CH$_2$-CO$_2$-, -C(=O)NR$^4$-, and -CH=C(C$R^{26}$)-, then Z is $Z^2$; --

Column 49, line 58, "heteroaryl, or $R^6$ and $R^9$ are taken together with the" should read: -- heteroaryl, or $R^8$ and $R^9$ are taken together with the --

Column 50, line 3, "$R^{28}$ and $R^{46}$ are independently selected from hydrogen," should read: -- $R^{26}$ and $R^{46}$ are independently selected from hydrogen, --

UNITED STATES PATENT AND TRADEMARK OFFICE
CERTIFICATE OF CORRECTION

PATENT NO.       : 6,916,809 B2                                    Page 2 of 4
APPLICATION NO. : 10/325009
DATED            : July 12, 2005
INVENTOR(S)      : Chen et al.

It is certified that error appears in the above-identified patent and that said Letters Patent is hereby corrected as shown below:

Column 50, line 23, "selected from $R^{62}$, $NR^{50}R^{51}$, $OR^{50}$, and $SO_2(alkyl)$;" should read:
-- selected from $R^{62}$, $NR^{50}R^{61}$, $OR^{60}$, and $SO_2(alkyl)$; --

Column 50, line 27, "$SO_2NR^{50}R^{51}$, $NR^{60}R^{51}$, $OR^{60}$; or a group $R^{62}$; or a" should read:
-- $SO_2NR^{50}R^{51}$, $NR^{50}R^{51}$, $OR^{60}$; or a group $R^{62}$; or a --

Column 51, line 1, "$X^5$ is N" should read: -- $X^6$ is N --

Column 54, line 1, "heterocyclo, O(alkyl), $O(SI)(C_{1-4}alkyl)_3$, or $C_{1-4}alkyl$" should read:
-- heterocyclo, O(alkyl), $O(\mathbf{Si})(C_{1-4}alkyl)_3$, or $C_{1-4}alkyl$ --

Column 54, lines 61-63, "Q is selected from a bond, $-C(R^{26})(R^{48})-$, $-C(=O)-$, $-CH_2-O-$, $-CH_2-O-CH_2-$, $-CH_2-CO_2NR^4-$, $-CH_2-CO_2-$, $-C(=O)$" should read:
-- Q is selected from a bond, $-C(R^{26})(\mathbf{R^{46}})-$, $-C(=O)-$, $-CH_2-O-$, $-CH_2-O-CH_2-$, $-CH_2-\mathbf{CO_2-NR^4}-$, $-CH_2-CO_2-$, $-C(=O)$ --

Column 55, line 3, "$-C\equiv C-SI(CH_3)_3$;" should read: -- $-C\equiv C-\mathbf{Si}(CH_3)_3$; --

Column 55, line 32, "$R^{26}$ is the same or different and is selected from hydrogen," should read: --$R^{25}$ is the same or different and is selected from hydrogen, --

Column 55, lines 35-37, "$O-R^7$, $NR^8R^9SR^7$, $S(O)R^7$, $SO_2R^7$, $SO_3R^7$, $SO_2NR^8R^9$, $-C(=O)R^7$, $CO_2R^7$, $C(=O)NR^8R^9$, and $-C\equiv C-SI(CH_3)_3$;" should read: -- $O-R^7$, $NR^8\mathbf{R^9}$, $\mathbf{SR^7}$, $S(O)R^7$, $SO_2R^7$, $SO_3R^7$, $SO_2NR^8R^9$, $-C(=O)R^7$, $CO_2R^7$, $C(=O)NR^8R^9$, and $-C\equiv C-\mathbf{Si}(CH_3)_3$; --

Column 57, lines 40-55, should read:

-- 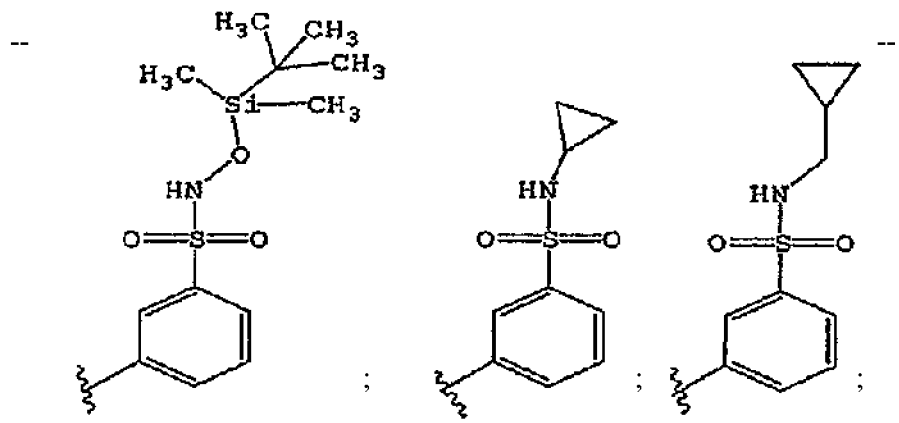 --

UNITED STATES PATENT AND TRADEMARK OFFICE
CERTIFICATE OF CORRECTION

PATENT NO. : 6,916,809 B2
APPLICATION NO. : 10/325009
DATED : July 12, 2005
INVENTOR(S) : Chen et al.

It is certified that error appears in the above-identified patent and that said Letters Patent is hereby corrected as shown below:

Column 69, line 10, "Provided, however, that at least one of $X^2$ and $X^8$ is N;" should read : --Provided, however, that at least one of $X^2$ and $\mathbf{X^6}$ is N; --

Column 69, lines 22-24, "Q is selected from a bond, $-C(R^{26})(R^{45})-$, $-C(=O)-$, $-CH_2-O-$, $-CH_2-O-CH_2-$, $CH_2-CO_2-NR^4-$, $-CH_2CO_2-$, $-C(=O)$" should read : -- Q is selected from a bond, $-C(R^{26})(\mathbf{R^{46}})-$, $-C(=O)-$, $-CH_2-O-$, $-CH_2-O-CH_2-$, $-CH_2-CO_2-NR^4-$, $\mathbf{-CH_2-CO_2-}$, $-C(=O)$ --

Column 69, line 32, "$-C\equiv C-SI(CH_3)_3$;" should read: -- $-C\equiv C-\mathbf{Si}(CH_3)_3$; --

Column 69, line 63, "$-C\equiv C-SI(CH_3)_3$;" should read: -- $-C\equiv C-\mathbf{Si}(CH_3)_3$; --

Column 69, line 65, "$R^{26}$ and $R^{48}$ are independently selected from hydrogen," should read : -- $R^{26}$ and $\mathbf{R^{46}}$ are independently selected from hydrogen, --

Column 71, line 25, "Provided, however, that at least one of $X^2$ and $X^8$ is N;" should read : --Provided, however, that at least one of $X^2$ and $\mathbf{X^6}$ is N; --

Column 71, line 61, "$-C\equiv C-SI(CH_3)_3$;" should read: -- $-C\equiv C-\mathbf{Si}(CH_3)_3$; --

Column 72, line 61, "except that when W is $-Ch_2$, X is selected from" should read: -- except that when W is $\mathbf{-CH_2-}$, $\mathbf{X}$ is selected from --

Column 72, lines 64-66, "Q is selected from a bond, $-C(R^{26})(R^{48})-$, $-C(=O)-$, $-CH_2O-$, $-CH_2-O-CH_2-$, $-CH_2-CO_2NR^4-$, $-CH_2-CO_2-$, $-C(=O)$" should read: -- Q is selected from a bond, $-C(R^{26})(\mathbf{R^{46}})-$, $-C(=O)-$, $\mathbf{-CH_2-O-}$, $-CH_2-O-CH_2-$, $-CH_2-\mathbf{CO_2-NR^4}-$, $-CH_2-CO_2-$, $-C(=O)$ --

Column 73, line 22, "substituted alkyl, C(O)heterocyclo, $-C(=O)-$" should read: -- substituted alkyl, $\mathbf{C(=O)}$heterocyclo, $-C(=O)-$ --

Column 73, line 47, "$R^{50}$ is selected from $=O$ and $=S$;" should read : -- $\mathbf{R^{30}}$ is selected from $=O$ and $=S$; --

Column 73, line 48, "$R^{20}$ and $R^{40}$ are independently selected from hydrogen," should read: -- $\mathbf{R^{26}}$ and $\mathbf{R^{46}}$ are independently selected from hydrogen, --

Column 73, line 60, "of 3 to a atoms;" should read: -- of 3 to $\mathbf{8}$ atoms; --

UNITED STATES PATENT AND TRADEMARK OFFICE
CERTIFICATE OF CORRECTION

PATENT NO. : 6,916,809 B2
APPLICATION NO. : 10/325009
DATED : July 12, 2005
INVENTOR(S) : Chen et al.

It is certified that error appears in the above-identified patent and that said Letters Patent is hereby corrected as shown below:

Column 74, line 16, "$X^2$ is selected from $CR^2$ and N;" should read: -- $X^2$ is selected from $CR^{25}$ and N; --

Column 74, line 24, "Provided, however, that at least one of $X^2$ and $X^5$ is N;" should read: -- Provided, however, that at least one of $X^2$ and $\mathbf{X^6}$ is N; --

Column 74, line 45, "$(R^{45})$- and Q is a bond or $-C(R^{28})(R^{46})$- Z may be" should read: -- $(R^{45})$- and Q is a bond or $-C(\mathbf{R^{26}})(R^{46})$-, Z may be --

Column 75, line 17, "$-C\equiv O-Si(CH_3)_3$;" should read: -- $-C\equiv \mathbf{C}-Si(CH_3)_3$; --

Column 76, line 2, "$R^{28}$ and $R^{46}$ are independently selected from hydrogen," should read: -- $\mathbf{R^{26}}$ and $R^{46}$ are independently selected from hydrogen, --

Signed and Sealed this

Third Day of April, 2007

JON W. DUDAS
*Director of the United States Patent and Trademark Office*